US012796981B2

(12) United States Patent
Bullington et al.

(10) Patent No.: US 12,796,981 B2
(45) Date of Patent: Nov. 17, 2026

(54) FLUID CONTROL DEVICES AND METHODS OF USING THE SAME

(71) Applicant: Magnolia Medical Technologies, Inc., Seattle, WA (US)

(72) Inventors: Gregory J. Bullington, Seattle, WA (US); Jay M. Miazga, Langley, WA (US); Shan E. Gaw, Seattle, WA (US); Timothy F. Ramsey, Seattle, WA (US); Julie A. Schnur, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 750 days.

(21) Appl. No.: 17/869,256

(22) Filed: Jul. 20, 2022

(65) Prior Publication Data

US 2023/0190157 A1 Jun. 22, 2023

Related U.S. Application Data

(63) Continuation of application No. 16/213,005, filed on Dec. 7, 2018, now Pat. No. 11,419,531.

(Continued)

(51) Int. Cl.

*A61B 5/15* (2006.01)
*A61B 5/154* (2006.01)
*A61M 39/22* (2006.01)

(52) U.S. Cl.

CPC .... *A61B 5/150213* (2013.01); *A61B 5/15003* (2013.01); *A61B 5/150099* (2013.01);

(Continued)

(58) Field of Classification Search

CPC ........ A61B 5/150251; A61B 5/150213; A61B 5/15003; A61B 5/150221;

(Continued)

(56) References Cited

U.S. PATENT DOCUMENTS

| | | | |
|---|---|---|---|
| 2,674,265 | A | 4/1954 | Lee |
| 2,697,435 | A | 12/1954 | Benjamin |

(Continued)

FOREIGN PATENT DOCUMENTS

| | | | |
|---|---|---|---|
| AT | 310345 | B | 9/1973 |
| AT | E219383 | T1 | 7/2002 |

(Continued)

OTHER PUBLICATIONS

Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.

(Continued)

*Primary Examiner* — Jason M Sims
*Assistant Examiner* — Kyle W. Kretzer
(74) *Attorney, Agent, or Firm* — COOLEY LLP

(57) ABSTRACT

A fluid control device includes an inlet configured to be placed in fluid communication with a bodily fluid source and an outlet configured to be placed in fluid communication with a fluid collection device. The fluid control device has sequestration portion that can be vented or evacuated. The fluid control device has a first state in which an initial volume of bodily fluid can flow from the inlet to the sequestration portion and a second state in which (1) the initial volume is sequestered in the sequestration portion, and (2) a subsequent volume of bodily fluid, being substantially free of contaminants, can flow through at least a portion of the fluid control device and into the fluid collection device. The fluid control device can transition automatically or in response to an actuation of a portion of the fluid control device after the sequestration portion receives the initial volume.

20 Claims, 11 Drawing Sheets

Related U.S. Application Data

(60) Provisional application No. 62/687,951, filed on Jun. 21, 2018, provisional application No. 62/595,871, filed on Dec. 7, 2017.

(52) U.S. Cl.
CPC .. *A61B 5/150221* (2013.01); *A61B 5/150251* (2013.01); *A61B 5/15074* (2013.01); *A61B 5/150992* (2013.01); *A61B 5/154* (2013.01); *A61M 39/22* (2013.01); *A61B 5/150389* (2013.01); *A61B 5/150503* (2013.01)

(58) Field of Classification Search
CPC .............. A61B 5/150992; A61B 5/154; A61B 5/150099; A61B 5/150389; A61B 5/150229; A61M 39/223; A61M 2039/229
See application file for complete search history.

(56) References Cited

U.S. PATENT DOCUMENTS

| | | | | |
|---|---|---|---|---|
| 2,707,953 | A | | 5/1955 | Ryan |
| 2,876,769 | A | | 3/1959 | Cordova |
| 2,952,258 | A | | 9/1960 | Chandler |
| 2,992,974 | A | | 7/1961 | Belcove et al. |
| 3,013,557 | A | | 12/1961 | Pallotta |
| 3,098,016 | A | | 7/1963 | Sam et al. |
| 3,382,865 | A | | 5/1968 | Worrall, Jr. et al. |
| 3,405,706 | A | | 10/1968 | Paul et al. |
| 3,467,021 | A | | 9/1969 | Green, Jr. et al. |
| 3,467,095 | A | | 9/1969 | Ross et al. |
| 3,494,351 | A | | 2/1970 | Horn et al. |
| 3,494,352 | A | | 2/1970 | Russo et al. |
| 3,577,980 | A | | 5/1971 | Cohen |
| 3,596,652 | A | | 8/1971 | Winkelman |
| 3,604,410 | A | | 9/1971 | Whitacre |
| 3,635,798 | A | | 1/1972 | Kirkham et al. |
| 3,640,267 | A | | 2/1972 | Hurtig et al. |
| 3,648,684 | A | | 3/1972 | Barnwell et al. |
| 3,650,093 | A | | 3/1972 | Rosenberg |
| 3,680,558 | A | | 8/1972 | Kapelowitz |
| 3,696,806 | A | | 10/1972 | Sausse et al. |
| 3,705,018 | A | | 12/1972 | Taylor |
| 3,730,168 | A | | 5/1973 | McWhorter |
| 3,741,197 | A | | 6/1973 | Sanz et al. |
| 3,749,084 | A | | 7/1973 | Cucchiara |
| 3,774,604 | A | * | 11/1973 | Danielsson ......... A61M 39/223 251/309 |
| 3,777,773 | A | | 12/1973 | Tolbert |
| 3,779,383 | A | | 12/1973 | Ayres |
| 3,803,810 | A | | 4/1974 | Rosenberg |
| 3,817,240 | A | | 6/1974 | Ayres |
| 3,831,602 | A | | 8/1974 | Broadwin |
| 3,834,372 | A | | 9/1974 | Turney |
| 3,835,835 | A | | 9/1974 | Thompson et al. |
| 3,848,579 | A | | 11/1974 | Villa-Real |
| 3,848,581 | A | | 11/1974 | Cinqualbre et al. |
| 3,859,998 | A | | 1/1975 | Thomas et al. |
| 3,874,367 | A | | 4/1975 | Ayres |
| 3,886,930 | A | | 6/1975 | Ryan |
| 3,890,203 | A | | 6/1975 | Mehl |
| 3,890,968 | A | | 6/1975 | Pierce et al. |
| 3,937,211 | A | | 2/1976 | Merten |
| 3,943,917 | A | | 3/1976 | Johansen |
| 3,945,380 | A | | 3/1976 | Dabney et al. |
| 3,960,139 | A | | 6/1976 | Bailey |
| 3,978,846 | A | | 9/1976 | Bailey |
| 3,996,923 | A | | 12/1976 | Guerra |
| 4,056,101 | A | | 11/1977 | Geissler et al. |
| 4,057,050 | A | | 11/1977 | Sarstedt |
| 4,062,360 | A | | 12/1977 | Bentley |
| 4,063,460 | A | | 12/1977 | Svensson |
| 4,077,395 | A | | 3/1978 | Woolner |
| 4,106,491 | A | | 8/1978 | Guerra |
| 4,106,497 | A | | 8/1978 | Percarpio |
| 4,133,304 | A | | 1/1979 | Bailey |
| 4,133,863 | A | | 1/1979 | Koenig |
| 4,150,089 | A | | 4/1979 | Linet |
| 4,154,229 | A | | 5/1979 | Nugent |
| 4,166,450 | A | | 9/1979 | Abramson |
| 4,190,426 | A | | 2/1980 | Ruschke |
| 4,193,400 | A | | 3/1980 | Loveless et al. |
| 4,202,764 | A | | 5/1980 | Afflerbaugh et al. |
| 4,206,282 | A | | 6/1980 | Hochstein |
| 4,207,870 | A | | 6/1980 | Eldridge |
| 4,210,173 | A | | 7/1980 | Choksi et al. |
| 4,212,308 | A | | 7/1980 | Percarpio |
| 4,226,236 | A | | 10/1980 | Genese |
| 4,238,207 | A | | 12/1980 | Ruschke |
| 4,257,416 | A | | 3/1981 | Prager |
| 4,275,730 | A | | 6/1981 | Hussein |
| 4,298,358 | A | | 11/1981 | Ruschke |
| 4,312,362 | A | | 1/1982 | Kaufman |
| 4,317,456 | A | | 3/1982 | Percarpio |
| 4,327,746 | A | * | 5/1982 | Feaster .................. A61B 5/154 600/577 |
| 4,340,067 | A | | 7/1982 | Rattenborg |
| 4,340,068 | A | | 7/1982 | Kaufman |
| 4,349,035 | A | | 9/1982 | Thomas et al. |
| 4,354,507 | A | | 10/1982 | Raitto |
| 4,370,987 | A | | 2/1983 | Bazell et al. |
| 4,373,535 | A | | 2/1983 | Martell |
| 4,398,544 | A | | 8/1983 | Nugent et al. |
| 4,411,275 | A | | 10/1983 | Raitto |
| 4,412,548 | A | | 11/1983 | Hoch |
| 4,416,290 | A | | 11/1983 | Lutkowski |
| 4,416,291 | A | | 11/1983 | Kaufman |
| 4,425,235 | A | | 1/1984 | Cornell et al. |
| 4,436,098 | A | | 3/1984 | Kaufman |
| 4,444,203 | A | | 4/1984 | Engelman |
| 4,459,997 | A | | 7/1984 | Sarstedt |
| 4,496,458 | A | | 1/1985 | Lee |
| 4,509,534 | A | | 4/1985 | Tassin, Jr. |
| 4,551,131 | A | | 11/1985 | Miles et al. |
| 4,581,014 | A | | 4/1986 | Millerd et al. |
| 4,608,996 | A | | 9/1986 | Brown |
| 4,626,248 | A | | 12/1986 | Scheller |
| 4,654,027 | A | | 3/1987 | Dragan et al. |
| 4,657,027 | A | | 4/1987 | Paulsen |
| 4,657,160 | A | | 4/1987 | Woods et al. |
| 4,673,386 | A | | 6/1987 | Gordon |
| 4,676,256 | A | | 6/1987 | Golden |
| 4,679,571 | A | | 7/1987 | Frankel et al. |
| 4,690,154 | A | | 9/1987 | Woodford et al. |
| 4,699,612 | A | | 10/1987 | Hamacher |
| 4,703,763 | A | | 11/1987 | McAlister et al. |
| 4,705,497 | A | | 11/1987 | Shitaokoshi et al. |
| 4,714,461 | A | | 12/1987 | Gabel |
| 4,715,854 | A | | 12/1987 | Vaillancourt |
| 4,772,273 | A | | 9/1988 | Alchas |
| 4,820,287 | A | | 4/1989 | Leonard |
| 4,838,855 | A | | 6/1989 | Lynn |
| 4,865,583 | A | | 9/1989 | Tu |
| 4,879,098 | A | | 11/1989 | Oberhardt et al. |
| 4,886,072 | A | | 12/1989 | Percarpio et al. |
| 4,890,627 | A | | 1/1990 | Haber et al. |
| 4,904,240 | A | | 2/1990 | Hoover |
| 4,936,315 | A | | 6/1990 | Lineback |
| 4,980,297 | A | | 12/1990 | Haynes et al. |
| 4,988,339 | A | | 1/1991 | Vadher |
| 5,009,847 | A | | 4/1991 | Solomons |
| 5,027,827 | A | | 7/1991 | Cody et al. |
| 5,032,116 | A | | 7/1991 | Peterson et al. |
| 5,032,288 | A | | 7/1991 | Columbus et al. |
| 5,035,688 | A | | 7/1991 | Inui |
| 5,045,185 | A | | 9/1991 | Ohnaka et al. |
| 5,052,403 | A | | 10/1991 | Haber et al. |
| 5,054,498 | A | | 10/1991 | Melet |
| 5,066,284 | A | | 11/1991 | Mersch et al. |
| 5,084,034 | A | | 1/1992 | Zanotti |
| 5,097,842 | A | | 3/1992 | Bonn |
| 5,100,394 | A | | 3/1992 | Dudar et al. |
| 5,108,927 | A | | 4/1992 | Dorn |

(56) References Cited

U.S. PATENT DOCUMENTS

| | | | |
|---|---|---|---|
| 5,116,323 | A | 5/1992 | Kreuzer et al. |
| 5,122,129 | A | 6/1992 | Olson et al. |
| 5,126,054 | A | 6/1992 | Matkovich |
| 5,135,489 | A | 8/1992 | Jepson et al. |
| 5,147,329 | A | 9/1992 | Brannon |
| 5,208,160 | A | 5/1993 | Kikyotani et al. |
| 5,222,502 | A | 6/1993 | Kurose |
| 5,269,317 | A | 12/1993 | Bennett |
| 5,286,279 | A | 2/1994 | Wu |
| 5,330,464 | A | 7/1994 | Mathias et al. |
| 5,334,162 | A | 8/1994 | Harris |
| 5,354,537 | A | 10/1994 | Moreno |
| 5,360,011 | A | 11/1994 | McCallister |
| 5,372,143 | A | 12/1994 | Bernes et al. |
| 5,395,339 | A | 3/1995 | Talonn et al. |
| 5,417,673 | A | 5/1995 | Gordon |
| 5,429,610 | A | 7/1995 | Vaillancourt |
| 5,431,811 | A | 7/1995 | Tusini et al. |
| 5,439,022 | A | 8/1995 | Summers et al. |
| 5,439,450 | A | 8/1995 | Haedt |
| 5,450,856 | A | 9/1995 | Norris |
| 5,451,321 | A | 9/1995 | Matkovich |
| 5,454,786 | A | 10/1995 | Harris |
| 5,466,228 | A | 11/1995 | Evans |
| 5,472,605 | A | 12/1995 | Zuk, Jr. |
| 5,485,854 | A | 1/1996 | Hollister |
| 5,507,299 | A | 4/1996 | Roland |
| 5,520,193 | A | 5/1996 | Suzuki et al. |
| 5,522,804 | A | 6/1996 | Lynn |
| 5,573,510 | A | 11/1996 | Isaacson |
| 5,573,951 | A | 11/1996 | Gombrich et al. |
| 5,575,777 | A | 11/1996 | Cover et al. |
| 5,577,513 | A | 11/1996 | Van Vlasselaer |
| 5,603,700 | A | 2/1997 | Daneshvar |
| 5,632,906 | A | 5/1997 | Ishida et al. |
| 5,634,893 | A | 6/1997 | Rishton |
| 5,649,912 | A | 7/1997 | Peterson |
| 5,658,271 | A | 8/1997 | Loubser |
| 5,685,846 | A | 11/1997 | Michaels, Jr. |
| 5,691,486 | A | 11/1997 | Behringer et al. |
| 5,749,857 | A | 5/1998 | Cuppy |
| 5,759,160 | A | 6/1998 | Neese et al. |
| 5,762,633 | A | 6/1998 | Whisson |
| 5,772,608 | A | 6/1998 | Dhas |
| 5,785,682 | A | 7/1998 | Grabenkort |
| 5,811,658 | A | 9/1998 | Van Driel et al. |
| 5,824,001 | A | 10/1998 | Erskine |
| 5,857,983 | A | 1/1999 | Douglas et al. |
| 5,865,803 | A | 2/1999 | Major |
| 5,865,812 | A | 2/1999 | Correia |
| 5,871,699 | A | 2/1999 | Ruggeri |
| 5,873,841 | A | 2/1999 | Brannon |
| 5,876,926 | A | 3/1999 | Beecham |
| 5,882,318 | A | 3/1999 | Boyde |
| D410,081 | S | 5/1999 | Sweeney et al. |
| 5,911,705 | A | 6/1999 | Howell |
| 5,922,551 | A | 7/1999 | Durbin et al. |
| RE36,273 | E | 8/1999 | Brannon |
| 5,947,932 | A | 9/1999 | Desecki et al. |
| 5,961,472 | A | 10/1999 | Swendson et al. |
| 5,971,956 | A | 10/1999 | Epstein |
| 5,980,830 | A | 11/1999 | Savage et al. |
| 6,001,307 | A | 12/1999 | Naka et al. |
| 6,010,633 | A | 1/2000 | Zuk, Jr. et al. |
| 6,013,037 | A | 1/2000 | Brannon |
| 6,016,712 | A | 1/2000 | Warden et al. |
| 6,050,957 | A | 4/2000 | Desch |
| 6,103,271 | A | 8/2000 | Morrison et al. |
| 6,106,509 | A | 8/2000 | Loubser |
| 6,126,643 | A | 10/2000 | Vaillancouert |
| 6,159,164 | A | 12/2000 | Neese et al. |
| 6,171,493 | B1 | 1/2001 | Zia et al. |
| 6,190,855 | B1 | 2/2001 | Herman et al. |
| 6,210,909 | B1 | 4/2001 | Guirguis |
| 6,224,561 | B1 | 5/2001 | Swendson et al. |
| 6,254,581 | B1 | 7/2001 | Scott |
| 6,296,020 | B1 | 10/2001 | McNeely et al. |
| 6,299,131 | B1 | 10/2001 | Ryan |
| 6,306,614 | B1 | 10/2001 | Romaschin et al. |
| 6,325,975 | B1 | 12/2001 | Naka et al. |
| 6,328,726 | B1 | 12/2001 | Ishida et al. |
| 6,355,023 | B1 | 3/2002 | Roth et al. |
| 6,364,847 | B1 | 4/2002 | Shulze et al. |
| 6,364,890 | B1 | 4/2002 | Lum et al. |
| 6,368,306 | B1 | 4/2002 | Koska |
| 6,387,086 | B2 | 5/2002 | Mathias et al. |
| 6,398,743 | B1 | 6/2002 | Halseth et al. |
| 6,403,381 | B1 | 6/2002 | Mann et al. |
| 6,440,725 | B1 | 8/2002 | Pourahmadi et al. |
| 6,478,775 | B1 | 11/2002 | Galt et al. |
| 6,482,188 | B1 | 11/2002 | Rogers et al. |
| 6,506,182 | B2 | 1/2003 | Estabrook et al. |
| 6,511,439 | B1 | 1/2003 | Tabata et al. |
| 6,520,948 | B1 | 2/2003 | Mathias et al. |
| 6,569,117 | B1 | 5/2003 | Ziv et al. |
| 6,592,555 | B1 | 7/2003 | Wen-Pi et al. |
| 6,592,613 | B1 | 7/2003 | Ishida et al. |
| 6,626,884 | B1 | 9/2003 | Dillon et al. |
| 6,629,959 | B2 | 10/2003 | Kuracina et al. |
| 6,638,252 | B2 | 10/2003 | Moulton et al. |
| 6,638,263 | B1 | 10/2003 | Theeuwes et al. |
| 6,648,835 | B1 | 11/2003 | Shemesh |
| 6,664,893 | B1 | 12/2003 | Eveland et al. |
| 6,692,479 | B2 | 2/2004 | Kraus et al. |
| 6,695,004 | B1 | 2/2004 | Raybuck |
| 6,712,963 | B2 | 3/2004 | Schick |
| 6,716,187 | B1 | 4/2004 | Jorgensen et al. |
| 6,716,396 | B1 | 4/2004 | Anderson et al. |
| 6,733,433 | B1 | 5/2004 | Fell |
| 6,736,783 | B2 | 5/2004 | Blake et al. |
| 6,746,420 | B1 | 6/2004 | Prestidge et al. |
| 6,772,513 | B1 | 8/2004 | Frye-Mason et al. |
| 6,843,775 | B2 | 1/2005 | Hyun |
| 6,860,871 | B2 | 3/2005 | Kuracina et al. |
| 6,905,483 | B2 | 6/2005 | Newby et al. |
| 6,913,580 | B2 | 7/2005 | Stone |
| 6,945,948 | B2 | 9/2005 | Bainbridge et al. |
| 6,979,323 | B2 | 12/2005 | Rogers et al. |
| 7,002,468 | B2 | 2/2006 | Eveland et al. |
| 7,044,941 | B2 | 5/2006 | Mathias et al. |
| 7,052,603 | B2 | 5/2006 | Schick |
| 7,055,401 | B2 | 6/2006 | Prybella et al. |
| 7,087,047 | B2 | 8/2006 | Kraus et al. |
| 7,141,097 | B2 | 11/2006 | Leahey |
| 7,241,281 | B2 | 7/2007 | Coelho et al. |
| 7,264,608 | B2 | 9/2007 | Bischof et al. |
| 7,306,736 | B2 | 12/2007 | Collins et al. |
| 7,314,452 | B2 | 1/2008 | Madonia |
| 7,316,662 | B2 | 1/2008 | Delnevo et al. |
| 7,335,188 | B2 | 2/2008 | Graf |
| 7,351,228 | B2 | 4/2008 | Keane et al. |
| 7,384,416 | B2 | 6/2008 | Goudaliez et al. |
| 7,435,231 | B2 | 10/2008 | Mathias et al. |
| 7,461,671 | B2 | 12/2008 | Ehwald et al. |
| 7,479,131 | B2 | 1/2009 | Mathias et al. |
| 7,544,324 | B2 | 6/2009 | Tung et al. |
| 7,614,857 | B2 | 11/2009 | Fuechslin et al. |
| 7,615,033 | B2 | 11/2009 | Leong |
| 7,618,407 | B2 | 11/2009 | Demay et al. |
| 7,648,491 | B2 | 1/2010 | Rogers |
| 7,666,166 | B1 | 2/2010 | Emmert et al. |
| 7,744,573 | B2 | 6/2010 | Gordon et al. |
| 7,766,879 | B2 | 8/2010 | Tan et al. |
| 7,896,817 | B2 | 3/2011 | Garrison |
| 7,914,508 | B2 | 3/2011 | Engstrom |
| 7,923,053 | B2 | 4/2011 | Kitching et al. |
| 7,963,950 | B2 | 6/2011 | Madonia |
| 8,070,725 | B2 | 12/2011 | Christensen |
| 8,109,157 | B2 | 2/2012 | Kanayama et al. |
| RE43,283 | E | 3/2012 | Ishida et al. |
| 8,197,420 | B2 | 6/2012 | Patton |
| 8,206,318 | B2 | 6/2012 | Uchiyama et al. |
| 8,231,546 | B2 | 7/2012 | Patton |
| 8,282,605 | B2 | 10/2012 | Tan et al. |

(56) References Cited

U.S. PATENT DOCUMENTS

| | | | |
|---|---|---|---|
| 8,287,499 | B2 | 10/2012 | Miyasaka |
| 8,337,418 | B2 | 12/2012 | Patton |
| 8,349,254 | B2 | 1/2013 | Hoshino et al. |
| 8,356,644 | B2 | 1/2013 | Chong et al. |
| 8,377,040 | B2 | 2/2013 | Burkholz et al. |
| 8,382,712 | B2 | 2/2013 | Kim |
| 8,383,044 | B2 | 2/2013 | Davis et al. |
| 8,412,300 | B2 | 4/2013 | Sonderegger |
| 8,523,826 | B2 | 9/2013 | Layton, Jr. |
| 8,535,241 | B2 | 9/2013 | Bullington et al. |
| 8,540,663 | B2 | 9/2013 | Davey et al. |
| 8,568,371 | B2 | 10/2013 | Siopes et al. |
| 8,574,203 | B2 | 11/2013 | Stout et al. |
| 8,603,009 | B2 | 12/2013 | Tan et al. |
| 8,647,286 | B2 | 2/2014 | Patton |
| 8,679,063 | B2 | 3/2014 | Stout et al. |
| 8,747,779 | B2 | 6/2014 | Sprague et al. |
| 8,772,046 | B2 | 7/2014 | Fraden et al. |
| 8,795,198 | B2 | 8/2014 | Tan et al. |
| 8,808,202 | B2 | 8/2014 | Brancazio |
| 8,827,958 | B2 | 9/2014 | Bierman et al. |
| 8,864,684 | B2 | 10/2014 | Bullington et al. |
| 8,876,734 | B2 | 11/2014 | Patton |
| 8,992,505 | B2 | 3/2015 | Thorne, Jr. et al. |
| 9,022,950 | B2 | 5/2015 | Bullington et al. |
| 9,022,951 | B2 | 5/2015 | Bullington et al. |
| 9,060,724 | B2 | 6/2015 | Bullington et al. |
| 9,060,725 | B2 | 6/2015 | Bullington et al. |
| 9,138,572 | B2 | 9/2015 | Zeytoonian et al. |
| 9,149,576 | B2 | 10/2015 | Bullington et al. |
| 9,155,495 | B2 | 10/2015 | Bullington et al. |
| 9,204,864 | B2 | 12/2015 | Bullington et al. |
| 9,205,198 | B2 | 12/2015 | Py |
| 9,233,208 | B2 | 1/2016 | Tekeste |
| RE45,896 | E | 2/2016 | Stout et al. |
| 9,314,201 | B2 | 4/2016 | Burkholz et al. |
| 9,320,459 | B2 | 4/2016 | Chin et al. |
| 9,820,682 | B2 | 11/2017 | Rogers et al. |
| 9,855,001 | B2 | 1/2018 | Patton |
| 9,855,002 | B2 | 1/2018 | Patton |
| 9,855,386 | B2 | 1/2018 | Close et al. |
| 9,861,306 | B2 | 1/2018 | Patton |
| 9,872,645 | B2 | 1/2018 | Patton |
| 9,877,674 | B2 | 1/2018 | Holmes et al. |
| 9,877,675 | B2 | 1/2018 | Baid |
| 9,895,092 | B2 | 2/2018 | Burkholz |
| 9,931,466 | B2 | 4/2018 | Bullington et al. |
| 9,950,084 | B2 | 4/2018 | Bullington et al. |
| 9,962,489 | B2 | 5/2018 | Hopkins |
| 9,999,383 | B2 | 6/2018 | Bullington et al. |
| 10,010,282 | B2 | 7/2018 | Rogers et al. |
| 10,022,079 | B2 | 7/2018 | Hopkins |
| 10,022,530 | B2 | 7/2018 | Tekeste |
| 10,028,687 | B2 | 7/2018 | Patton |
| 10,028,688 | B2 | 7/2018 | Patton |
| 10,028,689 | B2 | 7/2018 | Patton |
| 10,039,483 | B2 | 8/2018 | Bullington et al. |
| 10,045,724 | B2 | 8/2018 | Patton |
| 10,052,053 | B2 | 8/2018 | Patton |
| 10,080,516 | B2 | 9/2018 | Ellis et al. |
| 10,086,142 | B2 | 10/2018 | Tekeste |
| 10,143,412 | B2 | 12/2018 | Rogers et al. |
| 10,143,413 | B2 | 12/2018 | Garrett et al. |
| 10,206,613 | B2 | 2/2019 | Bullington et al. |
| 10,220,139 | B2 | 3/2019 | Bullington et al. |
| 10,238,326 | B2 | 3/2019 | Gil et al. |
| 10,251,590 | B2 | 4/2019 | Bullington et al. |
| 10,265,007 | B2 | 4/2019 | Bullington et al. |
| 10,292,633 | B2 | 5/2019 | Bullington et al. |
| 10,299,713 | B2 | 5/2019 | Patton |
| 10,369,285 | B2 | 8/2019 | Hopkins |
| 10,433,779 | B2 | 10/2019 | Bullington et al. |
| 10,463,792 | B2 | 11/2019 | Hopkins |
| 10,596,315 | B2 | 3/2020 | Bullington et al. |
| 10,624,977 | B2 | 4/2020 | Bullington et al. |
| 10,736,554 | B2 | 8/2020 | Bullington et al. |
| 10,772,548 | B2 | 9/2020 | Bullington et al. |
| 10,813,579 | B2 | 10/2020 | Baid |
| 10,827,964 | B2 | 11/2020 | Rogers et al. |
| 10,856,791 | B2 | 12/2020 | McHale et al. |
| 10,881,343 | B2 | 1/2021 | Bullington et al. |
| 10,888,262 | B2 | 1/2021 | Russ et al. |
| 10,912,506 | B2 | 2/2021 | Bullington et al. |
| 11,076,787 | B2 | 8/2021 | Bullington et al. |
| 11,116,904 | B2 | 9/2021 | Hopkins |
| 11,167,085 | B2 | 11/2021 | Hopkins |
| 11,234,626 | B2 | 2/2022 | Bullington et al. |
| 11,253,649 | B2 | 2/2022 | Hopkins |
| 11,259,727 | B2 | 3/2022 | Bullington et al. |
| 11,311,218 | B2 | 4/2022 | Bullington et al. |
| 11,317,838 | B2 | 5/2022 | Bullington et al. |
| 11,318,459 | B2 | 5/2022 | Shi et al. |
| 11,395,611 | B2 | 7/2022 | Bullington et al. |
| 11,395,612 | B2 | 7/2022 | Bullington et al. |
| 11,419,531 | B2 | 8/2022 | Bullington et al. |
| 11,529,081 | B2 | 12/2022 | Bullington et al. |
| 11,589,786 | B2 | 2/2023 | Bullington et al. |
| 11,607,159 | B2 | 3/2023 | Bullington et al. |
| 11,653,863 | B2 | 5/2023 | Bullington et al. |
| 11,660,030 | B2 | 5/2023 | Bullington et al. |
| 11,737,693 | B2 | 8/2023 | Bullington et al. |
| 11,786,155 | B2 | 10/2023 | Bullington et al. |
| 11,789,017 | B2 | 10/2023 | Bullington et al. |
| 11,819,329 | B2 | 11/2023 | Bullington et al. |
| 11,857,321 | B2 | 1/2024 | Bullington et al. |
| 11,890,452 | B2 | 2/2024 | Bullington et al. |
| 11,903,709 | B2 | 2/2024 | Bullington et al. |
| 11,903,710 | B2 | 2/2024 | Bullington et al. |
| 11,998,332 | B2 | 6/2024 | Bullington et al. |
| 12,083,234 | B2 | 9/2024 | Bullington et al. |
| 12,133,968 | B2 | 11/2024 | Bullington et al. |
| 12,138,052 | B1 | 11/2024 | Rogers et al. |
| 12,150,763 | B2 | 11/2024 | Bullington et al. |
| 12,186,080 | B2 | 1/2025 | Bullington et al. |
| 12,193,816 | B2 | 1/2025 | Bullington et al. |
| 12,290,363 | B2 | 5/2025 | Bullington et al. |
| 12,471,815 | B2 | 11/2025 | Bullington et al. |
| 12,471,816 | B2 | 11/2025 | Bullington et al. |
| 12,478,300 | B2 | 11/2025 | Bullington et al. |
| 12,478,301 | B2 | 11/2025 | Bullington et al. |
| 12,502,109 | B2 | 12/2025 | Bullington et al. |
| 12,551,150 | B2 | 2/2026 | Bullington et al. |
| 12,564,341 | B2 | 3/2026 | Bullington et al. |
| 12,575,772 | B2 | 3/2026 | Bullington et al. |
| 12,576,204 | B2 | 3/2026 | Bullington et al. |
| 2001/0031932 | A1 | 10/2001 | Blake et al. |
| 2001/0039058 | A1 | 11/2001 | Iheme et al. |
| 2002/0002349 | A1 | 1/2002 | Flaherty et al. |
| 2002/0004647 | A1 | 1/2002 | Leong |
| 2002/0107469 | A1 | 8/2002 | Bolan et al. |
| 2002/0183651 | A1 | 12/2002 | Hyun |
| 2002/0193751 | A1 | 12/2002 | Theeuwes et al. |
| 2003/0013991 | A1 | 1/2003 | Stone |
| 2003/0055381 | A1 | 3/2003 | Wilkinson |
| 2003/0069543 | A1 | 4/2003 | Carpenter et al. |
| 2003/0105414 | A1 | 6/2003 | Leong |
| 2003/0208151 | A1 | 11/2003 | Kraus et al. |
| 2004/0000309 | A1 | 1/2004 | Alston |
| 2004/0009542 | A1 | 1/2004 | Dumont et al. |
| 2004/0010228 | A1 | 1/2004 | Swenson et al. |
| 2004/0054283 | A1 | 3/2004 | Corey et al. |
| 2004/0054333 | A1 | 3/2004 | Theeuwes et al. |
| 2004/0124389 | A1 | 7/2004 | Phillips |
| 2004/0127816 | A1 | 7/2004 | Galvao |
| 2004/0147855 | A1 | 7/2004 | Marsden |
| 2005/0004524 | A1 | 1/2005 | Newby et al. |
| 2005/0010136 | A1 | 1/2005 | Restelli et al. |
| 2005/0054949 | A1 | 3/2005 | McKinnon et al. |
| 2005/0082218 | A1 | 4/2005 | Verri et al. |
| 2005/0148993 | A1 | 7/2005 | Mathias et al. |
| 2005/0154368 | A1 | 7/2005 | Lim et al. |
| 2005/0161112 | A1 | 7/2005 | Ehwald et al. |
| 2005/0199077 | A1 | 9/2005 | Prybella et al. |
| 2005/0240161 | A1 | 10/2005 | Crawford |

(56) References Cited

U.S. PATENT DOCUMENTS

| | | | | |
|---|---|---|---|---|
| 2005/0245885 | A1 | 11/2005 | Brown | |
| 2005/0273019 | A1 | 12/2005 | Conway et al. | |
| 2005/0277848 | A1 | 12/2005 | Graf | |
| 2005/0281713 | A1 | 12/2005 | Hampsch et al. | |
| 2006/0009713 | A1 | 1/2006 | Flaherty | |
| 2006/0018790 | A1 | 1/2006 | Naka et al. | |
| 2006/0111667 | A1 | 5/2006 | Matsuura et al. | |
| 2006/0155212 | A1 | 7/2006 | Madonia | |
| 2006/0251622 | A1 | 11/2006 | Suzuki et al. | |
| 2006/0287639 | A1 | 12/2006 | Sharp | |
| 2007/0083162 | A1 | 4/2007 | O'Reagan et al. | |
| 2007/0088279 | A1 | 4/2007 | Shue et al. | |
| 2007/0100250 | A1 | 5/2007 | Kline | |
| 2007/0119508 | A1 | 5/2007 | West et al. | |
| 2007/0172389 | A1 | 7/2007 | Wilding et al. | |
| 2007/0191716 | A1 | 8/2007 | Goldberger et al. | |
| 2007/0287948 | A1 | 12/2007 | Sakiewicz | |
| 2008/0086085 | A1 | 4/2008 | Brown | |
| 2008/0108954 | A1 | 5/2008 | Mathias et al. | |
| 2008/0114304 | A1 | 5/2008 | Nalesso et al. | |
| 2008/0145933 | A1 | 6/2008 | Patton | |
| 2008/0167577 | A1 | 7/2008 | Weilbacher et al. | |
| 2008/0185056 | A1 | 8/2008 | Diodati et al. | |
| 2008/0200837 | A1 | 8/2008 | Frazier et al. | |
| 2008/0254471 | A1 | 10/2008 | Bordano | |
| 2008/0255523 | A1 | 10/2008 | Grinberg | |
| 2008/0312576 | A1 | 12/2008 | McKinnon et al. | |
| 2008/0319346 | A1 | 12/2008 | Crawford et al. | |
| 2009/0050213 | A1 | 2/2009 | Biddell et al. | |
| 2009/0076441 | A1 | 3/2009 | Sebban | |
| 2009/0173685 | A1 | 7/2009 | Imai et al. | |
| 2009/0177117 | A1 | 7/2009 | Amano et al. | |
| 2009/0192447 | A1 | 7/2009 | Andersen et al. | |
| 2009/0215159 | A1 | 8/2009 | Kirby | |
| 2009/0227896 | A1 | 9/2009 | Alvin Tan et al. | |
| 2009/0301317 | A1 | 12/2009 | Andrews | |
| 2009/0306601 | A1 | 12/2009 | Shaw et al. | |
| 2010/0010372 | A1 | 1/2010 | Brown et al. | |
| 2010/0042048 | A1 | 2/2010 | Christensen | |
| 2010/0057004 | A1 | 3/2010 | Christensen et al. | |
| 2010/0094171 | A1 | 4/2010 | Conway et al. | |
| 2010/0152681 | A1 | 6/2010 | Mathias | |
| 2010/0185134 | A1 | 7/2010 | Houwen et al. | |
| 2010/0234768 | A1 | 9/2010 | Uchiyama et al. | |
| 2010/0240964 | A1 | 9/2010 | Sterling et al. | |
| 2010/0252118 | A1 | 10/2010 | Fraden et al. | |
| 2010/0255589 | A1 | 10/2010 | Saiki et al. | |
| 2010/0268118 | A1 | 10/2010 | Schweiger | |
| 2010/0286513 | A1 | 11/2010 | Pollard, Jr. et al. | |
| 2010/0298671 | A1 | 11/2010 | Asakura et al. | |
| 2011/0009717 | A1 | 1/2011 | Davis et al. | |
| 2011/0046602 | A1 | 2/2011 | Grimm et al. | |
| 2011/0092856 | A1 | 4/2011 | Freeman et al. | |
| 2011/0125058 | A1 | 5/2011 | Levinson et al. | |
| 2011/0178427 | A1 | 7/2011 | Tan et al. | |
| 2011/0198221 | A1 | 8/2011 | Angelescu | |
| 2011/0288441 | A1 | 11/2011 | Taguchi | |
| 2011/0306856 | A1 | 12/2011 | Rule et al. | |
| 2011/0306899 | A1 | 12/2011 | Brown et al. | |
| 2011/0313318 | A1 | 12/2011 | Rule et al. | |
| 2011/0319859 | A1 | 12/2011 | Zeytoonian et al. | |
| 2012/0004619 | A1 | 1/2012 | Stephens et al. | |
| 2012/0016266 | A1 | 1/2012 | Burkholz | |
| 2012/0017999 | A1 | 1/2012 | Velschow | |
| 2012/0022404 | A1 | 1/2012 | Fojtik | |
| 2012/0029494 | A1 | 2/2012 | Wittenberger et al. | |
| 2012/0035540 | A1 | 2/2012 | Ferren et al. | |
| 2012/0095367 | A1 | 4/2012 | Patton | |
| 2012/0123297 | A1 | 5/2012 | Brancazio | |
| 2012/0215131 | A1 | 8/2012 | Patton | |
| 2012/0226239 | A1 | 9/2012 | Green | |
| 2012/0245042 | A1 | 9/2012 | Liu et al. | |
| 2012/0265099 | A1 | 10/2012 | Goodnow, II et al. | |
| 2012/0265128 | A1 | 10/2012 | Kolln | |
| 2012/0277697 | A1 | 11/2012 | Haghgooie et al. | |
| 2012/0323142 | A1 | 12/2012 | Allen et al. | |
| 2013/0023792 | A1 | 1/2013 | Markey et al. | |
| 2013/0079604 | A1 | 3/2013 | Patton | |
| 2013/0085514 | A1 | 4/2013 | Lee et al. | |
| 2013/0116599 | A1 | 5/2013 | Bullington et al. | |
| 2013/0158506 | A1 | 6/2013 | Harris et al. | |
| 2013/0289420 | A1 | 10/2013 | Pfeiffer et al. | |
| 2013/0295602 | A1 | 11/2013 | Fowler et al. | |
| 2013/0317391 | A1 | 11/2013 | Bullington et al. | |
| 2014/0008366 | A1 | 1/2014 | Genosar | |
| 2014/0039348 | A1 | 2/2014 | Bullington et al. | |
| 2014/0051062 | A1 | 2/2014 | Vanapalli et al. | |
| 2014/0066880 | A1 | 3/2014 | Prince et al. | |
| 2014/0081172 | A1* | 3/2014 | Patton .............. | A61B 5/150343 600/576 |
| 2014/0107564 | A1 | 4/2014 | Bullington et al. | |
| 2014/0124542 | A1 | 5/2014 | Kojima et al. | |
| 2014/0128775 | A1 | 5/2014 | Andreae et al. | |
| 2014/0155781 | A1 | 6/2014 | Bullington et al. | |
| 2014/0155782 | A1 | 6/2014 | Bullington et al. | |
| 2014/0163419 | A1 | 6/2014 | Bullington et al. | |
| 2014/0188002 | A1 | 7/2014 | Close et al. | |
| 2014/0208978 | A1 | 7/2014 | Sunder et al. | |
| 2014/0221873 | A1 | 8/2014 | Hayakawa et al. | |
| 2014/0257249 | A1 | 9/2014 | Witt | |
| 2014/0276039 | A1 | 9/2014 | Cowan et al. | |
| 2014/0305196 | A1 | 10/2014 | Ellis et al. | |
| 2014/0336536 | A1 | 11/2014 | Brancazio | |
| 2015/0011847 | A1 | 1/2015 | Hayden | |
| 2015/0011910 | A1 | 1/2015 | Bullington et al. | |
| 2015/0011911 | A1 | 1/2015 | Bullington et al. | |
| 2015/0018715 | A1 | 1/2015 | Walterspiel | |
| 2015/0025454 | A1 | 1/2015 | Wetzel et al. | |
| 2015/0025455 | A1 | 1/2015 | Shetty et al. | |
| 2015/0025456 | A1 | 1/2015 | Shetty et al. | |
| 2015/0073304 | A1 | 3/2015 | Millerd | |
| 2015/0073348 | A1 | 3/2015 | Bullington et al. | |
| 2015/0094615 | A1 | 4/2015 | Patton | |
| 2015/0099996 | A1 | 4/2015 | Bullington et al. | |
| 2015/0151298 | A1 | 6/2015 | Hobbs et al. | |
| 2015/0257691 | A1 | 9/2015 | Bullington et al. | |
| 2015/0314105 | A1 | 11/2015 | Gasparyan et al. | |
| 2015/0342510 | A1 | 12/2015 | Bullington et al. | |
| 2015/0351678 | A1 | 12/2015 | Bullington et al. | |
| 2015/0351679 | A1 | 12/2015 | Bullington et al. | |
| 2015/0359473 | A1 | 12/2015 | Garrett et al. | |
| 2015/0367069 | A1 | 12/2015 | Bullington et al. | |
| 2016/0008579 | A1 | 1/2016 | Burkholz et al. | |
| 2016/0038068 | A1 | 2/2016 | Chickering, III et al. | |
| 2016/0038684 | A1 | 2/2016 | Lum et al. | |
| 2016/0081606 | A1 | 3/2016 | Russ et al. | |
| 2016/0089070 | A1 | 3/2016 | Russ et al. | |
| 2016/0113560 | A1 | 4/2016 | Bullington et al. | |
| 2016/0135724 | A1* | 5/2016 | Bullington ....... | A61B 5/150251 600/578 |
| 2016/0174888 | A1 | 6/2016 | Berthier et al. | |
| 2016/0174948 | A1 | 6/2016 | Kato et al. | |
| 2016/0213294 | A1 | 7/2016 | Patton | |
| 2016/0257586 | A1 | 9/2016 | Shaamsundarr | |
| 2016/0361006 | A1 | 12/2016 | Bullington et al. | |
| 2016/0367177 | A1 | 12/2016 | Edelhauser et al. | |
| 2017/0020427 | A1 | 1/2017 | Rogers et al. | |
| 2017/0020428 | A1 | 1/2017 | Rogers et al. | |
| 2017/0059552 | A1 | 3/2017 | Campton et al. | |
| 2017/0065733 | A1 | 3/2017 | Bullington et al. | |
| 2017/0071519 | A1 | 3/2017 | Gelfand et al. | |
| 2017/0150913 | A1 | 6/2017 | Patton | |
| 2017/0153165 | A1 | 6/2017 | Nwadigo | |
| 2017/0156654 | A1 | 6/2017 | Patton | |
| 2017/0172482 | A1 | 6/2017 | Patton | |
| 2017/0181683 | A1 | 6/2017 | Patton | |
| 2017/0227536 | A1 | 8/2017 | Matsuura | |
| 2017/0276679 | A1 | 9/2017 | Chapman et al. | |
| 2017/0327867 | A1 | 11/2017 | Dohale et al. | |
| 2017/0361019 | A1 | 12/2017 | Hopkins | |
| 2018/0078186 | A1 | 3/2018 | Patton | |
| 2018/0085042 | A1 | 3/2018 | Patton | |
| 2018/0092582 | A1 | 4/2018 | Patton | |
| 2018/0092583 | A1 | 4/2018 | Patton | |

(56) References Cited

U.S. PATENT DOCUMENTS

| | | | |
|---|---|---|---|
| 2018/0092584 | A1 | 4/2018 | Bullington et al. |
| 2018/0093077 | A1 | 4/2018 | Harding et al. |
| 2018/0098723 | A1 | 4/2018 | Patton |
| 2018/0116577 | A1 | 5/2018 | Bullington et al. |
| 2018/0160958 | A1 | 6/2018 | Baid |
| 2018/0177445 | A1 | 6/2018 | Rogers et al. |
| 2018/0177943 | A1 | 6/2018 | Bullington et al. |
| 2018/0207300 | A1 | 7/2018 | Bullington et al. |
| 2018/0242890 | A1 | 8/2018 | Chickering, III et al. |
| 2018/0271425 | A1 | 9/2018 | Rogers et al. |
| 2018/0289894 | A1 | 10/2018 | Hopkins |
| 2018/0321270 | A1 | 11/2018 | Iwashita et al. |
| 2018/0353117 | A1 | 12/2018 | Bullington et al. |
| 2019/0000367 | A1 | 1/2019 | Lundquist et al. |
| 2019/0030293 | A1 | 1/2019 | Rogers et al. |
| 2019/0049442 | A1 | 2/2019 | Guirguis |
| 2019/0076074 | A1 | 3/2019 | Bullington et al. |
| 2019/0150818 | A1 | 5/2019 | Bullington et al. |
| 2019/0151536 | A1 | 5/2019 | Bullington et al. |
| 2019/0159711 | A1 | 5/2019 | Rogers et al. |
| 2019/0175085 | A1 | 6/2019 | Bullington et al. |
| 2019/0175087 | A1 | 6/2019 | Bullington et al. |
| 2019/0209066 | A1 | 7/2019 | Bullington et al. |
| 2019/0365303 | A1 | 12/2019 | Bullington et al. |
| 2019/0374145 | A1 | 12/2019 | Breindel et al. |
| 2020/0060595 | A1 | 2/2020 | Bullington et al. |
| 2020/0060596 | A1 | 2/2020 | Patton |
| 2020/0197925 | A1 | 6/2020 | Ivosevic et al. |
| 2020/0214611 | A1 | 7/2020 | Ivosevic |
| 2020/0215211 | A1 | 7/2020 | Bullington et al. |
| 2020/0253524 | A1 | 8/2020 | Bullington et al. |
| 2020/0281514 | A1 | 9/2020 | Rogers et al. |
| 2020/0289039 | A1 | 9/2020 | Bullington et al. |
| 2020/0305780 | A1 | 10/2020 | Rogers et al. |
| 2020/0359951 | A1 | 11/2020 | Bullington et al. |
| 2021/0008280 | A1 | 1/2021 | Bullington et al. |
| 2021/0169387 | A1 | 6/2021 | Bullington et al. |
| 2021/0178389 | A1 | 6/2021 | Bullington et al. |
| 2021/0186392 | A1 | 6/2021 | Bullington et al. |
| 2021/0290123 | A1 | 9/2021 | Sawyer |
| 2021/0353193 | A1 | 11/2021 | Bullington et al. |
| 2021/0353194 | A1 | 11/2021 | Bullington et al. |
| 2021/0361206 | A1 | 11/2021 | Bullington et al. |
| 2021/0361207 | A1 | 11/2021 | Rogers et al. |
| 2022/0023539 | A1 | 1/2022 | Hopkins |
| 2022/0071533 | A1 | 3/2022 | Bullington et al. |
| 2022/0079482 | A1 | 3/2022 | Bullington et al. |
| 2022/0151525 | A1 | 5/2022 | Bullington et al. |
| 2022/0151526 | A1 | 5/2022 | Bullington et al. |
| 2022/0151527 | A1 | 5/2022 | Bullington et al. |
| 2022/0175284 | A1 | 6/2022 | Bullington et al. |
| 2022/0183600 | A1 | 6/2022 | Bullington et al. |
| 2022/0218248 | A1 | 7/2022 | Bullington et al. |
| 2022/0218249 | A1 | 7/2022 | Bullington et al. |
| 2022/0218250 | A1 | 7/2022 | Bullington et al. |
| 2022/0304600 | A1 | 9/2022 | Hammer |
| 2022/0304601 | A1 | 9/2022 | Bullington et al. |
| 2022/0304664 | A1 | 9/2022 | Hammer |
| 2022/0361786 | A1 | 11/2022 | Bullington et al. |
| 2022/0369970 | A1 | 11/2022 | Bullington et al. |
| 2022/0369971 | A1 | 11/2022 | Bullington et al. |
| 2022/0369972 | A1 | 11/2022 | Bullington et al. |
| 2023/0109255 | A1 | 4/2023 | Rogers et al. |
| 2023/0172502 | A1 | 6/2023 | Bullington et al. |
| 2023/0240571 | A1 | 8/2023 | Bullington et al. |
| 2023/0248281 | A1 | 8/2023 | Bullington et al. |
| 2023/0363674 | A1 | 11/2023 | Bullington et al. |
| 2023/0417746 | A1 | 12/2023 | Bullington et al. |
| 2024/0008780 | A1 | 1/2024 | Bullington et al. |
| 2024/0041369 | A1 | 2/2024 | Bullington et al. |
| 2024/0041370 | A1 | 2/2024 | Bullington et al. |
| 2024/0057908 | A1 | 2/2024 | Bullington et al. |
| 2024/0065590 | A1 | 2/2024 | Bullington et al. |
| 2024/0131258 | A1 | 4/2024 | Bullington et al. |
| 2024/0138734 | A1 | 5/2024 | Bullington et al. |
| 2024/0164670 | A1 | 5/2024 | Patton |
| 2024/0306963 | A1 | 9/2024 | Bullington et al. |
| 2024/0306964 | A1 | 9/2024 | Bullington et al. |
| 2024/0315620 | A1 | 9/2024 | Bullington et al. |
| 2024/0315621 | A1 | 9/2024 | Bullington et al. |
| 2024/0315622 | A1 | 9/2024 | Bullington et al. |
| 2024/0315623 | A1 | 9/2024 | Bullington et al. |
| 2024/0315624 | A1 | 9/2024 | Bullington et al. |
| 2025/0082235 | A1 | 3/2025 | Bullington et al. |
| 2025/0120628 | A1 | 4/2025 | Bullington et al. |
| 2025/0235133 | A1 | 7/2025 | Bullington et al. |
| 2025/0235613 | A1 | 7/2025 | Bullington et al. |
| 2025/0275697 | A1 | 9/2025 | Bullington et al. |
| 2026/0033759 | A1 | 2/2026 | Bullington et al. |

FOREIGN PATENT DOCUMENTS

| | | | |
|---|---|---|---|
| AU | 736156 | B2 | 7/2001 |
| AU | 2003244890 | A1 | 1/2004 |
| BR | 112012025546 | A2 | 6/2016 |
| CA | 1264275 | A | 1/1990 |
| CN | 86103696 | A | 1/1987 |
| CN | 2115767 | U | 9/1992 |
| CN | 1713928 | A | 12/2005 |
| CN | 1784186 | A | 6/2006 |
| CN | 1901955 | A | 1/2007 |
| CN | 2907683 | Y | 6/2007 |
| CN | 1325126 | C | 7/2007 |
| CN | 101060871 | A | 10/2007 |
| CN | 101309641 | A | 11/2008 |
| CN | 101352357 | A | 1/2009 |
| CN | 101437450 | A | 5/2009 |
| CN | 101564301 | A | 10/2009 |
| CN | 101631498 | A | 1/2010 |
| CN | 101676001 | A | 3/2010 |
| CN | 101785676 | A | 7/2010 |
| CN | 101801445 | A | 8/2010 |
| CN | 201617841 | U | 11/2010 |
| CN | 102421362 | A | 4/2012 |
| CN | 102548524 | A | 7/2012 |
| CN | 102811754 | A | 12/2012 |
| CN | 102971040 | A | 3/2013 |
| CN | 103027727 | A | 4/2013 |
| CN | 101626803 | B | 8/2013 |
| CN | 103477201 | A | 12/2013 |
| CN | 103619386 | A | 3/2014 |
| CN | 104971390 | A | 10/2015 |
| CN | 105090005 | A | 11/2015 |
| CN | 105612346 | A | 5/2016 |
| CN | 105813669 | A | 7/2016 |
| CN | 107735901 | A | 2/2018 |
| CN | 209916854 | U | 1/2020 |
| CN | 111771054 | A | 10/2020 |
| DE | 7203008 | U | 5/1972 |
| DE | 2203858 | A1 | 5/1973 |
| DE | 2541494 | A1 | 3/1977 |
| DE | 2203858 | B2 | 10/1977 |
| DE | 2946660 | A1 | 5/1981 |
| DE | 3403957 | A1 | 8/1985 |
| DE | 4026732 | A1 | 2/1992 |
| DE | 29913417 | U1 | 12/2000 |
| DE | 10038026 | A1 | 2/2001 |
| DE | 10134913 | A1 | 2/2003 |
| DE | 10134913 | C2 | 6/2003 |
| DE | 10243129 | A1 | 4/2004 |
| DE | 69632870 | T2 | 7/2005 |
| DE | 102009057792 | B4 | 8/2016 |
| EP | 0181957 | A1 | 5/1986 |
| EP | 0207304 | A1 | 1/1987 |
| EP | 0448795 | A2 | 10/1991 |
| EP | 0208053 | B1 | 12/1991 |
| EP | 0329786 | B1 | 1/1993 |
| EP | 0486059 | B1 | 1/1997 |
| EP | 1144026 | B1 | 7/2004 |
| EP | 1505159 | B1 | 5/2008 |
| EP | 1980204 | A1 | 10/2008 |
| EP | 2254472 | A2 | 12/2010 |
| EP | 1381438 | B1 | 5/2012 |
| EP | 2254472 | B1 | 5/2016 |

(56) References Cited

FOREIGN PATENT DOCUMENTS

| | | | |
|---|---|---|---|
| EP | 1487369 | B1 | 5/2017 |
| EP | 2986218 | B1 | 12/2017 |
| EP | 2178585 | B1 | 4/2021 |
| EP | 3721086 | A4 | 11/2021 |
| ES | 2564496 | T3 | 3/2016 |
| FR | 2110516 | A5 | 6/1972 |
| FR | 2691364 | B1 | 8/1999 |
| FR | 2833175 | B1 | 5/2004 |
| FR | 2851167 | B1 | 10/2005 |
| GB | 1506449 | A | 4/1978 |
| GB | 1562686 | A | 3/1980 |
| IE | 904353 | A1 | 10/1991 |
| IL | 128709 | A | 9/2004 |
| JP | S4846180 | A | 7/1973 |
| JP | S5397289 | A | 8/1978 |
| JP | S56109643 | A | 8/1981 |
| JP | S5789869 | A | 6/1982 |
| JP | S6458241 | A | 3/1989 |
| JP | H0363570 | A | 3/1991 |
| JP | H05501071 | A | 3/1993 |
| JP | H0551222 | B2 | 8/1993 |
| JP | H06500403 | A | 1/1994 |
| JP | H0716219 | A | 1/1995 |
| JP | H0910302 | A | 1/1997 |
| JP | H0951947 | A | 2/1997 |
| JP | H09229828 | A | 9/1997 |
| JP | H10153531 | A | 6/1998 |
| JP | H10211274 | A | 8/1998 |
| JP | H1156821 | A | 3/1999 |
| JP | H1176397 | A | 3/1999 |
| JP | H11197236 | A | 7/1999 |
| JP | 2001159630 | A | 6/2001 |
| JP | 2001161668 | A | 6/2001 |
| JP | 2001276181 | A | 10/2001 |
| JP | 3231086 | B2 | 11/2001 |
| JP | 2002116201 | A | 4/2002 |
| JP | 2002272710 | A | 9/2002 |
| JP | 2002528159 | A | 9/2002 |
| JP | 2003126068 | A | 5/2003 |
| JP | 2005237617 | A | 9/2005 |
| JP | 2006026327 | A | 2/2006 |
| JP | 3813974 | B2 | 8/2006 |
| JP | 2007175534 | A | 7/2007 |
| JP | 2008149076 | A | 7/2008 |
| JP | 2008206734 | A | 9/2008 |
| JP | 2009525819 | A | 7/2009 |
| JP | 2009536554 | A | 10/2009 |
| JP | 4382322 | B2 | 12/2009 |
| JP | 2010514501 | A | 5/2010 |
| JP | 2010524505 | A | 7/2010 |
| JP | 2010189415 | A | 9/2010 |
| JP | 4573538 | B2 | 11/2010 |
| JP | 2010536014 | A | 11/2010 |
| JP | 2011512987 | A | 4/2011 |
| JP | 4861649 | B2 | 1/2012 |
| JP | 4869910 | B2 | 2/2012 |
| JP | 5344252 | B2 | 11/2013 |
| JP | 5620541 | B2 | 11/2014 |
| JP | 2016500278 | A | 1/2016 |
| JP | 2016523591 | A | 8/2016 |
| JP | 5997760 | B2 | 9/2016 |
| JP | 2016527939 | A | 9/2016 |
| JP | 6194415 | B2 | 9/2017 |
| JP | 2018525191 | A | 9/2018 |
| JP | 2020513906 | A | 5/2020 |
| KR | 20120030087 | A | 3/2012 |
| KR | 101134279 | B1 | 4/2012 |
| KR | 20160088853 | A | 7/2016 |
| TW | 200528066 | A | 9/2005 |
| WO | WO-1984003213 | A1 | 8/1984 |
| WO | WO-8605568 | A1 | 9/1986 |
| WO | WO-9004351 | A1 | 5/1990 |
| WO | WO-9118632 | A1 | 12/1991 |
| WO | WO-9216144 | A1 | 10/1992 |
| WO | WO-1994007415 | A1 | 4/1994 |
| WO | WO-1994012093 | A1 | 6/1994 |
| WO | WO-1994015665 | A1 | 7/1994 |
| WO | WO-1995011712 | A1 | 5/1995 |
| WO | WO-9516395 | A1 | 6/1995 |
| WO | WO-1995021639 | A1 | 8/1995 |
| WO | WO-1995024176 | A1 | 9/1995 |
| WO | WO-1996021853 | A1 | 7/1996 |
| WO | WO-9718845 | A1 | 5/1997 |
| WO | WO-1997045714 | A1 | 12/1997 |
| WO | WO-1998034532 | A1 | 8/1998 |
| WO | WO-9846136 | A1 | 10/1998 |
| WO | WO-9913925 | A1 | 3/1999 |
| WO | WO-1999029232 | A1 | 6/1999 |
| WO | WO-9948425 | A1 | 9/1999 |
| WO | WO-9955232 | A1 | 11/1999 |
| WO | WO-2000024313 | A1 | 5/2000 |
| WO | WO-0040291 | A1 | 7/2000 |
| WO | WO-0041624 | A1 | 7/2000 |
| WO | WO-0108546 | A2 | 2/2001 |
| WO | WO-0191829 | A2 | 12/2001 |
| WO | WO-2002028457 | A1 | 4/2002 |
| WO | WO-2002045813 | A1 | 6/2002 |
| WO | WO-02051520 | A1 | 7/2002 |
| WO | WO-03008012 | A2 | 1/2003 |
| WO | WO-2003041767 | A1 | 5/2003 |
| WO | WO-03047660 | A1 | 6/2003 |
| WO | WO-03078964 | A2 | 9/2003 |
| WO | WO-2003085395 | A1 | 10/2003 |
| WO | WO-2003092573 | A2 | 11/2003 |
| WO | WO-2004082467 | A2 | 9/2004 |
| WO | WO-2004103565 | A2 | 12/2004 |
| WO | WO-2005068011 | A1 | 7/2005 |
| WO | WO-2006031500 | A2 | 3/2006 |
| WO | WO-2006124634 | A1 | 11/2006 |
| WO | WO-2007033319 | A1 | 3/2007 |
| WO | WO-2008028165 | A2 | 3/2008 |
| WO | WO-2008047699 | A1 | 4/2008 |
| WO | WO-2008077047 | A2 | 6/2008 |
| WO | WO-2008101025 | A1 | 8/2008 |
| WO | WO-2008157511 | A1 | 12/2008 |
| WO | WO-2009094345 | A1 | 7/2009 |
| WO | WO-2009113999 | A2 | 9/2009 |
| WO | WO-2010087216 | A1 | 8/2010 |
| WO | WO-2011030282 | A1 | 3/2011 |
| WO | WO-2011050110 | A1 | 4/2011 |
| WO | WO-2011069145 | A2 | 6/2011 |
| WO | WO-2011114413 | A1 | 9/2011 |
| WO | WO-2011123685 | A2 | 10/2011 |
| WO | WO-2011162772 | A1 | 12/2011 |
| WO | WO-2012012127 | A2 | 1/2012 |
| WO | WO-2012114105 | A1 | 8/2012 |
| WO | WO-2013181352 | A1 | 12/2013 |
| WO | WO-2014022275 | A1 | 2/2014 |
| WO | WO-2014022750 | A1 | 2/2014 |
| WO | WO-2014058945 | A1 | 4/2014 |
| WO | WO-2014085800 | A1 | 6/2014 |
| WO | WO-2014089186 | A1 | 6/2014 |
| WO | WO-2014099266 | A2 | 6/2014 |
| WO | WO-2015091818 | A1 | 6/2015 |
| WO | WO-2016027782 | A1 | 2/2016 |
| WO | WO-2016054252 | A1 | 4/2016 |
| WO | WO-2016201406 | A1 | 12/2016 |
| WO | WO-2017019552 | A1 | 2/2017 |
| WO | WO-2017041087 | A1 | 3/2017 |
| WO | WO-2017133953 | A1 | 8/2017 |
| WO | WO-2017218840 | A1 | 12/2017 |
| WO | WO-2017218848 | A1 | 12/2017 |
| WO | WO-2018125929 | A1 | 7/2018 |
| WO | WO-2018227191 | A1 | 12/2018 |
| WO | WO-2019055487 | A1 | 3/2019 |
| WO | WO-2019113505 | A1 | 6/2019 |
| WO | WO-2019232196 | A1 | 12/2019 |
| WO | WO-2020163744 | A1 | 8/2020 |
| WO | WO-2020185914 | A1 | 9/2020 |
| WO | WO-2021119487 | A1 | 6/2021 |
| WO | WO-2022203747 | A1 | 9/2022 |

(56) References Cited

OTHER PUBLICATIONS

Barnard, D. R. & Arthur, M. M., "Fibronectin (cold insoluble globulin) in the neonate," Clinical and Laboratory Observations, 102(3): 453-455 (1983).
Baxter, "IV Tubing and Access Devices" authored by and published by Baxter, dated Nov. 6, 2006, 105 pages.
BD Saf-T-Intima Closed IV Catheter System, Becton, Dickinson and Company, 2015 Brochure. Retrieved from the Internet (Sep. 11, 2019) https://www.bd.com/en-us/offerings/capabilities/infusion-therapy/iv-catheters/bd-saf-tintima-closed-iv-catheter-system, 2 pages.
BD Vacutainer Passive Shielding Blood Collection Needle Brochure; Becton Dickinson and Company (2005), 2 pages.
Brecher, M. E. et al., "Bacterial Contamination of Blood Components," Clinical Microbiology Reviews, 18(1):195-204 (2005).
Calam, R. R., "Recommended 'Order of Draw' for Collecting Blood Specimens Into Additive-Containing Tubes," Letter to the Editor, Clinical Chemistry, 28(6):1399 (1982), 1 page.
Cartridge and Test Information, Abbott, Art: 714258-010 Rev. Date: Aug. 15- 16, 6 pages.
Challiner, A. et al., Queen Alexandra Hospital, Portsmouth P06 3LY, "Venous/arterial blood management protection system," Correspondence, 1992, p. 169.
De Korte, D. et al., "Diversion of first blood volume results in a reduction of bacterial contamination for whole-blood collections," Vox Sanguinis, 83:13-16 (2002).
De Korte, D. et al., "Effects of skin disinfection method, deviation bag, and bacterial screening on clinical safety of platelet transfusions in the Netherlands," Transfusion, 46: 476-485 (2006).
Edwards Lifesciences, "Conservation. Safety. Simplicity. Edwards VAMP and VAMP Jr. Systems," 2002 Brochure. Retrieved from the Internet (Sep. 11, 2019) https://www.medline.com/media/catalog/Docs/MKT/VAMPSYSTEMBROCHURE.PDF, 4 pages.
Ernst, D. J. et al., "NCCLS simplifies the order of draw: a brief history," MLO, 26-27 (2004).
Exhibit 01—Defendant's Invalidity Contentions, Invalidity Claim Chart—U.S. Pat. No. 9,855,001 vs Barnard NPL, Aug. 30, 2019, 8 pages.
Exhibit 02—Defendant's Invalidity Contentions, Invalidity Claim Chart—U.S. Pat. No. 9,855,001 vs BD Needle NPL, Aug. 30, 2019, 7 pages.
Exhibit 03—Defendant's Invalidity Contentions, Invalidity Claim Chart—U.S. Pat. No. 9,855,001 vs U.S. Pat. No. 6,626,884, Aug. 30, 2019, 11 pages.
Exhibit 04—Defendant's Invalidity Contentions, Invalidity Claim Chart—U.S. Pat. No. 9,855,001 vs U.S. Pat. Pub. No. 2005/161112, Aug. 30, 2019,22 pages.
Exhibit 05—Defendant's Invalidity Contentions, Invalidity Claim Chart—U.S. Pat. No. 9,855,001 vs U.S. Pat. No. 4,673,386, Aug. 30, 2019, 21 pages.
Exhibit 06—Defendant's Invalidity Contentions, Invalidity Claim Chart—U.S. Pat. No. 9,855,001 vs U.S. Pat. No. 4,904,240, Aug. 30, 2019, 15 pages.
Exhibit 07—Defendant's Invalidity Contentions, Invalidity Claim Chart—U.S. Pat. No. 9,855,001 vs Leukotrap NPL, Aug. 30, 2019, 38 pages.
Exhibit 09—Defendant's Invalidity Contentions, Invalidity Claim Chart—U.S. Pat. No. 9,855,001 vs U.S. Pat. No. 4,106,497, Aug. 30, 2019, 22 pages.
Exhibit 10—Defendant's Invalidity Contentions, Invalidity Claim Chart—U.S. Pat. No. 9,855,001 vs Stopcock-Syringe NPL, Aug. 30, 2019, 85 pages.
Exhibit 11—Defendant's Invalidity Contentions, Invalidity Claim Chart—U.S. Pat. No. 9,855,001 vs Ziegler NPL, Aug. 30, 2019, 8 pages.
Exhibit 12—Defendant's Invalidity Contentions, Invalidity Claim Chart—U.S. Pat. No. 10,028,689 vs Barnard NPL, Aug. 30, 2019, 12 pages.
Exhibit 13—Defendant's Invalidity Contentions, Invalidity Claim Chart—U.S. Pat. No. 10,028,689 vs U.S. Pat. No. 6,626,884, Aug. 30, 2019, 29 pages.
Exhibit 14—Defendant's Invalidity Contentions, Invalidity Claim Chart—U.S. Pat. No. 10,028,689 vs U.S. Pat. Pub. No. 2005/161112, Aug. 30, 2019,48 pages.
Exhibit 15—Defendant's Invalidity Contentions, Invalidity Claim Chart—U.S. Pat. No. 10,028,689 vs U.S. Pat. No. 4,673,386, Aug. 30, 2019, 44 pages.
Exhibit 16—Defendant's Invalidity Contentions, Invalidity Claim Chart—U.S. Pat. No. 10,028,689 vs U.S. Pat. No. 4,904,240, Aug. 30, 2019, 31 pages.
Exhibit 17—Defendant's Invalidity Contentions, Invalidity Claim Chart—U.S. Pat. No. 10,028,689 vs Leukotrap NPL, Aug. 30, 2019, 113 pages.
Exhibit 19—Defendant's Invalidity Contentions, Invalidity Claim Chart—U.S. Pat. No. 10,028,689 vs U.S. Pat. No. 4, 106,497, Aug. 30, 2019, 38 pages.
Exhibit 20—Defendant's Invalidity Contentions, Invalidity Claim Chart—U.S. Pat. No. 10,028,689 vs Stopcock-Syringe NPL, Aug. 30, 2019, 268 pages.
Exhibit 21—Defendant's Invalidity Contentions, Invalidity Claim Chart—U.S. Pat. No. 10,220,139 vs U.S. Pat. No. 6,626,884, Aug. 30, 2019, 35 pages.
Exhibit 22—Defendant's Invalidity Contentions, Invalidity Claim Chart—U.S. Pat. No. 10,220,139 vs U.S. Pat. Pub. No. 2005/161112, Aug. 30, 2019,46 pages.
Exhibit 23—Defendant's Invalidity Contentions, Invalidity Claim Chart—U.S. Pat. No. 10,220,139 vs U.S. Pat. No. 4,207,870, Aug. 30, 2019, 20 pages.
Exhibit 24—Defendant's Invalidity Contentions, Invalidity Claim Chart—U.S. Pat. No. 10,220,139 vs U.S. Pat. No. 6,506,182, Aug. 30, 2019, 15 pages.
Exhibit 25—Defendant's Invalidity Contentions, Invalidity Claim Chart—U.S. Pat. No. 10,220,139 vs U.S. Pat. No. 4,673,386, Aug. 30, 2019, 53 pages.
Exhibit 26—Defendant's Invalidity Contentions, Invalidity Claim Chart—U.S. Pat. No. 10,220,139 vs U.S. Pat. No. 4,904,240, Aug. 30, 2019, 39 pages.
Exhibit 27—Defendant's Invalidity Contentions, Invalidity Claim Chart—U.S. Pat. No. 10,220,139 vs Leukotrap NPL, Aug. 30, 2019, 115 pages.
Exhibit 29—Defendant's Invalidity Contentions, Invalidity Claim Chart—U.S. Pat. No. 10,220,139 vs U.S. Pat. No. 4,106,497, Aug. 30, 2019, 45 pages.
Exhibit 30—Defendant's Invalidity Contentions, Invalidity Claim Chart—U.S. Pat. No. 10,220,139 vs Stopcock-Syringe NPL, Aug. 30, 2019, 246 pages.
Exhibit 31—Defendant's Invalidity Contentions, Invalidity Claim Chart—U.S. Pat. No. 10,220,139 vs U.S. Pat. No. 4,349,035, Aug. 30, 2019, 26 pages.
Exhibit 32—Defendant's Invalidity Contentions, Invalidity Claim Chart—U.S. Pat. No. 10,220,139 vs U.S. Pat. Pub. No. 2008/0145933A1, Aug. 30, 2019, 39 pages.
Exhibit 33—Defendant's Invalidity Contentions, Invalidity Claim Chart—U.S. Pat. No. 10,039,483 vs Barnard NPL, Aug. 30, 2019, 14 pages.
Exhibit 34—Defendant's Invalidity Contentions, Invalidity Claim Chart—U.S. Pat. No. 10,039,483 vs U.S. Pat. No. 6,626,884, Aug. 30, 2019, 22 pages.
Exhibit 35—Defendant's Invalidity Contentions, Invalidity Claim Chart—U.S. Pat. No. 10,039,483 vs U.S. Pat. Pub. No. 2005/161112, Aug. 30, 2019,45 pages.
Exhibit 36—Defendant's Invalidity Contentions, Invalidity Claim Chart—U.S. Pat. No. 10,039,483 vs U.S. Pat. No. 4,673,386, Aug. 30, 2019, 47 pages.
Exhibit 37—Defendant's Invalidity Contentions, Invalidity Claim Chart—U.S. Pat. No. 10,039,483 vs U.S. Pat. No. 4,904,240, Aug. 30, 2019, 30 pages.
Exhibit 38—Defendant's Invalidity Contentions, Invalidity Claim Chart—U.S. Pat. No. 10,039,483 vs Leukotrap NPL, Aug. 30, 2019, 115 pages.

(56) References Cited

OTHER PUBLICATIONS

Exhibit 40—Defendant's Invalidity Contentions, Invalidity Claim Chart—U.S. Pat. No. 10,039,483 vs U.S. Pat. No. 4,106,497, Aug. 30, 2019, 45 pages.
Exhibit 41—Defendant's Invalidity Contentions, Invalidity Claim Chart—U.S. Pat. No. 10,039,483 vs Stopcock-Syringe NPL, Aug. 30, 2019, 214 pages.
Exhibit 42—Defendant's Invalidity Contentions, Invalidity Claim Chart—U.S. Pat. No. 10,039,483 vs U.S. Pat. Pub. No. 2008/0145933A1, Aug. 30, 2019, 38 pages.
Extended European Search Report for European Application No. 18885543.1, dated Oct. 8, 2021, 8 pages.
Gottlieb, T., "Hazards of Bacterial Contamination of Blood Products," Anaesth Intens Care, 21: 20-23 (1993).
Hall, K. K. et al., "Updated Review of Blood Culture Contamination," Clinical Microbiology Reviews, 19(4):788-802 (2006).
Hillyer, C. D. et al., "Bacterial Contamination of Blood Components Risks, Strategies, and Regulation," Hematology, 575-589 (2003).
International Search Report and Written Opinion for International Application No. PCT/US2018/064561, dated Feb. 11, 2019, 9 pages.
Japanese Office Action for Application No. JP20200550048 dated Aug. 5, 2022, 5 pages.
Kim, J. Y. et al., "The Sum of the Parts is Greater Than the Whole: Reducing Blood Culture Contamination," Annals of Internal Medicine, 154:202-203 (2011).
Levin, P. D. et al., "Use of the Nonwire Central Line Hub to Reduce Blood Culture Contamination," Chest, 143(3):640-645 (2013).
Liumbruno, G. M. et al., "Reduction of the risk of bacterial contamination of blood components through diversion of the first part of the donation of blood and blood components," Blood Transfus, 7: 86-93 (2009).
Li, Y. et al., "Direct labeling and visualization of blood vessels with lipophilic carbocyanine dye Oil," Nature Protocols, 3(11): 1703-1708 (2008).
Mayer, G. A, "A Method for the Reliable Determination of Clotting Time in Whole Blood," Can Med Assoc J., 72(12): 927-929 (1955).
McDonald, C. P., "Interventions Implemented to Reduce the Risk of Transmission of Bacteria by Transfusion in the English National Blood Service," Transfus Med Hemother, 38:255-258 (2011).
Meissner, G. F. et al., "A Method Based on the Use of Whole Venous Blood in Capillary Tubes," American Journal of Clinical Pathology, 33(2): 29-31 (1963).
Murphy, M., "Better Blood Transfusion," Journal of the Intensive Core Society, 4(3): 78-80 (2003).
Napolitano, M. et al., "Quality control of bacterial contamination of blood components: the feasibility of diversion system testing," Blood Transfus, 2: 231-232 (2004).
Norberg, A et al., "Contamination Rates of Blood Cultures Obtained by Dedicated Phlebotomy vs Intravenous Catheter," JAMA, 289(6): 726-729 (2003).
Notification of the Second Office Action for Chinese Application No. 201880088771.7, dated May 7, 2022, 9 pages, with English translation.
Office Action for U.S. Appl. No. 16/213,005, dated Feb. 3, 2021, 15 pages.
Office Action issued by Chinese Patent Office for Application No. 201880088771.7, dated Sep. 3, 2021, 17 pages—English translation available.
Order of Draw for Multiple Tube Collections, LabNotes, a newsletter from BD Diagnostics,—Preanalytical Systems, 17(1):3 (2007).
Page, C. et al., "Blood conservation devices in critical care: a narrative review," Annals of Intensive Care, 3:14 (2013), 6 pages.
Palavecino, E. L. et al., "Detecting Bacterial Contamination in Platelet Products," Clin. Lab., 52:443-456 (2006).
Pall Corp., "Leukotrap Filtration Systems for Whole Blood Derived Platelets: Leukotrap RC PL and Leukotrap PL Systems," 2005 Brochure, 2 pages.
Patton, R. G. et al., "Innovation for Reducing Blood Culture Contamination: Initial Specimen Diversion Technique," Journal of Clinical Microbiology, 48(12):4501-4503 (2010).
Perez, P. et al., "Multivariate analysis of determinants of bacterial contamination of whole-blood donations," Vox Sanguinis, 82:55-60 (2002).
Proehl, J. A et al., "Clinical Practice Guideline: Prevention of Blood Culture Contamination, Full Version," 2012 ENA Emergency Nurses Resources Development Committee, Emergency Nurses Association (Dec. 2012), 14 pages.
Quilici, N. et al., "Differential Quantitative Blood Cultures in the Diagnosis of Catheter-Related Sepsis in Intensive Care Units," Clinical Infectious Diseases 25:1066-1070 (1997).
Schuur, J., "Blood Cultures: When Do they Help and When Do They Harm?" Brigham & Women's Hospital, Department of Emergency Medicine, (Jun. 21-23, 2012), 42 pages.
Sheppard, C. A et al., "Bacterial Contamination of Platelets for Transfusion: Recent Advances and Issues," LabMedicine, 36(12):767-770 (2005).
Shulman, G., "Quality of Processed Blood for Autotransfusion," The Journal of Extra-Corporeal Technology, 32(1): 11-19 (2000).
Sibley, C. D. et al., "Molecular Methods for Pathogen and Microbial Community Detection and Characterization: Current and Potential Application in Diagnostic Microbiology," Infection, Genetics and Evolution 12:505-521 (2012).
Stohl, S. et al., "Blood Cultures at Central Line Insertion in the Intensive Care Unit: Comparison with Peripheral Venipuncture," Journal of Clinical Microbiology, 49(7):2398-2403 (2011).
Tang, M. et al., "Closed Blood Conservation Device for Reducing Catheter-Related Infections in Children After Cardiac Surgery," Critical Care Nurse, 34(5): 53-61 (2014).
Wagner et al., "Diversion of Initial Blood Flow to Prevent Whole-Blood Contamination by Skin Surface Bacteria: an in vitro model," Transfusion, 40:335-338 (2000).
Wang, P. et al., "Strategies on Reducing Blood Culture Contamination," Reviews in Medical Microbiology, 23:63-66 (2012).
Weinbaum, F. I. et al., "Doing It Right the First Time: Quality Improvement and the Contaminant Blood Culture," Journal of Clinical Microbiology, 35(3): 563-565 (1997).
Weinstein, M.P., "Current Blood Culture Methods and Systems: Clinical Concepts, Technology, and Interpretation of Results," Clinical Infectious Diseases, 23: 40-46 (1996).
Weinstein, M.P. et al., "The Clinical Significance of Positive Blood Cultures in the 1990s: A Prospective Comprehensive Evaluation of the Microbiology, Epidemiology, and Outcome of Bacteremia and Fungemia in Adults," Clinical Infectious Diseases, 24:584-602 (1997).
Weinstein, M.P., "Minireview: Blood Culture Contamination: Persisting Problems and Partial Progress," Journal of Clinical Microbiology, 41(6): 2275-2278 (2003).
Ziegler, et al., "Controlled Clinical Laboratory Comparison of Two Supplemented Aerobic and Anaerobic Media Used in Automated Blood Culture Systems To Detect Bloodstream Infections," J. Clinical Microbiology, 36(3):657-661 (1998).
Zimmon, D. S. et al., "Effect of Portal Venous Blood Flow Diversion on Portal Pressure," J Clin Invest, 65(6): 1388-1397 (1980).
Zundert, A V., "New Closed IV Catheter System," Acta Anaesth. Belg., 56: 283-285 (2005).
Arenas et al., "Asynchronous Testing of 2 Specimen-Diversion Devices to Reduce Blood Culture Contamination: A Single-Site Product Supply Quality Improvement Project," Journal of Emergency Nursing, 47(2):256-264, e6, (Mar. 2021; Epub Jan. 8, 2021).
AU Application No. 2013267448, Office Action mailed Nov. 5, 2016; Applicant Magnolia Medical Technologies, Inc.; 3 pages.
AU Application No. 2017216493, Office Action mailed Sep. 19, 2018; Applicant Magnolia Medical Technologies, Inc.; 2 pages.
AU Application No. 2018279941, Office Action mailed Mar. 20, 2023; Applicant Magnolia Medical Technologies, Inc.; 3 pages.
AU Application No. 2018334138, Office Action mailed Jun. 24, 2023; Applicant Magnolia Medical Technologies, Inc.; 3 pages.
AU Application No. 2019204941, Office Action mailed Jul. 15, 2019; Applicant Magnolia Medical Technologies, Inc.; 4 pages.

(56) References Cited

OTHER PUBLICATIONS

AU Application No. 2020213415, Office Action mailed May 21, 2021; Applicant Magnolia Medical Technologies, Inc.; 3 pages.
AU Application No. 2020218544, Office Action mailed Jul. 31, 2024; Applicant Magnolia Medical Technologies, Inc.; 3 pages.
AU Application No. 2020234829, Office Action mailed Nov. 15, 2024; Applicant Magnolia Medical Technologies, Inc.; 3 pages.
AU Application No. 2020234829, Office Action mailed Sep. 11, 2025; Applicant Magnolia Medical Technologies, Inc.; 3 pages.
AU Application No. 2022200818, Office Action mailed May 11, 2023; Applicant Magnolia Medical Technologies, Inc.; 4 pages.
AU Application No. 2024203105, Office Action mailed Jan. 21, 2025; Applicant Magnolia Medical Technologies, Inc.; 3 pages.
AU Application No. 2024203140, Office Action mailed Apr. 8, 2025; Applicant Magnolia Medical Technologies, Inc.; 4 pages.
AU Application No. 2024205062, Office Action mailed Sep. 8, 2025; Applicant Magnolia Medical Technologies, Inc.; 2 pages.
Author Unknown, "Bact/Alert® Culture Media: Strong Outside, Strong Inside," [website], BIOMERIEUX, (Publication Date Unknown), [Accessed via Internet, publicly available at URL: https://www.biomerieux.com/US/en/our-offer/clinical-products/bact-alert-culture-media-bottles.html.], 10 pages.
Author Unknown, "BD BACTEC™ Blood Culture System," [website], Becton, Dickinson and Company, (Publication Date Unknown), [Accessed via Internet, publicly available at URL: https://www.bd.com/en-us/products-and-solutions/products/product-families/bd-bactec-blood-culture-system.], 9 pages.
Author Unknown, "Changing Blood Culture Collection in Hospitals Across America, Clinical Evidence, Studies," [website], KURIN, (Publication Date Unknown), [Retrieved from Internet on Sep. 15, 2025 at URL: https://www.kurin.com/studies/.], 22 pages.
Author Unknown, "Changing Blood Culture Collection in Hospitals Across America," [website], KURIN, (Publication Date Unknown), [Retrieved from Internet on Sep. 15, 2025 at URL: https://www.kurin.com/clinical-guidelines/.], 11 pages.
Author Unknown, "False Positive Blood Cultures—Improve the accuracy of blood culture," [website], KURIN, (Publication Date Unknown), [Retrieved from Internet on Sep. 15, 2025 at URL: https://www.kurin.com/false-positive-blood-cultures/.], 5 pages.
Author Unknown, "Kurin® Jet™ Blood Culture Collection Ordering Information," [website], KURIN, (Publication Date Unknown), [Accessed via Internet, publicly available at URL: https://www.kurin.com/kurin-jet/.], 2 pages.
Author Unknown, "Kurin Launches Kurin Jet, Redefining the Blood Culture Contamination Device Market," [website], KURIN, (Publication Date Unknown), [Accessed via Internet, publicly available at URL: https://www.kurin.com/kurin-launches-kurin-jet-redefining-the-blood-culture-contamination-device-market/.], 5 pages.
Author Unknown, "Kurin Lock® with Flash Technology: Better than conventional diversion," [website], KURIN, (Publication Date Unknown), [Retrieved from Internet on Sep. 26, 2025 at URL: https://www.kurin.com/kurin-jet/.], 10 pages.
Author Unknown, "Lowering the 3% Blood Culture Contamination Rate Benchmark," [website], KURIN, (Publication Date Unknown), [Retrieved from Internet on Sep. 15, 2025 at URL: https://www.kurin.com/3-percent-standard/.], 4 pages.
Author Unknown, "Newly Released CLSI National Blood Culture Guidelines Identify Best Practices and Evidence-Based Technology Solutions Such as Steripath® to Improve Patient Safety and Outcomes," [website], Magnolia Medical Technologies, Inc, (May 5, 2022), [Retrieved from Internet on Sep. 15, 2025 at URL: https://magnolia-medical.com/news/newly-released-clsi-national-blood-culture-guidelines-identify-best-practices-and-evidence-based-technology-solutions-such-as-steripath-to-improve-patient-safety-and-outcomes/.], 5 pages.
Author Unknown, "The Financial and Clinical Costs of False Positive Blood Cultures," [website], KURIN, (Publication Date Unknown), [Retrieved from Internet on Sep. 15, 2025 at URL: https://www.kurin.com/false-positives-blood-culture-cost/.], 5 pages.
Avatar: "Is it safe to reinfuse blood drawn from a CVAD via a syringe when checking line patency or drawing blood?" [retrieved online Jul. 31, 2024] URL:https://www.avatargroup.org.au/faq---blood-collection.html, 4 pages.
Bauman et al., "Don't Stick Me Again! Reducing Blood Culture Contamination," INOVA Fairfax Medical Campus, Emergency Department (2019), 1 page. (Publication Date unknown).
Bell et al., "Effectiveness of a Novel Specimen Collection System in Reducing Blood Culture Contamination Rates," Journal of Emergency Nursing, 44(6):570-575, (Nov. 2018; Epub Apr. 21, 2018).
Blakeney, "Reduction of Blood Culture Contaminations Using Initial Specimen Diversion Device," Beebe Healthcare presentation (Jun. 9, 2018), 1 page.
Brownfield et al.; "Emergency Department Observes 83% Reduction in Blood Culture Contamination with Initial Specimen Diversion Technology Adoption," APIC 48th Annual Educational Conference, Jun. 28-30, 2021, Poster Abstract ADS 34; Am. J. Infection Control; 49(6), Supplement; p. S14; 2 pages (Jun. 2021).
Bruneau et al., "Efficacy of a New Collection Procedure for Preventing Bacterial Contamination of Whole-blood Donations," Transfusion, 41(1): 74-81, (Jan. 2001).
Buzard, B.A. et al., "Evaluation of an Initial Specimen Diversion Device (ISDD) on Rates of Blood Culture Contamination in the Emergency Department," Kans J Med. Mar. 19, 2021; 14(1): 73-76. eCollection 2021.
CA Application No. 2875118, Office Action mailed Apr. 7, 2020; Applicant Magnolia Medical Technologies, Inc. et al.; 4 pages.
CA Application No. 2875118, Office Action mailed Mar. 21, 2019; Applicant Magnolia Medical Technologies, Inc. et al.; 5 pages.
CA Application No. 2931983, Office Action mailed Oct. 1, 2020; Applicant Magnolia Medical Technologies, Inc.; 3 pages.
CA Application No. 2931983, Office Action mailed Oct. 16, 2019; Applicant Magnolia Medical Technologies, Inc.; 4 pages.
CA Application No. 2932536, Office Action mailed Jul. 13, 2021; Applicant Magnolia Medical Technologies, Inc.; 4 pages.
CA Application No. 2932536, Office Action mailed Nov. 8, 2019; Applicant Magnolia Medical Technologies, Inc.; 6 pages.
CA Application No. 2932536, Office Action mailed Oct. 23, 2020; Applicant Magnolia Medical Technologies, Inc.; 6 pages.
CA Application No. 3066670, Office Action mailed Oct. 4, 2024; Applicant Magnolia Medical Technologies, Inc. et al.; 4 pages.
CA Application No. 3074105, Office Action mailed Nov. 15, 2024; Applicant Magnolia Medical Technologies, Inc.; 5 pages.
CA Application No. 3087992, Office Action mailed Mar. 20, 2025; Applicant Magnolia Medical Technologies, Inc.; 4 pages.
CA Application No. 3101972, Office Action mailed May 13, 2025; Applicant Magnolia Medical Technologies, Inc.; 4 pages.
CA Application No. 3120161, Office Action mailed Jun. 20, 2022; Applicant Magnolia Medical Technologies, Inc.; 4 pages.
CA Application No. 3129065, Office Action mailed Feb. 11, 2025; Applicant Magnolia Medical Technologies, Inc.; 3 pages.
CA Application No. 3132981, Office Action mailed Aug. 22, 2025; Applicant Magnolia Medical Technologies, Inc.; 5 pages.
CA Application No. 3136331, Office Action mailed Feb. 21, 2023; Applicant Magnolia Medical Technologies, Inc.; 4 pages.
CA Application No. 3164339, Office Action mailed Jan. 26, 2026; Applicant Magnolia Medical Technologies, Inc.; 4 pages.
CA Application No. 3183294, Office Action mailed Aug. 19, 2024; Applicant Magnolia Medical Technologies, Inc.; 5 pages.
Callado, G. Y. et al., "Diagnostic Stewardship: A Systematic Review and Meta-analysis of Blood Collection Diversion Devices Used to Reduce Blood Culture Contamination and Improve the Accuracy of Diagnosis in Clinical Settings," Open Forum Infect Dis. Aug. 11, 2023; 10(9): ofad433, 10 pages. eCollection Sep. 2023.
Chamarthy, P., et al.; "Mixing Characteristics in a Serpentine Micro-Channel," IMECE2004-61902; Proceedings of the ASME 2004 International Mechanical Engineering Congress and Exposition. Fluids Engineering. Anaheim, California, USA; Nov. 13-19, 2004, pp. 253-261; Exhibit 4; 10 pages.
Chang et al., "Impact of Blood Culture Diversion Device and Molecular Pathogen Identification on Vancomycin Use," San Antonio Military Medical Center (2016), 1 page. (Publication Date Unknown).

(56) References Cited

OTHER PUBLICATIONS

CN Application No. 201380040468.7, Office Action mailed Apr. 12, 2017; Applicant Magnolia Medical Technologies, Inc., with English Translation; 8 pages.
CN Application No. 201380040468.7, Office Action mailed Jun. 30, 2016; Applicant Magnolia Medical Technologies, Inc., with English Translation; 9 pages.
CN Application No. 201380071681.4, Office Action mailed Aug. 16, 2016; Applicant Magnolia Medical Technologies, Inc., with English Translation; 16 pages.
CN Application No. 201380071681.4, Office Action mailed Jun. 28, 2017; Applicant Magnolia Medical Technologies, Inc., with English Translation; 22 pages.
CN Application No. 201380072185.0, Office Action mailed Sep. 28, 2016; Applicant Magnolia Medical Technologies, Inc., with English Translation; 17 pages.
CN Application No. 201711078173.5, Office Action mailed Feb. 3, 2020; Applicant Magnolia Medical Technologies, Inc., with English Translation; 14 pages.
CN Application No. 201811146373.4, Office Action mailed Apr. 8, 2025; Applicant Magnolia Medical Technologies, Inc., with English Translation; 18 pages.
CN Application No. 201811146373.4, Office Action mailed Aug. 25, 2021; Applicant Magnolia Medical Technologies, Inc., with English Translation; 10 pages.
CN Application No. 201811146373.4, Office Action mailed Jan. 29, 2022; Applicant Magnolia Medical Technologies, Inc., with English Translation; 21 pages.
CN Application No. 201811146373.4, Office Action mailed Jul. 28, 2025; Applicant Magnolia Medical Technologies, Inc., with English Translation; 36 pages.
CN Application No. 201811146373.4, Office Action mailed Nov. 4, 2020; Applicant Magnolia Medical Technologies, Inc., with English Translation; 17 pages.
CN Application No. 201880050862.1, Office Action mailed Mar. 14, 2022; Applicant Magnolia Medical Technologies, Inc., with English Translation; 19 pages.
CN Application No. 201880066848.0, Office Action mailed Apr. 20, 2022; Applicant Magnolia Medical Technologies, Inc., with English Translation; 20 pages.
CN Application No. 202011295348.X, Office Action mailed Nov. 29, 2023; Applicant Magnolia Medical Technologies, Inc., with English Translation; 10 pages.
CN Application No. 202080025953.7, Office Action mailed Aug. 28, 2024; Applicant Magnolia Medical Technologies, Inc., with English Translation; 26 pages.
CN Application No. 202080025953.7, Office Action mailed Dec. 17, 2024; Applicant Magnolia Medical Technologies, Inc., with English Translation; 22 pages.
CN Application No. 202080025953.7, Office Action mailed Jan. 9, 2024; Applicant Magnolia Medical Technologies, Inc., with English Translation; 27 pages.
CN Application No. 202080025953.7, Office Action mailed May 24, 2025; Applicant Magnolia Medical Technologies, Inc., with English Translation; 12 pages.
CN Application No. 202080033513.6, Office Action mailed Oct. 9, 2022; Applicant Magnolia Medical Technologies, Inc., with English Translation; 19 pages.
CN Application No. 202080094860.X, Office Action mailed Jan. 10, 2025; Applicant Magnolia Medical Technologies, Inc., with English Translation; 20 pages.
CN Application No. 202310257287.5, Office Action mailed Apr. 23, 2025; Applicant Magnolia Medical Technologies, Inc., with English Translation; 21 pages.
Doern et al., "A Comprehensive Update on the Problem of Blood Culture Contamination and a Discussion of Methods for Addressing the Problem," Clinical Microbiology, 33(1): e00009-e00019, (Jan. 2020), 21 pages.
ENA (Emergency Nurses Association), "Clinical Practice Guideline: Synopsis - Prevention of Blood Culture Contamination," [website], Guidelinecentral, (May 8, 2018; last updated Oct. 18, 2025), [Accessed via Internet, publicly available at URL: https://www.guidelinecentral.com/guideline/308349/#section-420.], 1 page.
EP Application No. 13797732.8, Supplementary European Search Report mailed Dec. 7, 2015; Applicant Magnolia Medical Technologies, Inc. et al.; 5 pages.
EP Application No. 13845555.5, Supplementary European Search Report mailed Jul. 12, 2016; Applicant Magnolia Medical Technologies, Inc.; 6 pages.
EP Application No. 13859067.4, Extended European Search Report mailed Aug. 16, 2017; Applicant Magnolia Medical Technologies, Inc.; 6 pages.
EP Application No. 13859067.4, Extended European Search Report mailed Jan. 27, 2017; Applicant Magnolia Medical Technologies, Inc.; 4 pages.
EP Application No. 13859067.4, Extended European Search Report mailed Jun. 7, 2016; Applicant Magnolia Medical Technologies, Inc.; 4 pages.
EP Application No. 13860741.1, Supplementary European Search Report mailed Jun. 7, 2016; Applicant Magnolia Medical Technologies, Inc.; 5 pages.
EP Application No. 16200112.7, Extended European Search Report mailed Feb. 15, 2018; Applicant Magnolia Medical Technologies, Inc.; 3 pages.
EP Application No. 16200112.7, Extended European Search Report mailed Mar. 1, 2017; Applicant Magnolia Medical Technologies, Inc.; 6 pages.
EP Application No. 16808502.5, Extended European Search Report mailed Jan. 23, 2019; Applicant Bullington, Gregory J. et al.; 5 pages.
EP Application No. 16843182.3, Extended European Search Report mailed Mar. 26, 2019; Applicant Magnolia Medical Technologies, Inc.; 4 pages.
EP Application No. 17204012.3, Extended European Search Report mailed Feb. 14, 2018; Applicant Magnolia Medical Technologies, Inc.; 7 pages.
EP Application No. 17206745.6, Extended European Search Report mailed Feb. 19, 2018; Applicant Magnolia Medical Technologies, Inc.; 8 pages.
EP Application No. 17206745.6, Office Action mailed Feb. 18, 2020; Applicant Magnolia Medical Technologies, Inc.; 4 pages.
EP Application No. 18188136.8, Extended European Search Report mailed May 16, 2019; Applicant Magnolia Medical Technologies, Inc.; 9 pages.
EP Application No. 18813278.1, Extended European Search Report mailed Feb. 17, 2021; Applicant Magnolia Medical Technologies, Inc.; 4 pages.
EP Application No. 18855938.9, Extended European Search Report mailed Aug. 2, 2021; Applicant Magnolia Medical Technologies, Inc.; 7 pages.
EP Application No. 19156636.3, Extended European Search Report mailed Aug. 27, 2019; Applicant Magnolia Medical Technologies, Inc.; 7 pages.
EP Application No. 19190772.4, Extended European Search Report mailed Feb. 10, 2020; Applicant Magnolia Medical Technologies, Inc.; 7 pages.
EP Application No. 20167572.5, Extended European Search Report mailed Sep. 30, 2020; Applicant Magnolia Medical Technologies, Inc.; 10 pages.
EP Application No. 20176877.7, Extended European Search Report mailed Dec. 1, 2020; Applicant Magnolia Medical Technologies, Inc.; 9 pages.
EP Application No. 20207898.6, Extended European Search Report mailed Aug. 30, 2021; Applicant Magnolia Medical Technologies, Inc.; 8 pages.
EP Application No. 20709440.0, Office Action mailed Feb. 18, 2025; Applicant Magnolia Medical Technologies, Inc.; 6 pages.
EP Application No. 20716348.6, Office Action mailed Jul. 12, 2022; Applicant Magnolia Medical Technologies, Inc.; 7 pages.
EP Application No. 21167069.0, Extended European Search Report mailed Nov. 10, 2021; Applicant Magnolia Medical Technologies, Inc.; 9 pages.

(56) References Cited

OTHER PUBLICATIONS

EP Application No. 21167625.9, Extended European Search Report mailed Oct. 8, 2021; Applicant Magnolia Medical Technologies, Inc.; 7 pages.
EP Application No. 21197514.9, Extended European Search Report mailed Mar. 30, 2022; Applicant Magnolia Medical Technologies, Inc.; 9 pages.
EP Application No. 22158983.1, Extended European Search Report mailed Aug. 1, 2022; Applicant Magnolia Medical Technologies, Inc.; 8 pages.
EP Application No. 22172183.0, Extended European Search Report mailed Nov. 9, 2022; Applicant Magnolia Medical Technologies, Inc.; 7 pages.
EP Application No. 22194769.0, Extended European Search Report mailed Feb. 28, 2023; Applicant Magnolia Medical Technologies, Inc.; 9 pages.
EP Application No. 22210589.2, Extended European Search Report mailed Apr. 17, 2023; Applicant Magnolia Medical Technologies, Inc.; 6 pages.
EP Application No. 23153164.1, Extended European Search Report mailed Aug. 7, 2023; Applicant Magnolia Medical Technologies, Inc.; 8 pages.
EP Application No. 23171135.9, Extended European Search Report mailed Oct. 30, 2023; Applicant Magnolia Medical Technologies, Inc.; 8 pages.
EP Application No. 23173044.1, Extended European Search Report mailed Oct. 27, 2023; Applicant Magnolia Medical Technologies, Inc.; 8 pages.
EP Application No. 23182529.0, Extended European Search Report mailed Dec. 19, 2023; Applicant Magnolia Medical Technologies, Inc.; 13 pages.
EP Application No. 23182529.0, Office Action mailed Jul. 29, 2025; Applicant Magnolia Medical Technologies, Inc.; 6 pages.
EP Application No. 23209844.2, Extended European Search Report mailed Mar. 20, 2024; Applicant Magnolia Medical Technologies, Inc.; 9 pages.
EP Application No. 23217471.4, Extended European Search Report mailed May 22, 2024; Applicant Magnolia Medical Technologies, Inc.; 8 pages.
EP Application No. 23218666.8, Extended European Search Report mailed Apr. 18, 2024; Applicant Magnolia Medical Technologies, Inc.; 9 pages.
EP Application No. 24217446.4, Extended European Search Report mailed Apr. 17, 2025; Applicant Magnolia Medical Technologies, Inc.; 8 pages.
EP Application No. 25164992.7, Extended European Search Report mailed Aug. 26, 2025; Applicant Magnolia Medical Technologies, Inc.; 8 pages.
EP Application No. 26161796.3, Extended European Search Report mailed May 21, 2026; Applicant Magnolia Medical Technologies, Inc.; 8 Pages.
Garstecki et al., "Formation of Droplets and Bubbles in a Microfluidic T-Junction-Scaling and Mechanism of Break-Up," Lab on a Chip, 6(3): 437-446, (Mar. 2006).
GB Application No. 1506837.2, Office Action mailed Jul. 19, 2017; Applicant Magnolia Medical Technologies, Inc.; 6 pages.
GB Application No. 1805101.1, Office Action mailed May 25, 2018; Applicant Magnolia Medical Technologies, Inc.; 8 pages.
Geisler et al., "Model to Evaluate the Impact of Hospital-Based Interventions Targeting False-Positive Blood Cultures on Economic and Clinical Outcomes," Journal of Hospital Infection, 102(4):438-444, (Mar. 2019).
IL Application No. 238991, Office Action mailed Feb. 13, 2020; Applicant Magnolia Medical Technologies, Inc., with English Translation; 10 pages.
IL Application No. 238991, Office Action mailed Nov. 12, 2018; Applicant Magnolia Medical Technologies, Inc., with English Translation; 6 pages.
IL Application No. 273025, Office Action mailed Dec. 4, 2022; Applicant Magnolia Medical Technologies, Inc. et al., with English Translation; 6 pages.
IL Application No. 285289, Office Action mailed May 6, 2024; Applicant Magnolia Medical Technologies, Inc. et al.; 4 pages. (English Only).
IL Application No. 286263, Office Action mailed Aug. 5, 2025; Applicant Magnolia Medical Technologies, Inc. et al.; 3 pages. (English Only).
IL Application No. 286263, Office Action mailed May 12, 2024; Applicant Magnolia Medical Technologies, Inc. et al.; 4 pages. (English Only).
IL Application No. 303591, Office Action mailed Feb. 25, 2024; Applicant Magnolia Medical Technologies, Inc. et al.; 4 pages.
IL Application No. 309638, Office Action mailed Aug. 11, 2025; Applicant Magnolia Medical Technologies, Inc. et al.; 3 pages. (English Only).
IL Application No. 309638, Office Action mailed Jul. 16, 2024; Applicant Magnolia Medical Technologies, Inc. et al.; 3 pages. (English Only).
IL Application No. 313917, Office Action mailed May 29, 2025; Applicant Magnolia Medical Technologies, Inc. et al.; 4 pages. (English Only).
IN Application No. 11068/DELNP/2014, Office Action mailed Sep. 28, 2020; Applicant Magnolia Medical Technologies, Inc., with English Translation; 6 pages.
IN Application No. 202017008581, Office Action mailed Mar. 8, 2022; Applicant Magnolia Medical Technologies, Inc., with English Translation; 7 pages.
JP Application No. 2015-515178, Office Action mailed Feb. 16, 2017; Applicant Magnolia Medical Technologies, Inc. et al., with English Translation; 7 pages.
JP Application No. 2015-545494, Office Action mailed Jun. 19, 2017; Applicant Magnolia Medical Technologies, Inc., with English Translation; 9 pages.
JP Application No. 2015-545813, Office Action mailed Jul. 4, 2017; Applicant Magnolia Medical Technologies, Inc., with English Translation; 14 pages.
JP Application No. 2017-214629, Office Action mailed Jul. 23, 2019; Applicant Magnolia Medical Technologies, Inc., with English Translation; 8 pages.
JP Application No. 2017-214629, Office Action mailed Sep. 20, 2018; Applicant Magnolia Medical Technologies, Inc., with English Translation; 9 pages.
JP Application No. 2018-081980, Office Action mailed Feb. 21, 2019; Applicant Magnolia Medical Technologies, Inc., with English Translation; 9 pages.
JP Application No. 2018-081980, Office Action mailed Jan. 30, 2020; Applicant Magnolia Medical Technologies, Inc., with English Translation; 11 pages.
JP Application No. 2018-086721, Office Action mailed Mar. 15, 2019; Applicant Magnolia Medical Technologies, Inc., with English Translation; 6 pages.
JP Application No. 2019-230734, Office Action mailed Jan. 22, 2021; Applicant Magnolia Medical Technologies, Inc., with English Translation; 9 pages.
JP Application No. 2019-230734, Office Action mailed Jan. 5, 2022; Applicant Magnolia Medical Technologies, Inc., with English Translation; 6 pages.
JP Application No. 2020-075727, Office Action mailed Jul. 28, 2021; Applicant Magnolia Medical Technologies, Inc., with English Translation; 37 pages.
JP Application No. 2020-075727, Office Action mailed Mar. 28, 2023; Applicant Magnolia Medical Technologies, Inc., with English Translation; 6 pages.
JP Application No. 2020-075727, Office Action mailed May 18, 2022; Applicant Magnolia Medical Technologies, Inc., with English Translation; 11 pages.
JP Application No. 2020-094488, Office Action mailed Aug. 2, 2021; Applicant Magnolia Medical Technologies, Inc., with English Translation; 4 pages.

(56) References Cited

OTHER PUBLICATIONS

JP Application No. 2020-094488, Office Action mailed Mar. 31, 2022; Applicant Magnolia Medical Technologies, Inc., with English Translation; 6 pages.
JP Application No. 2020-511930, Office Action mailed Aug. 23, 2022; Applicant Magnolia Medical Technologies, Inc., with English Translation; 9 pages.
JP Application No. 2020-517772, Office Action mailed Dec. 26, 2022; Applicant Magnolia Medical Technologies, Inc., with English Translation; 6 pages.
JP Application No. 2020-517772, Office Action mailed Mar. 14, 2022; Applicant Magnolia Medical Technologies, Inc., with English Translation; 13 pages.
JP Application No. 2020-566232, Office Action mailed Apr. 12, 2023; Applicant Magnolia Medical Technologies, Inc., with English Translation; 27 pages.
JP Application No. 2020-566232, Office Action mailed Sep. 19, 2023; Applicant Magnolia Medical Technologies, Inc., with English Translation; 6 pages.
JP Application No. 2021-546225, Office Action mailed Dec. 19, 2023; Applicant Magnolia Medical Technologies, Inc., with English Translation; 11 pages.
JP Application No. 2021-552145, Office Action mailed Jan. 15, 2024; Applicant Magnolia Medical Technologies, Inc., with English Translation; 9 pages.
JP Application No. 2021-552145, Office Action mailed Sep. 11, 2024; Applicant Magnolia Medical Technologies, Inc., with English Translation; 4 pages.
JP Application No. 2022-074696, Office Action mailed Feb. 20, 2023; Applicant Magnolia Medical Technologies, Inc., with English Translation; 11 pages.
JP Application No. 2022-074696, Office Action mailed Oct. 25, 2023; Applicant Magnolia Medical Technologies, Inc., with English Translation; 7 pages.
JP Application No. 2022-149585, Office Action mailed Sep. 26, 2023; Applicant Magnolia Medical Technologies, Inc., with English Translation; 9 pages.
JP Application No. 2022-184274, Office Action Appeal Decision No. 2024-016403 mailed Nov. 7, 2025, Applicant Magnolia Medical Technologies, Inc., with English translation; 73 pages.
JP Application No. 2022-184274, Office Action mailed Jun. 14, 2024; Applicant Magnolia Medical Technologies, Inc., with English Translation; 4 pages.
JP Application No. 2022-184274, Office Action mailed Oct. 27, 2023; Applicant Magnolia Medical Technologies, Inc., with English Translation; 6 pages.
JP Application No. 2022-212405, Office Action mailed Jun. 20, 2024; Applicant Magnolia Medical Technologies, Inc., with English Translation; 6 pages.
JP Application No. 2022-212405, Office Action mailed Nov. 29, 2023; Applicant Magnolia Medical Technologies, Inc., with English Translation; 13 pages.
JP Application No. 2022-534220, Office Action mailed Sep. 13, 2024; Applicant Magnolia Medical Technologies, Inc., with English Translation; 8 pages.
JP Application No. 2023-075104, Office Action mailed Feb. 29, 2024; Applicant Magnolia Medical Technologies, Inc., with English Translation; 9 pages.
JP Application No. 2024-014849, Office Action mailed Apr. 30, 2025; Applicant Magnolia Medical Technologies, Inc., with English Translation; 9 pages.
JP Application No. 2024-014849, Office Action mailed Jan. 28, 2026; Applicant Magnolia Medical Technologies, Inc., with English Translation; 6 pages.
JP Application No. 2024-020482, Office Action mailed Mar. 11, 2025; Applicant Magnolia Medical Technologies, Inc., with English Translation; 16 pages.
JP Application No. 2024-115518, Office Action mailed Jun. 11, 2025; Applicant Magnolia Medical Technologies, Inc., with English Translation; 6 pages.
JP Application No. 2024-127830, Office Action mailed Nov. 4, 2025; Applicant Magnolia Medical Technologies, Inc., with English Translation; 8 pages.
JP Application No. 2024-153369, Office Action mailed Feb. 18, 2026; Applicant Magnolia Medical Technologies, Inc., with English Translation; 6 pages.
JP Application No. 2024-153369, Office Action mailed Sep. 5, 2025; Applicant Magnolia Medical Technologies, Inc., with English Translation; 10 pages.
JP Application No. 2024-187934, Office Action mailed Apr. 28, 2025; Applicant Magnolia Medical Technologies, Inc., with English Translation; 12 pages.
Lanteri et al., "Reduction of Blood Culture Contaminations in the Emergency Department," Department of Emergency Medicine, San Antonio Military Medical Center (2016), 1 page.
Marshall, L.A., et al.; "An injection molded microchip for nucleic acid purification from 25 microliter samples using isotachophoresis," J Chromatogr A.; 1331; pp. 139-142 (Feb. 2014).
McDonald, C.P.; "Bacterial risk reduction by improved donor arm disinfection, diversion and bacterial screening," Transfus Med., Dec. 2006, 16(6), pp. 381-396. doi: 10.1111/j.1365-3148.2006.00697.x.
Mohajer, M.A., et al.; "The Impact of Initial Specimen Diversion Systems on Blood Culture Contamination," Open Forum Infect Dis.; 10(5): ofad182; pp. 1-6. doi: 10.1093/ofid/ofad182 (Apr. 5, 2023).
Nielsen et al., "Initial Specimen Diversion Device Reduces Blood Culture Contamination and Vancomycin Use in Academic Medical Centre," J. Hospital Infection, vol. 120:127-133 (Feb. 2022).
Patel, R. et al., "Optimized Pathogen Detection with 30—Compared to 20-Milliliter Blood Culture Draws," Journal of Clinical Microbiology, Epub Oct. 5, 2011, 49(12):4047-4051 (Dec. 2011).
PCT Application No. PCT/US2007/087951, International Search Report and Written Opinion mailed May 16, 2008, Applicant Patton, Richard G.; 8 pages.
PCT Application No. PCT/US2013/043289, International Search Report and Written Opinion mailed Oct. 24, 2013, Applicant Magnolia Medical Technologies, Inc. et al.; 15 pages.
PCT Application No. PCT/US2013/052493, International Search Report and Written Opinion mailed Nov. 27, 2013, Applicant Magnolia Medical Technologies, Inc.; 7 pages.
PCT Application No. PCT/US2013/063975, International Search Report and Written Opinion mailed Mar. 20, 2014, Applicant Magnolia Medical Technologies, Inc.; 16 pages.
PCT Application No. PCT/US2013/071491, International Search Report and Written Opinion mailed Aug. 5, 2014, Applicant Magnolia Medical Technologies, Inc.; 9 pages.
PCT Application No. PCT/US2013/072563, International Search Report and Written Opinion mailed Feb. 7, 2014, Applicant Magnolia Medical Technologies, Inc.; 11 pages.
PCT Application No. PCT/US2013/073080, International Search Report and Written Opinion mailed Feb. 18, 2014, Applicant Magnolia Medical Technologies, Inc.; 14 pages.
PCT Application No. PCT/US2016/037160, International Search Report and Written Opinion mailed Sep. 30, 2016, Applicant Magnolia Medical Technologies, Inc.; 10 pages.
PCT Application No. PCT/US2016/050380, International Search Report and Written Opinion mailed Dec. 1, 2016, Applicant Magnolia Medical Technologies, Inc.; 6 pages.
PCT Application No. PCT/US2018/036910, International Search Report and Written Opinion mailed Sep. 4, 2018, Applicant Magnolia Medical Technologies, Inc.; 13 pages.
PCT Application No. PCT/US2018/050621, International Search Report and Written Opinion mailed Nov. 26, 2018, Applicant Magnolia Medical Technologies, Inc.; 11 pages.
PCT Application No. PCT/US2019/034626, International Search Report and Written Opinion mailed Aug. 22, 2019, Applicant Magnolia Medical Technologies, Inc.; 16 pages.
PCT Application No. PCT/US2020/017261, International Search Report and Written Opinion mailed May 14, 2020, Applicant Magnolia Medical Technologies, Inc.; 13 pages.

(56) References Cited

OTHER PUBLICATIONS

PCT Application No. PCT/US2020/022125, International Search Report and Written Opinion mailed May 26, 2020, Applicant Magnolia Medical Technologies, Inc.; 17 pages.
PCT Application No. PCT/US2020/064600, International Search Report and Written Opinion mailed Mar. 18, 2021, Applicant Magnolia Medical Technologies, Inc.; 14 pages.
Povroznik, M.D.; "Initial Specimen Diversion Device Utilization Mitigates Blood Culture Contamination Across Regional Community Hospital and Acute Care Facility," Am J Med Qual., Epub Mar. 30, 2022, 37(5):405-412 (Sep.-Oct. 2022).
Rupp, M.E., et al.; "Reduction in Blood Culture Contamination Through Use of Initial Specimen Diversion Device," Clin Infect Dis.; 65(2):201-205 (Jul. 15, 2017).
Shen, H., et al.; "A microfluidic chip based sequential injection system with trapped droplet liquid-liquid extraction and chemiluminescence detection," Lab Chip; 6(10): 1387-1389 (Oct. 2006).
Skoglund et al., "Estimated Clinical and Economic Impact through Use of a Novel Blood Collection Device To Reduce Blood Culture Contamination in the Emergency Department: a Cost-Benefit Analysis," J Clin Microbiol. (Jan. 2019); 57(1):e01015-18, 10 pages.
Snyder, S.R., et al.; "Effectiveness of practices to reduce blood culture contamination: A Laboratory Medicine Best Practices systematic review and meta-analysis," Clin Biochem .; Epub Jun. 16, 2012; 45(Issues 13-14):999-1011. doi: 10.1016/j.clinbiochem.2012.06.007, 13 pages (Sep. 2012).
Steed et al., "Study Demonstrates Reduction in Blood Culture Contamination Rates with Novel Blood Culture Collection Device," Clinical Lab Products Magazine (Feb. 2018), 2 pages.
Tompkins et al., "Getting to Zero: Impact of A Device To Reduce Blood Culture Contamination and False-Positive Central-Line-Associated Bloodstream Infection," Infection Control & Hospital Epidemiology, pp. 1-5 (Nov. 2022).
Tongma et al., "Significant Reduction of Blood Culture Contamination in the Emergency Department (ED) Using the Steripath® Blood Diversion Device," Open Forum Infectious Diseases, vol. 4, Supp. 1, 2035 (Oct. 2017), 1 page.
U.S. Appl. No. 11/955,635, Final Office Action mailed Dec. 3, 2010; Inventor Patton, Richard G.; 11 pages.
U.S. Appl. No. 11/955,635, Non-Final Office Action mailed Jul. 22, 2010; Inventor Patton, Richard G.; 11 pages.
U.S. Appl. No. 13/335,241, Non-Final Office Action mailed Apr. 20, 2012; Inventor Patton, Richard G.; 12 pages.
U.S. Appl. No. 13/458,508, Non-Final Office Action mailed Jul. 24, 2012; Inventor Patton, Richard G.; 13 pages.
U.S. Appl. No. 13/675,295, Non-Final Office Action mailed May 23, 2013; Inventor Patton, Richard G.; 15 pages.
U.S. Appl. No. 13/952,964, Non-Final Office Action mailed Mar. 20, 2015; Inventor Bullington, Gregory J. et al.; 11 pages.
U.S. Appl. No. 13/954,528, Non-Final Office Action mailed Mar. 17, 2014; Inventor Bullington, Gregory J. et al.; 10 pages.
U.S. Appl. No. 14/049,326, Non-Final Office Action mailed Apr. 24, 2015; Inventor Bullington, Gregory J. et al.; 10 pages.
U.S. Appl. No. 14/089,267, Non-Final Office Action mailed Jun. 19, 2014; Inventor Patton, Richard G.; 13 pages.
U.S. Appl. No. 14/096,826, Final Office Action mailed Mar. 8, 2018; Inventor Bullington, Gregory J. et al.; 14 pages.
U.S. Appl. No. 14/096,826, Non-Final Office Action mailed Jul. 26, 2017; Inventor Bullington, Gregory J. et al.; 12 pages.
U.S. Appl. No. 14/264,481, Final Office Action mailed Apr. 13, 2017; Inventor Bullington, Gregory J. et al.; 14 pages.
U.S. Appl. No. 14/264,481, Final Office Action mailed Jul. 14, 2016; Inventor Bullington, Gregory J. et al.; 9 pages.
U.S. Appl. No. 14/264,481, Non-Final Office Action mailed Feb. 26, 2016; Inventor Bullington, Gregory J. et al.; 10 pages.
U.S. Appl. No. 14/264,481, Non-Final Office Action mailed Jul. 1, 2015; Inventor Bullington, Gregory J. et al.; 13 pages.
U.S. Appl. No. 14/264,481, Non-Final Office Action mailed Oct. 21, 2016; Inventor Bullington, Gregory J. et al.; 10 pages.
U.S. Appl. No. 14/264,481, Non-Final Office Action mailed Sep. 7, 2017; Inventor Bullington, Gregory J. et al.; 12 pages.
U.S. Appl. No. 14/493,796, Non-Final Office Action mailed Jan. 27, 2015; Inventor Bullington, Gregory et al.; 7 pages.
U.S. Appl. No. 14/494,208, Non-Final Office Action mailed Jan. 27, 2015; Inventor Bullington, Gregory et al.; 7 pages.
U.S. Appl. No. 14/498,102, Final Office Action mailed Sep. 24, 2018; Inventor Patton, Richard G.; 18 pages.
U.S. Appl. No. 14/498,102, Non-Final Office Action mailed Oct. 17, 2017; Inventor Patton, Richard G.; 20 pages.
U.S. Appl. No. 14/662,676, Non-Final Office Action mailed Sep. 5, 2018; Inventor Bullington, Gregory et al.; 25 pages.
U.S. Appl. No. 14/712,431, Non-Final Office Action mailed Sep. 14, 2018; Inventor Bullington, Gregory et al.; 10 pages.
U.S. Appl. No. 14/712,437, Non-Final Office Action mailed Oct. 25, 2018; Inventor Bullington, Gregory J. et al.; 20 pages.
U.S. Appl. No. 14/728,318, Final Office Action mailed Dec. 20, 2018; Inventor Bullington, Gregory J. et al.; 26 pages.
U.S. Appl. No. 14/728,318, Final Office Action mailed Jan. 8, 2018; Inventor Bullington, Gregory J. et al.; 36 pages.
U.S. Appl. No. 14/728,318, Final Office Action mailed Jul. 18, 2019; Inventor Bullington, Gregory J. et al.; 27 pages.
U.S. Appl. No. 14/728,318, Non-Final Office Action mailed May 19, 2017; Inventor Bullington, Gregory J. et al.; 26 pages.
U.S. Appl. No. 14/838,794, Non-Final Office Action mailed Aug. 3, 2017; Inventor Bullington, Gregory J. et al.; 8 pages.
U.S. Appl. No. 14/880,397, Final Office Action mailed Sep. 24, 2018; Inventor Bullington, Gregory J. et al.; 5 pages.
U.S. Appl. No. 14/880,397, Non-Final Office Action mailed Apr. 17, 2018; Inventor Bullington, Gregory J. et al.; 6 pages.
U.S. Appl. No. 14/926,784, Final Office Action mailed Jan. 15, 2019; Inventor Bullington, Gregory J. et al.; 15 pages.
U.S. Appl. No. 14/926,784, Non-Final Office Action mailed Jan. 21, 2020; Inventor Bullington, Gregory J. et al.; 17 pages.
U.S. Appl. No. 14/926,784, Non-Final Office Action mailed May 25, 2018; Inventor Bullington, Gregory J. et al.; 17 pages.
U.S. Appl. No. 15/088,842, Non-Final Office Action mailed Nov. 23, 2016; Inventor Patton, Richard G.; 20 pages.
U.S. Appl. No. 15/180,454, Final Office Action mailed Apr. 1, 2020; Inventor Bullington, Gregory J. et al.; 28 pages.
U.S. Appl. No. 15/180,454, Non-Final Office Action mailed Jan. 21, 2021; Inventor Bullington, Gregory J. et al.; 24 pages.
U.S. Appl. No. 15/180,454, Non-Final Office Action mailed Jul. 25, 2019; Inventor Bullington, Gregory J. et al.; 27 pages.
U.S. Appl. No. 15/257,185, Non-Final Office Action mailed Aug. 8, 2017; Inventor Bullington, Gregory J. et al.; 5 pages.
U.S. Appl. No. 15/432,310, Non-Final Office Action mailed Apr. 12, 2017; Inventor Patton, Richard G.; 14 pages.
U.S. Appl. No. 15/435,684, Non-Final Office Action mailed Jun. 12, 2017; Inventor Patton, Richard G.; 19 pages.
U.S. Appl. No. 15/448,891, Non-Final Office Action mailed Jun. 16, 2017; Inventor Patton, Richard G.; 25 pages.
U.S. Appl. No. 15/457,082, Non-Final Office Action mailed Jun. 15, 2017; Inventor Patton, Richard G.; 22 pages.
U.S. Appl. No. 15/829,015, Non-Final Office Action mailed Feb. 6, 2018; Inventor Patton, Richard G.; 24 pages.
U.S. Appl. No. 15/829,018, Non-Final Office Action mailed Feb. 16, 2018; Inventor Patton, Richard G.; 13 pages.
U.S. Appl. No. 15/829,023, Non-Final Office Action mailed Feb. 7, 2018; Inventor Patton, Richard G.; 25 pages.
U.S. Appl. No. 15/832,055, Non-Final Office Action mailed Feb. 8, 2018; Inventor Patton, Richard G.; 21 pages.
U.S. Appl. No. 15/832,087, Non-Final Office Action mailed Feb. 7, 2018; Inventor Patton, Richard G.; 24 pages.
U.S. Appl. No. 15/832,091, Non-Final Office Action mailed Feb. 22, 2018; Inventor Bullington, Gregory J. et al.; 16 pages.
U.S. Appl. No. 15/854,273, Final Office Action mailed Mar. 15, 2019; Inventor Bullington, Gregory J. et al.; 19 pages.
U.S. Appl. No. 15/854,273, Non-Final Office Action mailed Jan. 13, 2020; Inventor Bullington, Gregory J. et al.; 13 pages.
U.S. Appl. No. 15/854,273, Non-Final Office Action mailed Sep. 7, 2018; Inventor Bullington, Gregory J. et al.; 15 pages.

(56) References Cited

OTHER PUBLICATIONS

U.S. Appl. No. 15/925,159, Final Office Action mailed May 14, 2019; Inventor Bullington, Gregory J. et al.; 13 pages.
U.S. Appl. No. 15/925,159, Non-Final Office Action mailed Nov. 26, 2018; Inventor Bullington, Gregory J. et al.; 11 pages.
U.S. Appl. No. 16/004,955, Non-Final Office Action mailed Feb. 16, 2021; Inventor Bullington, Gregory J. et al.; 28 pages.
U.S. Appl. No. 16/129,066, Non-Final Office Action mailed Sep. 3, 2020; Inventor Bullington, Gregory J. et al.; 13 pages.
U.S. Appl. No. 16/255,055, Non-Final Office Action mailed Mar. 18, 2019; Inventor Bullington, Gregory J. et al.; 16 pages.
U.S. Appl. No. 16/255,058, Non-Final Office Action mailed Mar. 30, 2021; Inventor Bullington, Gregory J. et al.; 16 pages.
U.S. Appl. No. 16/274,835, Non-Final Office Action mailed Feb. 12, 2021; Inventor Bullington, Gregory J. et al.; 17 pages.
U.S. Appl. No. 16/299,962, Final Office Action mailed Dec. 26, 2019; Inventor Bullington, Gregory J. et al.; 14 pages.
U.S. Appl. No. 16/299,962, Final Office Action mailed Jun. 15, 2021; Inventor Bullington, Gregory J. et al.; 17 pages.
U.S. Appl. No. 16/299,962, Non-Final Office Action mailed Dec. 9, 2020; Inventor Bullington, Gregory J. et al.; 15 pages.
U.S. Appl. No. 16/299,962, Non-Final Office Action mailed May 2, 2019; Inventor Bullington, Gregory J. et al.; 14 pages.
U.S. Appl. No. 16/376,745, Non-Final Office Action mailed May 14, 2021; Inventor Bullington, Gregory J. et al.; 13 pages.
U.S. Appl. No. 16/379,128, Non-Final Office Action mailed Apr. 26, 2022; Inventor Patton, Richard G.; 14 pages.
U.S. Appl. No. 16/426,380, Final Office Action mailed May 7, 2021; Inventor Bullington, Gregory J. et al.; 28 pages.
U.S. Appl. No. 16/426,380, Non-Final Office Action mailed Oct. 30, 2020; Inventor Bullington, Gregory J. et al.; 29 pages.
U.S. Appl. No. 16/785,170, Non-Final Office Action mailed Sep. 14, 2022; Inventor Bullington, Gregory J. et al.; 11 pages.
U.S. Appl. No. 16/789,034, Non-Final Office Action mailed Feb. 9, 2023; Inventor Bullington, Gregory J. et al.; 11 pages.
U.S. Appl. No. 16/815,521, Non-Final Office Action mailed Oct. 25, 2023; Inventor Bullington, Gregory J. et al.; 9 pages.
U.S. Appl. No. 16/815,526, Non-Final Office Action mailed Aug. 18, 2022; Inventor Bullington, Gregory J. et al.; 13 pages.
U.S. Appl. No. 16/934,975, Non-Final Office Action mailed Oct. 6, 2022; Inventor Bullington, Gregory J. et al.; 18 pages.
U.S. Appl. No. 17/119,732, Non-Final Office Action mailed Aug. 25, 2022; Inventor Bullington, Gregory J. et al.; 30 pages.
U.S. Appl. No. 17/136,882, Final Office Action mailed Dec. 31, 2024; Inventor Bullington, Gregory J. et al.; 6 pages.
U.S. Appl. No. 17/136,882, Final Office Action mailed Nov. 8, 2023; Inventor Bullington, Gregory J. et al.; 11 pages.
U.S. Appl. No. 17/136,882, Non-Final Office Action mailed Apr. 19, 2024; Inventor Bullington, Gregory J. et al.; 8 pages.
U.S. Appl. No. 17/136,882, Non-Final Office Action mailed Jun. 9, 2023; Inventor Bullington, Gregory J. et al.; 11 pages.
U.S. Appl. No. 17/138,056, Non-Final Office Action mailed Dec. 21, 2022; Inventor Bullington, Gregory J. et al.; 11 pages.
U.S. Appl. No. 17/388,971, Non-Final Office Action mailed Nov. 23, 2021; Inventor Bullington, Gregory J. et al.; 19 pages.
U.S. Appl. No. 17/388,979, Non-Final Office Action mailed Dec. 8, 2021; Inventor Bullington, Gregory J. et al.; 21 pages.
U.S. Appl. No. 17/390,249, Non-Final Office Action mailed Nov. 8, 2023; Inventor Bullington, Gregory J. et al.; 9 pages.
U.S. Appl. No. 17/403,500, Final Office Action mailed Jul. 28, 2023; Inventor Bullington, Gregory J. et al.; 18 pages.
U.S. Appl. No. 17/403,500, Final Office Action mailed Nov. 13, 2024; Inventor Bullington, Gregory J. et al.; 27 pages.
U.S. Appl. No. 17/403,500, Non-Final Office Action mailed May 20, 2024; Inventor Bullington, Gregory J. et al.; 28 pages.
U.S. Appl. No. 17/403,500, Non-Final Office Action mailed Sep. 27, 2022; Inventor Bullington, Gregory J. et al.; 29 pages.
U.S. Appl. No. 17/516,887, Final Office Action mailed Aug. 13, 2025; Inventor Bullington, Gregory J. et al.; 24 pages.
U.S. Appl. No. 17/516,887, Non-Final Office Action mailed Jan. 13, 2025; Inventor Bullington, Gregory J. et al.; 42 pages.
U.S. Appl. No. 17/525,682, Non-Final Office Action mailed Feb. 7, 2022; Inventor Bullington, Gregory J. et al.; 12 pages.
U.S. Appl. No. 17/532,382, Non-Final Office Action mailed Feb. 7, 2022; Inventor Bullington, Gregory J. et al.; 10 pages.
U.S. Appl. No. 17/559,081, Non-Final Office Action mailed Jan. 12, 2026; Inventor Bullington, Gregory J. et al.; 10 pages.
U.S. Appl. No. 17/583,791, Non-Final Office Action mailed Dec. 23, 2024; Inventor Bullington, Gregory J. et al.; 19 pages.
U.S. Appl. No. 17/591,237, Final Office Action mailed Aug. 20, 2025; Inventor Bullington, Gregory J. et al.; 24 pages.
U.S. Appl. No. 17/591,237, Final Office Action mailed Aug. 25, 2023; Inventor Bullington, Gregory J. et al.; 25 pages.
U.S. Appl. No. 17/591,237, Final Office Action mailed Aug. 4, 2022; Inventor Bullington, Gregory J. et al.; 26 pages.
U.S. Appl. No. 17/591,237, Non-Final Office Action mailed Feb. 16, 2023; Inventor Bullington, Gregory J. et al.; 34 pages.
U.S. Appl. No. 17/591,237, Non-Final Office Action mailed Jan. 24, 2025; Inventor Bullington, Gregory J. et al.; 34 pages.
U.S. Appl. No. 17/591,237, Non-Final Office Action mailed May 3, 2022; Inventor Bullington, Gregory J. et al.; 20 pages.
U.S. Appl. No. 17/591,239, Final Office Action mailed Aug. 23, 2023; Inventor Bullington, Gregory J. et al.; 23 pages.
U.S. Appl. No. 17/591,239, Final Office Action mailed Aug. 4, 2022; Inventor Bullington, Gregory J. et al.; 26 pages.
U.S. Appl. No. 17/591,239, Non-Final Office Action mailed Feb. 17, 2023; Inventor Bullington, Gregory J. et al.; 34 pages.
U.S. Appl. No. 17/591,239, Non-Final Office Action mailed Jan. 24, 2025; Inventor Bullington, Gregory J. et al.; 32 pages.
U.S. Appl. No. 17/591,239, Non-Final Office Action mailed May 3, 2022; Inventor Bullington, Gregory J. et al.; 21 pages.
U.S. Appl. No. 17/684,920, Final Office Action mailed Jan. 31, 2023; Inventor Bullington, Gregory J. et al.; 9 pages.
U.S. Appl. No. 17/684,920, Non-Final Office Action mailed Jul. 11, 2022; Inventor Bullington, Gregory J. et al.; 12 pages.
U.S. Appl. No. 17/710,389, Non-Final Office Action mailed Jun. 16, 2022; Inventor Bullington, Gregory J. et al.; 25 pages.
U.S. Appl. No. 17/710,401, Non-Final Office Action mailed Jul. 6, 2022; Inventor Bullington, Gregory J. et al.; 22 pages.
U.S. Appl. No. 17/710,411, Non-Final Office Action mailed Jul. 6, 2022; Inventor Bullington, Gregory J. et al.; 22 pages.
U.S. Appl. No. 17/863,605, Non-Final Office Action mailed Nov. 28, 2023; Inventor Bullington, Gregory J. et al.; 15 pages.
U.S. Appl. No. 18/130,207, Non-Final Office Action mailed Aug. 21, 2023; Inventor Bullington, Gregory J. et al.; 7 pages.
U.S. Appl. No. 18/209,327, Non-Final Office Action mailed Dec. 16, 2025; Inventor Patton, Richard G.; 19 pages.
U.S. Appl. No. 18/227,185, Final Office Action mailed Oct. 31, 2024; Inventor Bullington, Gregory J. et al.; 17 pages.
U.S. Appl. No. 18/227,185, Non-Final Office Action mailed Apr. 18, 2024; Inventor Bullington, Gregory J. et al.; 18 pages.
U.S. Appl. No. 18/240,178, Non-Final Office Action mailed Feb. 27, 2025; Inventor Bullington, Gregory J. et al.; 12 pages.
U.S. Appl. No. 18/240,178, Non-Final Office Action mailed Jun. 12, 2024; Inventor Bullington, Gregory J. et al.; 16 pages.
U.S. Appl. No. 18/242,900, Non-Final Office Action mailed Oct. 23, 2025; Inventor Bullington, Gregory J. et al.; 12 pages.
U.S. Appl. No. 18/243,540, Non-Final Office Action mailed Jun. 4, 2025; Inventor Bullington, Gregory J. et al.; 34 pages.
U.S. Appl. No. 18/299,680, Non-Final Office Action mailed Aug. 15, 2023; Inventor Bullington, Gregory J. et al.; 5 pages.
U.S. Appl. No. 18/380,259, Non-Final Office Action mailed Jan. 29, 2024; Inventor Bullington, Gregory J. et al.; 33 pages.
U.S. Appl. No. 18/380,259, Non-Final Office Action mailed Oct. 16, 2024; Inventor Bullington, Gregory J. et al.; 15 pages.
U.S. Appl. No. 18/381,369, Non-Final Office Action mailed Nov. 28, 2023; Inventor Bullington, Gregory J. et al.; 16 pages.
U.S. Appl. No. 18/399,007, Non-Final Office Action mailed Mar. 7, 2024; Inventor Bullington, Gregory J. et al.; 8 pages.
U.S. Appl. No. 18/407,010, Final Office Action mailed Sep. 6, 2024; Inventor Bullington, Gregory J. et al.; 11 pages.

(56) References Cited

OTHER PUBLICATIONS

U.S. Appl. No. 18/407,010, Non-Final Office Action mailed Dec. 4, 2025; Inventor Bullington, Gregory J. et al.; 7 pages.
U.S. Appl. No. 18/407,010, Non-Final Office Action mailed Mar. 13, 2024; Inventor Bullington, Gregory J. et al.; 8 pages.
U.S. Appl. No. 18/675,824, Non-Final Office Action mailed Jul. 26, 2024; Inventor Bullington, Gregory J. et al.; 13 pages.
U.S. Appl. No. 18/676,186, Non-Final Office Action mailed Aug. 5, 2024; Inventor Bullington, Gregory J. et al.; 13 pages.
U.S. Appl. No. 18/680,331, Final Office Action mailed Nov. 24, 2025; Inventor Bullington, Gregory J. et al.; 9 pages.
U.S. Appl. No. 18/680,331, Non-Final Office Action mailed Mar. 25, 2025; Inventor Bullington, Gregory J. et al.; 8 pages.
U.S. Appl. No. 18/680,348, Final Office Action mailed Nov. 24, 2025; Inventor Bullington; Gregory J. et al.; 8 pages.
U.S. Appl. No. 18/680,348, Non-Final Office Action mailed Mar. 25, 2025; Inventor Bullington, Gregory J. et al.; 7 pages.
U.S. Appl. No. 18/680,377, Final Office Action mailed Nov. 25, 2025; Inventor Bullington, Gregory J., et al.; 14 pages.
U.S. Appl. No. 18/680,377, Non-Final Office Action mailed Mar. 26, 2025; Inventor Bullington, Gregory J. et al.; 12 pages.
U.S. Appl. No. 18/680,439, Final Office Action mailed Nov. 25, 2025; Inventor Bullington, Gregory J., et al.; 10 pages.
U.S. Appl. No. 18/680,439, Non-Final Office Action mailed Mar. 31, 2025; Inventor Bullington, Gregory J. et al.; 8 pages.
U.S. Appl. No. 18/680,466, Final Office Action mailed Aug. 20, 2025; Inventor Bullington, Gregory J. et al.; 10 pages.
U.S. Appl. No. 18/680,466, Non-Final Office Action mailed Dec. 30, 2024; Inventor Bullington, Gregory J. et al.; 7 pages.
U.S. Appl. No. 18/960,441, Non-Final Office Action mailed Jan. 17, 2025; Inventor Bullington, Gregory J. et al.; 8 pages.
U.S. Appl. No. 18/990,547, Non-Final Office Action mailed Jan. 31, 2025; Inventor Bullington, Gregory J. et al.; 10 pages.
U.S. Appl. No. 19/175,765, Final Office Action mailed Nov. 26, 2025; Inventor Bullington, Gregory J. et al.; 14 pages.
U.S. Appl. No. 19/175,765, Non-Final Office Action mailed Aug. 8, 2025; Inventor Bullington, Gregory J. et al.; 11 pages.
U.S. Appl. No. 19/353,350, Non-Final Office Action mailed Feb. 9, 2026; Inventor Bullington, Gregory et al.; 23 pages.
U.S. Appl. No. 90/015,399, Order Granting Request for Ex Parte Reexamination mailed Oct. 21, 2025; Inventor Bullington, Gregory J., et al.; 43 pages.
U.S. Appl. No. 10/039,483, Request for Ex Parte Reexamination of U.S. Appl. No. 10/039,483 Under 35 U.S.C § 302 and 37 CFR. § 1.510 filed Jul. 21, 2025, Inventor Bullington, Gregory J., et al.; 66 pages.
U.S. Appl. No. 90/019,177, Declaration of Dr. Erik K. Antonsson (Ph.D., P.E., Nae) in Ex Parte Reexamination dated Mar. 21, 2023; 137 pages.
U.S. Appl. No. 90/019,177, Declaration of Dr. Morten Jensen (Ph.D., Dr. Med., FAHA) under 37 CFR. § 1.132 in Ex Parte Reexamination dated Oct. 10, 2023; 55 pages.
U.S. Appl. No. 90/019,177, Final Office Action in Ex Parte Reexamination mailed Dec. 1, 2023; Inventor Bullington, Gregory J. et al.; 19 pages.
U.S. Appl. No. 90/019,177, Non-Final Office Action in Ex Parte Reexamination mailed Aug. 9, 2023; Inventor Bullington, Gregory J. et al.; 11 pages.
U.S. Appl. No. 90/019,177, Order Granting Request for Ex Parte Reexamination mailed Apr. 26, 2023, Inventor Bullington, Gregory J., et al.; 16 pages.
U.S. Appl. No. 90/019,177, Patent Trial and Appeal Board Decision in Ex Parte Reexamination mailed May 20, 2025, Inventor Bullington, Gregory J., et al.; 22 pages.
U.S. Appl. No. 90/019,177, Request for Ex Parte Reexamination of U.S. Appl. No. 10/039,483 Under 35 U.S.C § 302 and 37 CFR. § 1.510 filed Mar. 22, 2023; Inventor Bullington, Gregory J., et al.; 84 pages.
U.S. Appl. No. 90/019,177, "VENT" Definition & Meaning—Merriam-Webster (https://www.merriam-webster.com/dictionary/vent, accessed Mar. 21, 2023); 16 pages.
U.S. Appl. No. 90/019,177, "VENT," n.2: Oxford English Dictionary (https://www.oed.com/view/Entry/222207?&print, accessed Feb. 16, 2023); 12 pages.
U.S. Appl. No. 90/019,756, Declaration of Dr. Erik K. Antonsson (Ph. D., P.E., Nae) in Ex Parte Reexamination dated Dec. 5, 2024; 138 pages.
U.S. Appl. No. 90/019,756, Declaration of Dr. Morten Jensen (Ph.D., Dr. Med., FAHA) under 37 CFR. § 1.132 in Ex Parte Reexamination dated Feb. 10, 2026; 74 pages.
U.S. Appl. No. 90/019,756, Declaration of Dr. Morten Jensen (Ph.D., Dr. Med., FAHA) under 37 CFR. § 1.132 in Ex Parte Reexamination dated Oct. 1, 2025; 79 pages.
U.S. Appl. No. 90/019,756, Examiner Interview Summary in Ex Parte Reexamination mailed Sep. 17, 2025, Inventor Patton, Richard G.; 7 pages.
U.S. Appl. No. 90/019,756, Non-Final Office Action in Ex Parte Reexamination mailed Jun. 17, 2025; Inventor Patton, Richard G.; et al.; 38 pages.
U.S. Appl. No. 90/019,756, Non-Final Office Action in Ex Parte Reexamination mailed Nov. 10, 2025; Inventor Patton, Richard G.; 44 pages.
U.S. Appl. No. 90/019,756, Order Granting Request for Ex Parte Reexamination mailed Jan. 22, 2025, Inventor Patton, Richard G.; 14 pages.
U.S. Appl. No. 10/052,053, Request for Ex Parte Reexamination of U.S. Appl. No. 10/052,053 Under 35 U.S.C § 302 and 37 CFR. § 1.510 filed Dec. 6, 2024, Inventor Patton, Richard G.; 144 pages.
U.S. Appl. No. 90/019,757, Declaration of Dr. Erik K. Antonsson (Ph. D., P.E., Nae) in Ex Parte Reexamination dated Dec. 5, 2024; 141 pages.
U.S. Appl. No. 90/019,757, Declaration of Dr. Morten Jensen (Ph.D., Dr.Med., FAHA) under 37 CFR. § 1.132 in Ex Parte Reexamination dated Oct. 1, 2025; 61 pages.
U.S. Appl. No. 90/019,757, Examiner Interview Summary in Ex Parte Reexamination mailed Sep. 17, 2025, Inventor Patton, Richard G.; 7 pages.
U.S. Appl. No. 90/019,757, Final Office Action in Ex Parte Reexamination mailed Nov. 28, 2025, Inventor Patton, Richard G.; 46 pages.
U.S. Appl. No. 90/019,757, Non-Final Office Action in Ex Parte Reexamination mailed Jun. 17, 2025, Inventor Patton, Richard G.; 27 pages.
U.S. Appl. No. 90/019,757, Order Granting Request for Ex Parte Reexamination mailed Jan. 27, 2025, Inventor Patton, Richard G.; 15 pages.
U.S. Appl. No. 90/019,757, Request for Ex Parte Reexamination of U.S. Pat. No. 9855002 Under 35 U.S.C § 302 and 37 CFR. § 1.510 filed Dec. 6, 2024, Inventor Patton, Richard G.; 147 pages.
U.S. Appl. No. 90/019,823, Declaration of Dr. Erik K. Antonsson (Ph. D., P.E., Nae) in Ex Parte Reexamination dated Jan. 20, 2025; 164 pages.
U.S. Appl. No. 90/019,823, Declaration of Dr. Morten Jensen (Ph.D., Dr. Med., FAHA) under 37 CFR. § 1.132 in Ex Parte Reexamination dated Nov. 25, 2025; 75 pages.
U.S. Appl. No. 90/019,823, Examiner Interview Summary in Ex Parte Reexamination mailed Nov. 25, 2025, Inventor Bullington, Gregory J.; 31 pages.
U.S. Appl. No. 90/019,823, Non-Final Office Action in Ex Parte Reexamination mailed Aug. 25, 2025, Inventor Bullington, Gregory J. et al.; 30 pages.
U.S. Appl. No. 90/019,823, Order Granting Request for Ex Parte Reexamination mailed Feb. 24, 2025, Inventor Bullington, Gregory J. et al.; 16 pages.
U.S. Appl. No. 11/529,081, Request for Ex Parte Reexamination of U.S. Appl. No. 11/529,081 Under 35 U.S.C § 302 and 37 CFR. § 1.510 filed Jan. 21, 2025, Inventor Bullington, Gregory J., et al.; 179 pages.
U.S. Appl. No. 90/019,823, Response to Non-Final Office Action in Ex Parte Reexamination filed Nov. 25, 2025; Inventor Bullington, Gregory J.; 211 pages.

(56) References Cited

OTHER PUBLICATIONS

U.S. Appl. No. 90/019,824, Declaration of Dr. Erik K. Antonsson (Ph. D., P.E., Nae) in Ex Parte Reexamination dated Jan. 20, 2025; 161 pages.
U.S. Appl. No. 90/019,824, Declaration of Dr. Morten Jensen (Ph.D., Dr. Med., FAHA) under 37 CFR. § 1.132 in Ex Parte Reexamination dated Feb. 3, 2026; 80 pages.
U.S. Appl. No. 90/019,824, Examiner Interview Summary in Ex Parte Reexamination mailed Jan. 29, 2026; Inventor Bullington, Gregory J., et al.; 3 pages.
U.S. Appl. No. 90/019,824, Non-Final Office Action in Ex Parte Reexamination mailed Nov. 4, 2025; Inventor Bullington, Gregory J., et al.; 22 pages.
U.S. Appl. No. 90/019,824, Order Granting Request for Ex Parte Reexamination mailed Feb. 24, 2025, Inventor Bullington, Gregory J., et al.; 18 pages.
U.S. Appl. No. 11/903,709, Request for Ex Parte Reexamination of U.S. Appl. No. 11/903,709 Under 35 U.S.C § 302 and 37 CFR. § 1.510 filed Jan. 21, 2025, Inventor Bullington, Gregory J., et al.; 176 pages.
U.S. Appl. No. 90/019,825, Declaration of Dr. Erik K. Antonsson (Ph. D., P.E., Nae) in Ex Parte Reexamination dated Jan. 20, 2025; 169 pages.
U.S. Appl. No. 90/019,825, Declaration of Dr. Morten Jensen (Ph.D., Dr.Med., FAHA) under 37 CFR. § 1.132 in Ex Parte Reexamination dated Feb. 16, 2026; 84 pages.
U.S. Appl. No. 90/019,825, Examiner Interview Summary in Ex Parte Reexamination mailed Jan. 29, 2026, Inventor Bullington, Gregory J. et al.; 3 pages.
U.S. Appl. No. 90/019,825, Non-Final Office Action in Ex Parte Reexamination mailed Nov. 17, 2025, Inventor Bullington, Gregory J., et al.; 25 pages.
U.S. Appl. No. 90/019,825, Order Granting Request for Ex Parte Reexamination mailed Feb. 25, 2025, Inventor Bullington, Gregory J., et al.; 15 pages.
U.S. Appl. No. 90/019,825, Request for Ex Parte Reexamination of U11653863 Under 35 U.S.C § 302 and 37 CFR. § 1.510 filed Jan. 21, 2025, Inventor Bullington, Gregory J., et al.; 180 pages.
Valleywise Health Medical Center Case Study "In anticipation of CMS changes, AZ hospital identifies solution to blood culture contaminations with new Kurin Jet™," Brochure; 1 page (Publication Date Unknown).
Widmer, A.F, et al.; "Sterilization of skin and catheters before drawing blood cultures," J Clin Microbiol .; 41(10):4910; 1 page (Oct. 2003).
Wilber, E.P., et al.; "Effect of an initial specimen diversion device on blood-culture contamination rates and vancomycin usage: A quasi-experimental study," Epub Aug. 3, 2023; Infect Control Hosp Epidemiol.; 45(1): 100-102 (Jan. 2024).
Zimmerman et al., "Reducing Blood Culture Contamination Using an Initial Specimen Diversion Device," Am. J. Infection Control, vol. 47, No. 7, pp. 822-826 (Jan. 2019).
Zwang, O., et al.; "Analysis of strategies to improve cost effectiveness of blood cultures," J Hosp Med.; 1(5):272-276. doi: 10.1002/jhm. 115 (Sep. 2006).

* cited by examiner

FLUID CONTROL DEVICES AND METHODS OF USING THE SAME

CROSS-REFERENCE TO RELATED APPLICATIONS

This application is a continuation of U.S. patent application Ser. No. 16/213,005 entitled, "Fluid Control Devices and Methods of Using the Same," filed Dec. 7, 2018, which claims priority to and the benefit of U.S. Provisional Patent Application Ser. No. 62/687,951 entitled, "Fluid Control Devices and Methods of Using the Same," filed Jun. 21, 2018 and U.S. Provisional Patent Application Ser. No. 62/595,871 entitled, "Fluid Control Devices and Methods of Using the Same," filed Dec. 7, 2017, the disclosure of each of which is incorporated herein by reference in its entirety.

BACKGROUND

The invention relates generally to the parenteral procurement of bodily fluid samples, and more particularly to fluid diversion, sequestration, and/or isolation devices and methods for procuring bodily fluid samples with reduced contaminants such as dermally residing microbes and/or other contaminants exterior to the bodily fluid source.

Health care practitioners routinely perform various types of microbial as well as other broad diagnostic tests on patients using parenterally obtained bodily fluids. As advanced diagnostic technologies evolve and improve, the speed, accuracy (both sensitivity and specificity), and value of information that can be provided to clinicians continues to improve. Maintaining the integrity of the bodily fluid sample during and/or after collection also ensures that analytical diagnostic results are representative of the the in vivo conditions of a patient. Examples of diagnostic technologies that are reliant on high quality, non-contaminated, and/or unadulterated bodily fluid samples include but are not limited to microbial detection, molecular diagnostics, genetic sequencing (e.g., deoxyribonucleic acid (DNA), ribonucleic acid (RNA), next-generation sequencing (NGS), etc.), biomarker identification, and the like. When biological matter, which can include cells external to the intended source for sample procurement, and/or other external contaminants are inadvertently included in the bodily fluid sample that is to be analyzed, there is an opportunity for inaccurate test results to be derived. In short, when the purity of the sample intended to be derived or collected from a specific bodily fluid source is compromised during the specimen procurement process, resultant analytical test results may be inaccurate, distorted, adulterated, falsely positive, falsely negative, and/or otherwise not representative of the actual condition of the patient, which in turn, can inform faulty, inaccurate, confused, unsure, low-confidence, and/or otherwise undesired clinical decision making.

In some instances, patient samples (e.g., bodily fluids) are tested for the presence of one or more potentially undesirable microbes, such as bacteria, fungi, or yeast (e.g., *Candida*). In some instances, microbial testing may include incubating patient samples in one or more sterile and/or non-sterile vessels that may contain culture media, common additives, and/or other types of solutions that are conducive to microbial growth. In other instances, the sample in the vessel may be analyzed directly (i.e., not incubated) and may not contain culture media or additives associated with incubating the specimen. In still other instances, various technologies can be employed to assist in the detection of the presence of microbes as well as other types of biological matter, specific types of cells, biomarkers, proteins, antigens, enzymes, blood components, and/or the like during diagnostic testing. Examples include but are not limited to molecular polymerase chain reaction (PCR), magnetic resonance and other magnetic analytical platforms, automated microscopy, spatial clone isolation, flow cytometry, whole blood ("culture free") specimen analysis (e.g. NGS) and associated technologies, morphokinetic cellular analysis, and/or other common or evolving and advanced technologies utilized in the clinical laboratory environment to characterize patient specimens and/or to detect, identify, type, categorize, and/or characterize specific organisms, antibiotic susceptibilities, and/or the like.

In some instances, the detection of the presence of microbes includes allowing the microbes and/or organisms to grow for an amount of time (e.g., a variable amount of time from less than an hour to a few hours to several days—which can be longer or shorter depending on the diagnostic technology employed). The microbe and/or organism growth can then be detected by automated, continuous monitoring, and/or other methods specific to the analytical platform and technology used for detection, identification, and/or the like.

In culture testing, for example, when microbes are present in the patient sample, the microbes flourish over time in the culture medium and, in some instances, automated monitoring technologies can detect carbon dioxide produced by organism growth. The presence of microbes in the culture medium (as indicated by observation of carbon dioxide and/or via other detection methods) suggests the presence of the same microbes in the patient sample which, in turn, suggests the presence of the same microbes in the bodily fluid of the patient from whom the sample was obtained. Accordingly, when microbes are determined to be present in the culture medium (or more generally in the sample used for testing), the patient may be diagnosed and prescribed one or more antibiotics or other treatments specifically designed to treat or otherwise remove the undesired microbes from the patient.

Patient samples, however, can become contaminated during procurement and/or otherwise can be susceptible to false positive or false negative results. For example, microbes from a bodily surface (e.g., dermally residing microbes) that are dislodged during the specimen procurement process (which can include needle insertion into a patient, specimen procurement via a lumen-containing device such as a peripheral IV catheter (NV), a central line (PICC) and/or other indwelling catheter(s), collection with a syringe or any other suitable means employed to collect a patient specimen), either directly or indirectly via tissue fragments, hair follicles, sweat glands, and other skin adnexal structures, can be subsequently transferred to a culture medium, test vial, or other suitable specimen collection or transfer vessel with the patient sample and/or included in the specimen that is to be analyzed for non-culture based testing. Another possible source of contamination is from the person drawing the patient sample (e.g., a doctor, phlebotomist, nurse, technician, etc.). Specifically, equipment, supplies, and/or devices used during a patient sample procurement process often include multiple fluidic interfaces (by way of example, but not limited to, patient to needle, needle to transfer adapter, transfer adapter to sample vessel, catheter hub to syringe, syringe to transfer adapter, needle/tubing to sample vessels, and/or any other fluidic interface or any combination thereof) that can each introduce points of potential contamination. In some instances, such contaminants may thrive in a culture medium and/or may be identified by another non-culture based diagnostic technology and eventually may yield a false positive and/or a false negative microbial test result, which may inaccurately reflect the presence or lack of such microbes within the patient (i.e., in vivo).

Such inaccurate results because of contamination and/or other sources of adulteration that compromise the purity of the sample are a concern when attempting to diagnose or treat a wide range of suspected illnesses, diseases, infections, patient conditions or other maladies of concern. For example, false negative results from microbial tests may result in a misdiagnosis and/or delayed treatment of a patient illness, which, in some cases, could result in the death of the patient. Conversely, false positive results from microbial tests may result in the patient being unnecessarily subjected to one or more anti-microbial therapies, which may cause serious side effects to the patient including, for example, death, as well as produce an unnecessary burden and expense to the health care system due to extended length of patient stay and/or other complications associated with erroneous treatments. The use of diagnostic imaging equipment attributable to these false positive results is also a concern from both a cost as well as patient safety perspective as unnecessary exposure to concentrated radiation associated with a variety of imaging procedures (e.g., CT scans) has many known adverse impacts on long-term patient health.

In some instances, devices and/or systems can be used to reduce the likelihood of contamination, adulteration, and/or the like of bodily fluid samples for testing. For example, some known devices can be configured to collect, divert, separate, and/or isolate or sequester an initial volume of bodily fluid that may be more likely to contain contaminants such as dermally residing microbes or the like. Some such devices, however, can be cumbersome, non-intuitive, perceived as difficult to use, inappropriate or unusable as intended for the target patient population, etc. In addition, some such devices can require training, user observation, intervention by more than one user, and/or can otherwise present challenges that can lead to limited efficacy based on variables including environmental, educational, clinician skill, patient condition, and/or the like. In some instances, such challenges can complicate the collection of consistently high quality samples that are non-contaminated, sterile, unadulterated, etc., which in turn, can impact the validity of test result outcomes.

As such, a need exists for fluid diversion devices and methods for procuring bodily fluid samples with reduced contaminants such as dermally residing microbes and/or other contaminants exterior to the bodily fluid source. Furthermore, a need exists for such devices that are user-friendly, utilize little to no user-intervention and/or actuation, demonstrate consistent efficacy, and address the challenges associated with collecting samples from patients with challenging health circumstances and/or physical characteristics that impact the ability to collect bodily fluid samples.

SUMMERY

Devices and methods for procuring bodily fluid samples with reduced contaminants such as dermally residing microbes and/or other contaminants exterior to the bodily fluid source are described herein. In some embodiments, an apparatus includes a housing and an actuator. The housing has an inlet configured to be placed in fluid communication with a bodily fluid source, an outlet configured to be placed in fluid communication with a fluid collection device, and a sequestration portion configured to receive an initial volume of bodily fluid. The actuator defines at least one fluid flow path configured to direct a flow of bodily fluid through at least a portion of the housing. The actuator is configured in a first state to establish fluid communication between the sequestration portion and the outlet with the at least one fluid flow path. The outlet is configured to transition from a closed state to an open state when the actuator is in the first state to vent the sequestration portion via the at least one fluid flow path and the outlet. The actuator is configured to transition from the first state to a second state after venting the sequestration portion such that the at least one fluid flow path establishes fluid communication between the sequestration portion and the inlet to allow the initial volume of bodily fluid to transfer into the sequestration portion. The actuator is configured to transition from the second state to a third state after the initial volume of bodily fluid is transferred into the sequestration portion to (1) sequester the initial volume of bodily fluid in the sequestration portion and (2) place the outlet in fluid communication with the inlet via the at least one fluid flow path to allow a subsequent volume of bodily fluid to be transferred to the fluid collection device when the fluid collection device is coupled to the outlet and the outlet is in the open state.

DETAILED DESCRIPTION

Figure 1:
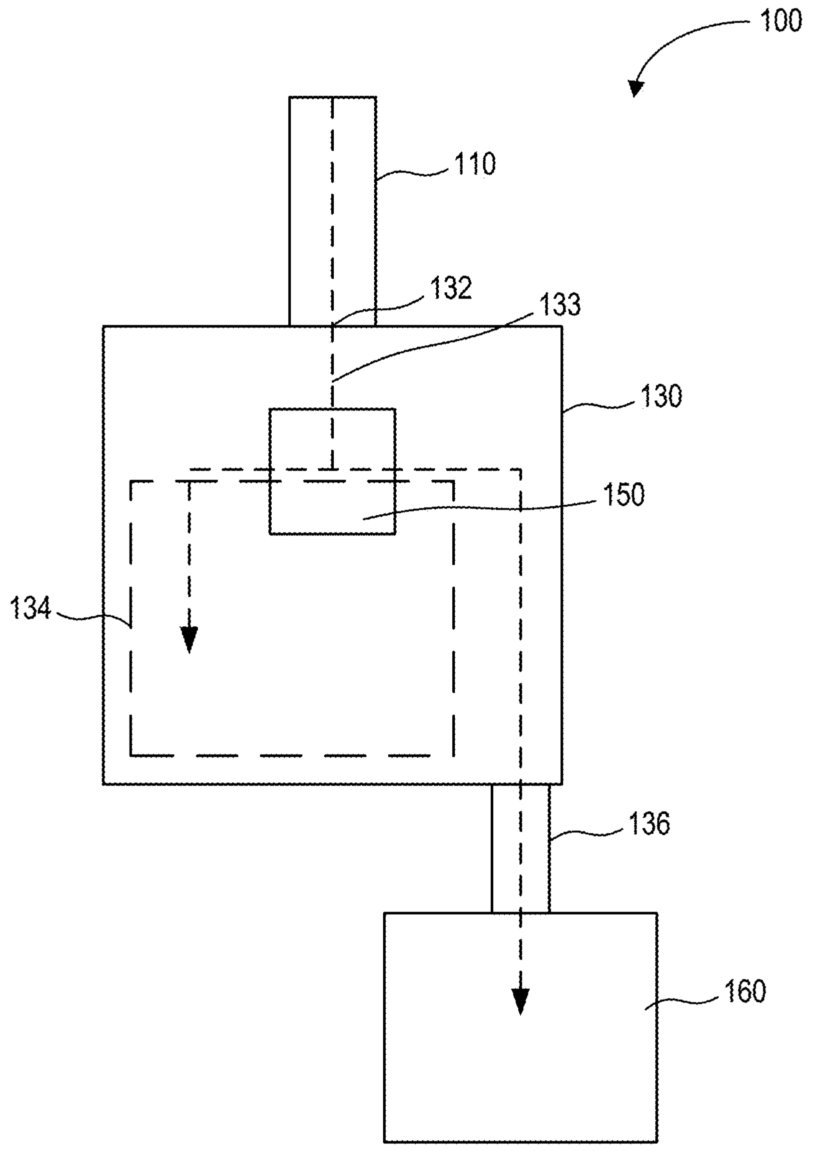
FIG. 1 is a schematic illustration of a fluid control device according to an embodiment.

Devices and methods for collecting, diverting, directing, sequestering, isolating, etc. an initial volume of bodily fluid to reduce contamination in subsequently procured bodily fluid samples are described herein. Any of the fluid control devices described herein can be configured to receive, procure, and/or transfer a flow, bolus, volume, etc., of bodily fluid. A first reservoir, channel, flow path, or portion of the device can receive an initial amount of the bodily fluid flow, which then can be substantially or fully sequestered (e.g., contained or retained, circumvented, isolated, segregated, vapor-locked, separated, and/or the like) in or by the first reservoir or first portion of the device. In some instances, contaminants such as dermally residing microbes or the like can be included and/or entrained in the initial amount of the bodily fluid and likewise are sequestered in or by the first reservoir or first portion of the device. Once the initial amount is sequestered, any subsequent amount of the bodily fluid flow can be diverted, channeled, directed, flow controlled (e.g., manually, automatically, and/or semi-automatically) to a second reservoir, second portion of the device, and/or any additional flow path(s). Thus, with the initial amount sequestered, any additional and/or subsequent amount(s) of bodily fluid flow are substantially free from contaminants that may otherwise produce inaccurate, distorted, adulterated, falsely positive, falsely negative, etc., results in some diagnostics and/or testing. In some instances, the initial amount of bodily fluid also can be used, for example, in other testing such as those less affected by the presence of contaminants, can be discarded as a waste volume, can be infused back into the patient, and/or can be used for any other suitable clinical application.

In some embodiments, a feature of the fluid control devices and/or methods described herein is the use of an external negative pressure source (e.g., provided by a fluid collection device or any other suitable means) to (1) overcome physical patient challenges which can limit and/or prevent a sufficient pressure differential (e.g., a differential in blood pressure to ambient air pressure) to fully engage the sequestration and/or diversion portion and/or to transition fluid flow to the fluid collection device; (2) result in proper filling of the sequestration and/or diversion portion with a clinically validated and/or desirable volume of bodily fluid; (3) result in efficient, timely, and/or user-accepted consistency with bodily fluid collection process; and/or (4) provide a means of manipulating and/or automatically transitioning fluid flow (e.g., movement of physical components of the system or changing, switching, engaging, and/or otherwise employing or achieving desired fluid flow dynamics) to enable sequestration and/or isolation of the initial sample and collection of a subsequent sample.

In some embodiments, an apparatus includes a housing and an actuator. The housing has an inlet configured to be placed in fluid communication with a bodily fluid source, an outlet configured to be placed in fluid communication with a fluid collection device, and a sequestration portion configured to receive an initial volume of bodily fluid. The actuator defines at least one fluid flow path configured to direct a flow of bodily fluid through at least a portion of the housing. The actuator is configured in a first state to establish fluid communication between the sequestration portion and the outlet with the at least one fluid flow path. The outlet is configured to transition from a closed state to an open state when the actuator is in the first state to vent the sequestration portion via the at least one fluid flow path and the outlet. The actuator is configured to transition from the first state to a second state after venting the sequestration portion such that the at least one fluid flow path establishes fluid communication between the sequestration portion and the inlet to allow the initial volume of bodily fluid to transfer into the sequestration portion. The actuator is configured to transition from the second state to a third state after the initial volume of bodily fluid is transferred into the sequestration portion to (1) sequester the initial volume of bodily fluid in the sequestration portion and (2) place the outlet in fluid communication with the inlet via the at least one fluid flow path to allow a subsequent volume of bodily fluid to be transferred to the fluid collection device when the fluid collection device is coupled to the outlet and the outlet is in the open state.

In some embodiments, an apparatus includes an inlet member coupled to a housing, an outlet member coupled to the housing, and a sequestration portion formed at least in part by the housing. The inlet member defines a lumen that is in fluid communication with a fluid flow path defined by the housing and is configured to be placed in fluid communication with a bodily fluid source. The outlet member defines a lumen that is in fluid communication with the fluid flow path defined by the housing and is configured to be placed in fluid communication with a fluid collection device. The sequestration portion is in fluid communication with the fluid flow path defined by the housing and is configured to deform from a first state to a second state in response to a force exerted on a portion of the housing to vent the sequestration portion. The sequestration portion configured to transition from the second state to the first state in response to removal of the force to generate suction within the sequestration portion to draw an initial volume of bodily fluid through the lumen of the inlet member and the fluid flow path, and into the sequestration portion.

In some embodiments, a method of using a fluid control device to obtain a bodily fluid sample with reduced contamination includes exerting a force to deform a sequestration portion of the fluid control device and venting the sequestration portion as a result of the deforming of the sequestration portion. Fluid communication is established between a bodily fluid source and an inlet member of the fluid control device. The force exerted on the sequestration portion is removed to generate suction within the sequestration portion. In response to the suction, an initial volume of bodily fluid is transferred from the bodily fluid source, through the inlet member, and to the sequestration portion. As a result of the initial volume of bodily fluid being disposed in the sequestration portion, a subsequent volume of bodily fluid is transferred from the bodily fluid source, through the inlet member, and to an outlet member in fluid communication with the inlet member.

In some embodiments, a fluid control device includes an inlet and an outlet. The inlet is configured to be placed in fluid communication with a bodily fluid source or an intermediary bodily fluid transfer device and the outlet is configured to be placed in fluid communication with a fluid collection device (e.g., a sample bottle, container, reservoir, syringe, evacuated container, dish, vial, lumen-containing device, and/or any other suitable bodily fluid collection and/or transfer device). In some embodiments, the fluid control device has a first state in which an initial volume of bodily fluid can flow from the inlet to a sequestration and/or diversion portion of the fluid control device (which can be formed by or in the fluid control device or coupled thereto) and a second state in which (1) the initial volume is sequestered in the sequestration and/or diversion portion of the fluid control device, and (2) a subsequent volume of bodily fluid, being substantially free of contaminants, can flow from the bodily fluid source, through at least a portion of the fluid control device, and into the fluid collection device. The fluid control device is configured to automatically transition from the first state to the second state or to transition in response to an actuation of a portion of the fluid control device after the sequestration and/or diversion portion receives the initial volume.

As used in this specification and the claims, the singular forms “a,” “an” and “the” include plural referents unless the context clearly dictates otherwise. Thus, for example, the term “a member” is intended to mean a single member or a combination of members, “a material” is intended to mean one or more materials, or a combination thereof.

As used herein, the terms “about,” “approximate,” and/or “substantially” when used in connection with stated value and/or other geometric relationships is intended to convey that the structure so defined is nominally the value stated and/or the geometric relationship described. In some instances, the terms “about,” “approximately,” and/or “substantially” can generally mean and/or can generally contemplate plus or minus 10% of the value or relationship stated. For example, about 0.01 would include 0.009 and 0.011, about 0.5 would include 0.45 and 0.55, about 10 would include 9 to 11, and about 1000 would include 900 to 1100. While a value stated may be desirable, it should be understood that some variance may occur as a result of, for example, manufacturing tolerances or other practical considerations (such as, for example, the pressure or force applied through a portion of a device, conduit, lumen, etc.). Accordingly, the terms “about,” “approximately,” and/or “substantially” can be used herein to account for such tolerances and/or considerations.

As used herein, “bodily fluid” can include any fluid obtained directly or indirectly from a body of a patient. For example, “bodily fluid” includes, but is not limited to, blood, cerebrospinal fluid, urine, bile, lymph, saliva, synovial fluid, serous fluid, pleural fluid, amniotic fluid, mucus, sputum, vitreous, air, and the like, or any combination thereof.

As used herein, the words “proximal” and “distal” refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As described in further detail herein, any of the devices and methods can be used to procure bodily fluid samples with reduced contamination by, for example, diverting a “pre-sample” volume of bodily fluid prior to collecting a “sample” volume of bodily fluid. Each of the terms “pre-sample,” “first,” and/or “initial,” can be used interchangeably to describe and/or refer to an amount, portion, or volume of bodily fluid that is transferred, diverted, and/or sequestered prior to procuring the “sample” volume. In some embodiments, the terms “pre-sample,” “first,” and/or “initial” can refer to a predetermined, defined, desired, or given volume, portion, or amount of bodily fluid. For example, in some embodiments, a predetermined and/or desired pre-sample volume of bodily fluid can be about 0.1 milliliter (mL), about 0.2 mL, about 0.3 mL, about 0.4 mL, about 0.5 mL, about 1.0 mL, about 2.0 mL, about 3.0 mL, about 4.0 mL, about 5.0 mL, about 10.0 mL, about 20 mL, about 50 mL, and/or any volume or fraction of a volume therebetween. In other embodiments, the pre-sample volume can be greater than 50 mL or less than 0.1 mL. In some specific embodiments, a predetermined and/or desired pre-sample volume can be between about 0.1 mL and about 5.0 mL. In other embodiments, the pre-sample volume can be, for example, a drop of bodily fluid, a few drops of bodily fluid, a combined volume of any number of lumen that form, for example, a flow path (or portion thereof) from the bodily fluid source to an initial collection chamber, portion, reservoir, etc. (e.g., a sequestration chamber).

On the other hand, the terms “sample,” “second,” and/or “subsequent” when used in the context of a volume of bodily fluid can refer to a volume, portion, or amount of bodily fluid that is either a random volume or a predetermined or desired volume of bodily fluid collected after transferring, diverting, sequestering, and/or isolating the pre-sample volume of bodily fluid. For example, in some embodiments, a desired sample volume of bodily fluid can be about 10 mL to about 60 mL. In other embodiments, a desired sample volume of bodily fluid can be less than 10 mL or greater than 60 mL. In some embodiments, for example, a sample volume can be at least partially based on one or more tests, assays, analyses, and/or processes to be performed on the sample volume.

The embodiments described herein can be configured to selectively transfer bodily fluid to one or more fluid collection device(s). In some embodiments, a fluid collection device can include, but is not limited to, any suitable vessel, container, reservoir, bottle, adapter, dish, vial, syringe, device, diagnostic and/or testing machine, and/or the like. By way of specific example, in some instances, any of the embodiments and/or methods described herein can be used to transfer a sample volume into a sample reservoir such as any of those described in detail in U.S. Pat. No. 8,197,420 entitled, “Systems and Methods for Parenterally Procuring Bodily-Fluid Samples with Reduced Contamination,” filed Dec. 13, 2007 (“the ’420 Patent”), the disclosure of which is incorporated herein by reference in its entirety.

In some embodiments, a sample reservoir can be a sample or culture bottle such as, for example, an aerobic culture bottle or an anaerobic culture bottle. In this manner, the culture bottle can receive a bodily fluid sample, which can then be tested (e.g., via in vitro diagnostic (VD) tests, and/or any other suitable test) for the presence of, for example, Gram-Positive bacteria, Gram-Negative bacteria, yeast, fungi, and/or any other organism. In some instances, the culture bottle can receive a bodily fluid sample and the culture medium (disposed therein) can be tested for the presence of any suitable organism. If such a test of the culture medium yields a positive result, the culture medium can be subsequently tested using a PCR-based system to identify a specific organism. Moreover, as described in further detail herein, in some instances, diverting a pre-sample or initial volume of bodily fluid can reduce and/or substantially eliminate contaminants in the bodily fluid sample that may otherwise lead to inaccurate test results.

Any of the sample containers, reservoirs, bottles, dishes, vials, etc., described herein can be devoid of contents prior to receiving a sample volume of bodily fluid or can include, for example, any suitable additive, culture medium, substances, enzymes, oils, fluids, and/or the like. For example, in some embodiments, a sample reservoir can include an aerobic or anaerobic culture medium (e.g., a nutrient rich and/or environmentally controlled medium to promote growth, and/or other suitable medium(s)), which occupies at least a portion of the inner volume defined by the sample reservoir. In some embodiments, a sample reservoir can include, for example, any suitable additive or the like such as, heparin, citrate, ethylenediaminetetraacetic acid (EDTA), oxalate, SPS, and/or the like, which similarly occupies at least a portion of the inner volume defined by the sample reservoir. In other embodiments, a sample reservoir can be any suitable container used to collect a specimen.

While the term "culture medium" can be used to describe a substance configured to react with organisms in a bodily fluid (e.g., microorganisms such as bacteria) and the term "additive" can be used to describe a substance configured to react with portions of the bodily fluid (e.g., constituent cells of blood, serum, synovial fluid, etc.), it should be understood that a sample reservoir can include any suitable substance, liquid, solid, powder, lyophilized compound, gas, etc. Moreover, when referring to an "additive" within a sample reservoir, it should be understood that the additive could be a culture medium, such as an aerobic culture medium and/or an anaerobic culture medium contained in a culture bottle, an additive and/or any other suitable substance or combination of substances contained in a culture bottle and/or any other suitable reservoir such as those described above. That is to say, the embodiments described herein can be used with any suitable fluid reservoir or the like containing any suitable substance. Furthermore, any of the embodiments and/or methods described herein can be used to transfer a volume of bodily fluid to a reservoir (or the like) that does not contain a culture medium, additive, and/or any other substance prior to receiving a flow of bodily fluid.

While some of the embodiments are described herein as being used for procuring bodily fluid for one or more culture sample testing, it should be understood that the embodiments are not limited to such a use. Any of the embodiments and/or methods described herein can be used to transfer a flow of bodily fluid to any suitable device that is placed in fluid communication therewith. Thus, while specific examples are described herein, the devices, methods, and/or concepts are not intended to be limited to such specific examples. Moreover, a sample collected through the use of any of the devices described herein can be used in any suitable testing such as those described above.

The embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (TWA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polyesters, poly carbonates, polyacrylates, polymers of ethylene-vinyl acetates and other acyl substituted cellulose acetates, non-degradable polyurethanes, polystyrenes, polyvinyl chloride, polyvinyl fluoride, polyvinyl imidazole), chlorosulphonate polyolefins, polyethylene oxide, and/or blends and copolymers thereof.

The embodiments described herein and/or portions thereof can include components formed of one or more parts, features, structures, etc. When referring to such components it should be understood that the components can be formed by a singular part having any number of sections, regions, portions, and/or characteristics, or can be formed by multiple parts or features. For example, when referring to a structure such as a wall or chamber, the structure can be considered as a single structure with multiple portions, or multiple, distinct substructures or the like coupled to form the structure. Thus, a monolithically constructed structure can include, for example, a set of substructures. Such a set of substructures may include multiple portions that are either continuous or discontinuous from each other. A set of substructures can also be fabricated from multiple items or components that are produced separately and are later joined together (e.g., via a weld, an adhesive, a snap, and/or any suitable method).

Referring now to the drawings, FIG. 1 is a schematic illustration of a fluid control device 100 according to an embodiment. Generally, the fluid control device 100 (also referred to herein as "control device" or "device") is configured to withdrawal bodily fluid from a patient. A first portion or amount (e.g., an initial amount) of the withdrawn bodily fluid is sequestered from a second portion or amount (e.g., a subsequent amount) of the withdrawn bodily fluid. In some instances, the first portion or amount can be subsequently used for additional testing (e.g., testing not sensitive to potential contaminants), discarded, and/or reinfused into the patient. In this manner, contaminants or the like can be sequestered within the first portion or amount of bodily, fluid, leaving the second portion or amount of bodily fluid substantially free of contaminants. The second portion or amount of bodily fluid can then be used as a biological sample in one or more tests for the purpose of medical diagnosis and/or treatment (e.g., a blood culture test or the like), as described in more detail herein. The first portion or amount of bodily fluid can be discarded as waste or can be used in any suitable test that is less likely to produce false, inaccurate, distorted, inconsistent, and unreliable results as a result of potential contaminants contained therein. In other instances, the first portion or amount of bodily fluid can be infused back into the patient.

The control device 100 includes an inlet device 110 and a housing 130 in fluid communication with and/or configured to be placed in fluid communication with the inlet device 110. The inlet device 110 can be any suitable device or set of devices configured to establish fluid communication between the housing 130 and a bodily fluid source such as, for example, the vasculature of a patient. For example, in some embodiments, the inlet device 110 can be an intravenous (IV) catheter, a needle, a peripherally inserted central catheter (PICC), a syringe, one or more pieces of sterile tubing, and/or any other suitable lumen-containing device. In other embodiments, the inlet device 110 can be a port or the like such as, for example, a Luer Lok®, or any other suitable coupler. In such embodiments, the inlet device 110 (e.g., port or coupler) can be configured to couple to an access device in fluid communication with a patient (e.g., a placed or indwelling IV catheter or needle). In some embodiments, the inlet device 110 can be integrally and/or monolithically formed with the housing 130 (e.g., the inlet device 110 can be disposed in and/or can form at least a part of the housing 130 or vice versa). In other embodiments, the inlet device 110 can be separate from the housing 130 and placed in fluid communication therewith via an intermediary lumen-containing device such as, for example, sterile tubing or the like. In some such embodiments, the inlet device 110 (or a portion thereof) can be configured to form a fluid tight connection, coupling, port; and/or seal with the housing 130 (or a portion thereof using any suitable connecting mechanism, for example, using tube fittings, couplings, and/or the like.

The housing 130 includes an inlet 132, at least one outlet 136, and a sequestration and/or diversion portion 134. In addition, the housing 130 defines one or more fluid flow paths 133 between the inlet 132 and the sequestration and/or diversion portion 134 and/or between the inlet 132 and the outlet 136. The housing 130 of the device 100 can be any suitable shape, size, and/or configuration. For example, in some embodiments, the housing 130 can be disposed in and/or can form at least a part of the inlet device 110. In such embodiments, any suitable portion of the housing 130 can be disposed in and/or can be formed by the inlet device 110 and vice versa. In other embodiments, the housing 130 can be formed separately from the inlet device 110 and can be physically and/or fluidically coupled to the inlet device 110. In some embodiments, the housing 130 can have a size that is at least partially based on a volume of bodily fluid at least temporarily stored, for example, in the sequestration and/or diversion portion 134.

The inlet 132 of the housing 130 is configured to be fluidically coupled to the inlet device 110 to place the housing 130 in fluid communication with a bodily fluid source such as, for example, the vasculature of a patient. As described above; in some embodiments, the inlet 132 of the housing 130 can be physically and fluidically coupled to the inlet device 110 via a lock, coupler, port, etc. In other embodiments, the inlet 132 can be in fluid communication with the inlet device 110 via a lumen-containing device such as, for example, sterile tubing or the like. In still other embodiments, the inlet 132 of the housing 130 can form and/or can be integrally or monolithically formed with the inlet device 110.

The one or more fluid flow paths 133 are configured to place the inlet 132 in fluid communication with the sequestration and/or diversion portion 134 and/or the outlet 136. In some embodiments, the one or more fluid flow paths 133 can be configured to control one or more parameters and/or characteristics associated with a fluid flow therethrough. For example, in some embodiments, the fluid flow path(s) 133 can have a length and/or width that corresponds to and/or is/are associated with a volume of bodily fluid to be conveyed therethrough. In some embodiments, the fluid flow path(s) 133 and/or a portion thereof can have a size, width, and/or diameter that is configured to modulate, increase, decrease, and/or otherwise control a pressure exerted through at least a portion of the fluid flow path(s) 133. In some embodiments, the modulation, increasing, decreasing, and/or controlling of pressures through one or more portions of the housing 130 and/or control device 100 can increase the likelihood of withdrawing a clinically meaningful volume of bodily fluid (e.g., without undesirable results such as damaging, collapsing, and/or "blowing" anatomical structures of the patient such as veins and/or the like). In other embodiments, the fluid flow path(s) 133 need not modulate pressure. Moreover, in some embodiments, the fluid flow path(s) 133 or portions thereof can be configured to at least temporarily hold, store, contain, and/or sequester at least a portion of the bodily fluid collected.

The sequestration and/or diversion portion 134 (also referred to herein as "sequestration portion") is at least temporarily placed in fluid communication with the inlet 132 via the fluid flow path(s) 133. As described in further detail herein, the sequestration portion 134 is configured to receive an initial flow and/or volume of bodily fluid from the inlet 132 while the housing 130 and/or control device 100 is in a first state or operating mode and in response to the housing 130 and/or control device 100 being transitioned to a second state or operating mode, can sequester (e.g., separate, segregate, contain, retain, isolate, etc.) the initial flow and/or volume of bodily fluid therein. In some embodiments, the sequestering of the initial flow and/or volume of bodily fluid can also sequester contaminants or the like, which in turn, reduces contaminants in subsequent volumes of bodily fluid withdrawn from the patient, as described in further detail herein.

The sequestration portion 134 can be any suitable shape, size, and/or configuration. For example, in some embodiments, the sequestration portion 134 can be at least partially formed by the housing 130. In other embodiments, the sequestration portion 134 can be a reservoir placed and/or disposed within a portion of the housing 130. In other embodiments, the sequestration portion 134 can be formed and/or defined by a portion of the fluid flow path 133. That is to say, the housing 130 can define one or more lumen and/or can include one or more lumen-defining device(s) configured to receive a flow of bodily fluid from the inlet 132, thereby defining the fluid flow path 133. In such embodiments, at least a portion of the lumen and/or a portion of the lumen-defining device(s) can form and/or can define the sequestration portion 134. Although the sequestration portion 134 is described above as being disposed in the housing 130, in other embodiments, the sequestration portion 134 can be defined or housed either partially or entirely within the inlet device 110. In such embodiments, at least a portion of the fluid flow path 133 can be disposed in and/or defined by the inlet device 110.

The sequestration portion 134, whether disposed in or formed by the housing 130 or the inlet device 110, is in fluid communication with the fluid flow path 133 and is configured to receive the initial volume or amount of bodily fluid withdrawn from a bodily fluid source, as described above. The sequestration portion 134 can have any suitable volume and/or fluid capacity. For example, in some embodiments, the sequestration portion 134 can have a volume and/or fluid capacity between about 0.25 ml and about 5.0 mL. In some embodiments, the sequestration portion 134 can have a volume measured in terms of an amount of bodily fluid (e.g., the initial or first amount of bodily fluid) configured to be transferred in the sequestration chamber 134. For example, in some embodiments, the sequestration chamber 134 can have a volume sufficient to receive an initial volume of bodily fluid as small as a microliter or less of bodily fluid (e.g., a volume as small as 20 drops of bodily fluid, 10 drops of bodily fluid, 5 drops of bodily fluid, a single drop of bodily fluid, or any suitable volume therebetween). In other embodiments, the sequestration portion 134 can have a volume sufficient to receive an initial volume of bodily fluid up to, for example, about 5.0 mL, 10.0 mL, 15 mL, 20 mL, 30 mL, 40 mL, 50 mL, or more. In some embodiments, the sequestration portion 134 can have a volume that is equal to, approximately equal to, and/or that is based at least in part on the volumes of a lumen of the inlet device 110, the lumen of the inlet 132 and a portion of the fluid flow path 133 defined between the inlet 132 and the sequestration portion 134, and/or any combination thereof. In other embodiments, the sequestration portion 134 can have a volume that is equal to and/or that is based at least in part on the individual and/or combined volumes of a portion of the inlet device 110, the inlet 132 of the housing 130, and the portion of the fluid flow path 133 defined between the inlet 132 and the sequestration portion 134.

Although not shown in FIG. 1, in some embodiments, the sequestration portion 134 can include any suitable arrangement, configuration, and/or feature, and/or can be formed of one or more materials configured to interact with a portion of the bodily fluid transferred into the sequestration portion 134. For example, in some embodiments, the housing 130 can include an absorbent and/or hydrophilic material disposed within the sequestration portion 134 configured to absorb, attract, wick, retain, expand, and/or otherwise interact with at least a portion of the bodily, fluid, which in turn, can sequester and/or retain at least an initial portion of the bodily fluid within the sequestration portion 134. Similarly, in some embodiments, the sequestration portion 134 and/or a portion thereof can have a geometry (e.g., a high surface area to volume ratio, a capillary configuration, etc.) and/or can be formed of a material or coating (e.g., a textured or pitted surface) configured to wick, attract, absorb, and/or retain bodily fluids.

In other embodiments, the sequestration portion 134 can include and/or can be formed of an expandable or collapsible material or can include or form a flexible bladder configured to transition between a first state (e.g., while an initial portion of the bodily fluid is being transferred into the sequestration portion 134) and a second state (e.g., after the initial portion of the bodily fluid is transferred into the sequestration portion 134) to encourage bodily fluid to flow into the sequestration portion 134 and/or to retain or sequester bodily fluid in the sequestration portion 134. In some embodiments, a force associated with and/or resulting from such a material expanding or collapsing can be operable to transition the housing 130 and/or the device 100 from a first state, position, configuration, etc. to a second state, position, configuration, etc. In some embodiments, the sequestration chamber 134 and/or any other suitable portion of the housing 130 can include one or more chemicals, compounds, and/or the like configured to chemically interact with bodily fluid transferred through a portion of the housing 130, which can be operable to transition the control device 100 and/or the housing 130 between the first state and the second state (e.g., via a force or any other suitable means).

In some embodiments, the housing 130 and/or the sequestration portion 134 can include and/or define a vent, port, opening, and/or the like in fluid communication with the sequestration portion 134 and configured to "vent" the sequestration portion 134. In some embodiments, the housing 130 can include a semi-permeable member or membrane disposed in or about the vent to selectively allow a flow of air or gas through the vent while limiting or substantially preventing a flow of fluid (e.g., bodily fluid such as blood) through the vent. In some embodiments, the venting of the sequestration portion 134 as an initial portion of the bodily fluid is transferred into the sequestration portion 134 can allow for an equalization of pressure in the sequestration portion 134 and/or between the sequestration portion 134 and, for example, the fluid source and/or a portion of the fluid flow path outside of the sequestration portion 134, or a pressure of an ambient environment into which the sequestration portion 134 is vented. In some embodiments, the equalization of pressure can be a factor in determining and/or defining how bodily fluid flows through the housing 130 and/or the amount or volume of bodily fluid to be transferred into the sequestration portion 134.

Expanding further, the venting of the sequestration portion 134 can allow a flow of air or gas to pass through the opening or semi-permeable member in response to being displaced by a flow of bodily fluid. For example, in some embodiments, the sequestration portion 134, the fluid flow path 133, and/or at least a portion of an inner volume of the housing 130 can contain a volume of air or gas prior to use. As bodily fluid flows through the inlet 132 of the housing 130 and enters the fluid flow path 133, the bodily fluid displaces at least a portion of the air or gas contained therein. Moreover, in some embodiments, the housing 130 can be in a first state or configuration in which the outlet(s) 136 is/are sealed or isolated prior to diverting and/or sequestering the initial portion of bodily fluid. Accordingly, the opening and/or semi-permeable member of the sequestration portion 134 allows for a venting of the sequestration portion 134 in response to the volume of air or gas being displaced by the bodily fluid and facilitates, urges, encourages, draws, and/or otherwise directs an initial flow of the bodily fluid into the sequestration portion 134, as described in further detail herein with respect to specific embodiments.

In some embodiments, a volume of air or gas disposed within the sequestration portion 134 before use can be vented prior to drawing a bodily fluid through the fluid flow path(s) 133 and into the sequestration portion 134. In other words, in some embodiments, the sequestration portion 134 can be pre-charged and/or evacuated (e.g., via an automated or manual process) prior to receiving the initial volume of bodily fluid. For example, in some instances, air or other gaseous contents disposed in the sequestration portion 134 prior to use can be expelled in response to an external force and/or compression of the sequestration portion 134 such that a release of the compression (after placing the inlet device 110 in communication with the bodily fluid) results in an increase in volume within the sequestration portion 134, which in turn, produces a negative pressure within the sequestration portion 134 operable in drawing an initial flow of the bodily fluid into the sequestration portion 134. As another example, the contents of the sequestration portion 134 can be removed prior to placing the inlet device 110 in contact with the source of the bodily fluid by suction through a vent or an opening using any suitable suction system. In some such embodiments, the contents of the sequestration portion 134 can be removed or vented via a negative pressure source such as, for example, a syringe, an evacuated container, a sample or culture bottle, a pump, and/or any other suitable negative pressure source in fluid communication with or configured to be placed in selective fluid communication with the sequestration portion 134. Moreover, in some embodiments, such a negative pressure source can be configured to receive a flow of bodily fluid via the outlet 136 after an initial volume of bodily fluid is transferred to and sequestered in the sequestration portion 134.

In some embodiments, the housing 130 and/or the sequestration portion 134 can enable and/or can allow for modulation of the negative pressure produced in and/or exerted through the sequestration portion 134. For example, the size, shape, material, and/or physical construction or the sequestration portion 134 can be configured to control a rate at which the volume of the sequestration portion 134 increases, which in turn, can control a magnitude of the negative pressure produced within the sequestration portion 134. In some embodiments, a desired combination of components, sizes, shapes, materials, and/or configurations can be chosen to draw bodily fluid (e.g. blood from the vasculature) from, for example, a physically compromised patient (e.g. ill patients, hypotensive patients, obese patients, pediatric patients, etc.) while a different combination of components, sizes, shapes, materials, and/or configurations can be chosen to draw bodily fluid from healthy or otherwise uncompromised patients.

In some embodiments, the fluid control device 100 can include an actuator 150. The actuator 150 can be included in the housing 130 (as shown in the schematic in FIG. 1) or the actuator 150 can be included in any other suitable portion of the device 100. The actuator 150 can be configured to transition the housing 130 from a first state (e.g., a state where an initial portion of the bodily fluid can be transferred into the sequestration portion 134) to a second state (e.g., after the initial portion of the bodily fluid is transferred into the sequestration portion 134). In some embodiments, the actuator 150 can be mechanically coupled to operate a switch—opening and/or closing portions of the fluid flow paths 133. For example, in some embodiments, the one or more mechanical actuators that can move or can be moved within the sequestration portion 134 to produce changes in volume and/or to produce a pressure differential between the sequestration portion 134 and, for example, the fluid source and/or a portion of the fluid flow path 133 outside of the sequestration portion 134.

In some embodiments, the actuator 150 can enable switching the state of the control device 100 by manipulating fluid flow through the various portions of the fluid flow paths 133 through any suitable manner. For example, in some embodiments, the movement of the actuator 150 can produce a pressure differential between the sequestration portion 134 and an ambient environment into which the sequestration portion 134 is vented. For example, a mechanical actuator can be in an initial state, prior to use of the control device 100, where a pressure differential between the sequestration portion 134 and the source of bodily fluid is based on a positive pressure associated with, for example, the vasculature of the patient (i.e., blood pressure). In such instances, the pressure differential can be relatively small. In some such instances, the mechanical actuator can be transitioned from the initial state to a subsequent state upon the start of the flow of the initial volume of bodily fluid such that the transitioning of the mechanical actuator can vent the air or gaseous contents within the sequestration portion 134 as well as produce a negative pressure differential between the sequestration portion 134 and the source of bodily, fluid, drawing the flow of bodily fluid into the sequestration portion 134. In some such embodiments, the transitioning of the mechanical actuator can also be configured to modify access to one or more openings to allow a flow of air or gas disposed within parts of the sequestration portion 134 through the openings (not shown in FIG. 1). For example, in some embodiments, the actuator 150 can be configured to physically block or occlude of one or more openings in one or more portions of the fluid flow path 133 that can be introduced or removed through the operation of one or more external control mechanisms (e.g. a switch, stop cock, lever, clamp, or press-button activated flow blocks, etc.), as described in further detail below.

In some embodiments, an amount of movement of the mechanical actuator and/or an equalization of pressure after the movement of the mechanical actuator can be a factor in determining and/or defining how bodily fluid flows through the control device 100 and/or the amount or volume of bodily fluid to be transferred into the sequestration portion 134, as disclosed in detail below with respect to specific embodiments.

In other embodiments, the method of activating the actuators can be via user intervention (e.g., an external force applied by a user). In some such embodiments, the sequestration chamber 114 can include structures or substances that are activated or deactivated to move or aid in the movement of the actuators from an initial state to a resulting state. The structures or substances can be activated by any suitable mechanism, for example, by contact with a small amount of bodily fluid (or any other fluid), by the passage of predetermined amount of time, by changes in pressure or temperature, and/or the like.

In some embodiments, the outlet(s) 136 of the housing 130 is in fluid communication with and/or is configured to be placed in fluid communication with the fluid flow path 133. The outlet 136 can be any suitable outlet, opening, port, lock, seal, coupler, adapter, etc. and is configured to be fluidically coupled to a fluid collection device 160 such as, for example, a fluid collection device 160, a syringe, an intermediary lumen-containing device, and/or any other suitable bodily fluid collection or transfer device. In some embodiments, the outlet 136 can be monolithically formed with the fluid collection device 160. In other embodiments, the outlet 136 can be at least temporarily coupled to the fluid collection device 160 via an adhesive, a resistance fit, a mechanical fastener, a threaded coupling, a piercing or puncturing arrangement, any number of mating recesses, and/or any other suitable coupling or combination thereof. Similarly stated, the outlet 136 can be physically (e.g., mechanically) and/or fluidically coupled to the fluid collection device 160 such that an interior volume defined by the fluid collection device 160 is in fluid communication with the outlet 136. In still other embodiments, the outlet 136 can be operably coupled to the fluid collection device 160 via an intervening structure (not shown in FIG. 1), such as a flexible sterile tubing.

As described above, in some embodiments, the arrangement of the at least one outlet 136 can be such that the outlet 136 is physically and/or fluidically sealed prior to coupling to the fluid collection device 160. In some embodiments, such a sealed arrangement can facilitate, direct, and/or otherwise result in an initial flow of bodily fluid into the sequestration portion 134 rather than the outlet 136. In some embodiments, the fluid collection device 160 can define and/or can be actuated to define a negative pressure that can be exerted through the outlet 136 to draw bodily fluid from the bodily fluid source, through the fluid control device 100, and into the fluid collection device 160 after and/or in response to the initial volume of bodily fluid being transferred to and sequestered in the sequestration portion 134. In some embodiments, the fluid collection device 160 can be placed in selective fluid communication with at least a portion of the sequestration portion 134 such that at least a portion of the negative pressure associated with the fluid collection device 160 is exerted on or through the sequestration portion 134 to transfer the initial volume of bodily fluid into the sequestration portion 134 without transferring a volume of bodily fluid into the fluid collection device 160 (e.g., through the use of a selectively permeable member such as an air permeable/fluid impermeable barrier or the like).

As described above, the fluid collection device 160 can be any suitable device for receiving and/or at least temporarily containing bodily fluid. In some embodiments, the fluid collection device 160 can be a fluid collection device for containing a bodily fluid, such as, for example, any of those described in detail in the '420 Patent incorporated by reference above. In other embodiments, the fluid collection device 160 can be substantially similar to or the same as known sample containers such as, for example, a Vacutainer® (manufactured by Becton, Dickinson and Company ("BD")), a BacT/ALERT® SN or BacT/ALERT® FA (manufactured by Biomerieux, and/or any suitable reservoir, vial, microvial, microliter vial, nanoliter vial, container, microcontainer, nanocontainer, syringe, dish, pump, and/or the like.

In some embodiments, the fluid collection device 160 can include and/or can define a negative pressure condition prior to use, which in turn, can facilitate withdrawal of bodily fluid from the patient, through the control device 100, and into the fluid collection device 160, via a vacuum or suction force. In embodiments in which the fluid collection device 160 is an evacuated container or the like, the user can couple the fluid collection device 160 to the outlet 136 after the initial portion of the bodily fluid is transferred into and/or sequestered by the sequestration portion 134, which in turn, can limit and/or substantially prevent an initial portion of the bodily fluid (potentially containing contaminants) from being transferred into the fluid collection device 160. In other embodiments, at least a portion of the negative pressure associated with the fluid collection device 160 can be used to generate a negative pressure differential between, for example, the sequestration portion 134 and the inlet 132 operable to draw bodily fluid into the sequestration portion 134 without drawing bodily fluid into the fluid collection device 160 prior to an initial volume of bodily fluid being sequestered in the sequestration portion 134.

Although the outlet 136 of the control device 100 and/or the housing 130 is described above as being fluidically coupled to and/or otherwise placed in fluid communication with the fluid collection device 160, in other embodiments, the control device 100 can be used in conjunction with any suitable bodily fluid collection device and/or system. For example, in some embodiments, the control device 100 described herein can be used in any suitable fluid transfer device such as those described in U.S. Patent Publication No. 2015/0342510 entitled, "Sterile Bodily-Fluid Collection Device and Methods," filed Jun. 2, 2015 (referred to herein as the "510 publication"), the disclosure of which is incorporated herein by reference in its entirety. More particularly, the control device 100 can be used in an "all-in-one" or pre-assembled device (e.g., such as those described in the '510 publication) to receive and sequester an initial volume of bodily fluid such that contaminants in subsequent volumes of bodily fluid are reduced and/or eliminated.

As described above, the device 100 can be used to procure a bodily fluid sample having reduced contamination from microbes such as, for example, dermally residing microbes and/or the like. For example, in some instances, a user such as a doctor, physician, nurse, phlebotomist, technician, etc. can manipulate the device 100 to establish fluid communication between the inlet device 110 and the bodily fluid source (e.g., a vein of a patient, cerebral spinal fluid (CSF) from the spinal cavity, urine collection, and/or the like). As a specific example, in some instances, the inlet device 110 can include a needle or the like that can be manipulated to puncture the skin of the patient and to insert at least a portion of the needle in the vein of the patient, thereby placing the inlet device 110 in fluid communication with the bodily fluid source (e.g., the vein, an IV catheter a PICC, etc.).

The housing 130 can be coupled to the inlet device 110 before or after the inlet device 110 is placed in fluid communication with the bodily fluid source. In other embodiments, the inlet 132 of the housing 130 includes, forms, and/or is monolithically formed with the inlet device 110. Thus, by coupling or forming the inlet 132 to or with the inlet device 110, establishing fluid communication between the inlet device 110 and the bodily fluid source places the housing 130 in fluid communication with the bodily fluid source. Thus, bodily fluid can flow from the bodily, fluid source (e.g., the vein of the patient), through the inlet device 110, and into the housing 130.

In some embodiments, the actuator 150 of the device 100 can be configured to place the control device 100 in a first state (e.g., a state where an initial portion of the bodily fluid can be transferred into the sequestration portion 134). Thus, as the inlet 132 of the housing 130 is in fluid communication with the bodily fluid source, the actuator 150 can place the control device 100 in a first state, forming a fluidic connection between the bodily fluid source and the sequestration portion 134 through one or more portions of the fluid flow paths 133. In other embodiments, the actuator 150 can be configured to maintain the control device 100 in a storage and/or pre-use configuration or state in which the inlet 132 of the housing 130 is sequestered and/or isolated from the sequestration portion 134 and the one or more outlets 136. In such embodiments, the actuator 150 can be manipulated to transition the control device 100 from the storage configuration and/or state to the first state, for example, after the inlet device 110 establishes fluid communication with the bodily fluid source.

As described above, the fluid flow path 133 of the housing 130 establishes fluid communication between the inlet 132 and the sequestration portion 134 and/or the outlet 136. In some embodiments, the arrangement of the housing 130 and/or the actuator 150 is such that when a volume of bodily fluid is transferred to and/or through the inlet 132, an initial portion of the volume of bodily fluid (also referred to herein as an "initial volume" or a "first volume") flows from the inlet 132, through at least a portion of the fluid flow path 133, and into the sequestration portion 134. That is to say, in some embodiments, the control device 100 can be placed in the first or initial state (e.g., via the actuator 150) such that the initial portion or volume of bodily fluid can flow in or through at least a portion the fluid flow path 133 and into the sequestration portion 134.

For example, in some embodiments, the actuator 150 can be in a first configuration, state, mode, and/or position when the control device 100 is in the initial state. The first configuration of the actuator 150 can be, for example, a configuration in which the actuator 150 allows fluid communication to be established between the inlet 132 and the sequestration portion 134 via at least a portion of the fluid flow path 133, and in Which the actuator 150 occludes, sequesters and/or isolates the inlet 132 from the outlet 136 or the fluid collection device 160. For example, the actuator 150, when in the first configuration, can define an opening, aperture, orifice, conduit, channel, flow path, or the like, to permit fluid flow from the inlet 132 toward the sequestration portion 134, and can block or occlude an opening, aperture, orifice, conduit, channel, flow path, or the like, to block fluid flow from the inlet 132 toward the outlet 136 or the fluid collection device 160. In some embodiments, the first configuration of the actuator 150 can be the resting or initial configuration of the actuator 150 (e.g., a pre-use configuration). That is, the actuator 150 can be in the first configuration (and the control device 100 can be in the first state) to allow fluid flow from the inlet device 110 toward the sequestration portion 134, without any user intervention. In other embodiments, the actuator 150 can be placed in and/or transitioned to the first configuration upon manipulation by a user.

In some embodiments, when the control device 100 is in the initial state, the sequestration portion 134 is vented and the outlet 136 is sequestered (e.g., via the actuator 150). As such, bodily fluid entering the fluid flow path 133 displaces a volume of air or gas otherwise disposed therein and the venting of the sequestration portion 134 allows the volume of air or gas to vent through the sequestration portion 134, which in turn, urges, draws, and/or otherwise diverts the initial portion of the bodily fluid into the sequestration portion 134 prior to the bodily fluid flowing to the outlet 136. In some embodiments, the venting of the sequestration portion 134 can be accomplished by any other suitable method. In some embodiments, for example, the actuator 150 can be in its initial configuration or the like prior to the inlet device 110 being placed in fluid communication with the source of bodily fluid. For example, the sequestration portion 134 can be compressed (e.g., by a user and/or pre-compressed or evacuated during manufacturing or the like) to expel the contents prior to placing the inlet device 110 in contact with the source of bodily fluid (e.g., the vasculature of a patient.) so that any air or gas disposed in the sequestration portion 134 is released to the ambient environment. In such embodiments, the actuator 150 can then be switched from the initial or venting configuration to the first position allowing bodily fluid flow from the inlet 132 toward the now emptied or evacuated sequestration portion 134. In some embodiments, the initial or venting configuration of the actuator 150 can be different from the first configuration. In other embodiments, the initial or venting configuration can be the same as the first configuration.

In some instances, transitioning the actuator 150 from the initial or venting configuration to the first configuration (e.g., in which the control device 100 is in the first state) after venting or evacuating sequestration portion 134, can aid in establishing a negative pressure differential operable to draw bodily fluid through the inlet device 110 and at least a portion of the fluid flow path 133 and into the sequestration portion 134. In some instances, expelling the contents of the sequestration portion 134 prior to establishing contact with the source of bodily fluid can remove potential air or gaseous bubbles, which may inadvertently be introduced into the source of bodily fluid and/or the bodily fluid sample. In other embodiments, the device 100 can be stored prior to use with a fluid or gas disposed in the sequestration portion 134 that is configured to maintain a sterile environment within the sequestration portion 134, In such embodiments, evacuating the sequestration portion 134 prior to establishing contact with the source of bodily, fluid can expel such fluid or gas. In addition, when the actuator 150 is in the venting configuration and/or in the first configuration, the actuator 150 can separate, occlude, isolate, and/or otherwise sequester the outlet 136 from the inlet 132 of the housing 130. The isolation of the outlet 136 from the source of bodily fluid can, for example, prevent a negative pressure within the fluid collection device 160 from drawing bodily fluid into the fluid collection device 160 prior to withdrawing and sequestering the initial volume of bodily fluid in the sequestration portion 134.

In some embodiments, negative pressure can be introduced in the sequestration portion 134 and the flow paths 133 connecting the sequestration portion 134 to the inlet 132 and/or the inlet device 110, including any intermediary portion of the actuator 150 in the first position, using any suitable user mediated or non-user mediated method. In other embodiments, the sequestration portion 134 and the flow paths 133 can be evacuated, vented, and/or placed under reduced or negative pressure during manufacturing or the like (also referred to herein as "pre-charged"). The negative pressure can in turn draw or urge fluid flow towards and into the sequestration portion 134. For example, in some embodiment, the sequestration portion 134, the connecting fluid flow paths 133, and/or the inlet device 110 can be positioned at a relatively lower altitude than the source of bodily fluid (e.g., vasculature of a patient) to use gravitational forces to aid in fluid flow. The vent or seal in communication with the sequestration portion 134 can be configured to allow unidirectional flow out of air or gas (but not liquid such as bodily fluid) out of the sequestration portion 134. In some embodiments, a negative pressure associated with the fluid collection device 160 (e.g., an evacuated container, syringe, etc.) can be used to draw bodily fluid into the sequestration portion 134 without drawing bodily fluid into the fluid collection device 160 until the initial portion or volume of bodily fluid is sequestered.

Although not shown in FIG. 1, in some embodiments, the control device 100 and/or the housing 130 can include a member, device, mechanism, feature, etc. configured to modulate a magnitude of the negative pressure to which the sequestration chamber 134 is exposed. For example, in some embodiments, a housing can include a valve, a membrane, a porous material, a restrictor, an orifice, and/or any other suitable member, device, and/or feature configured to modulate pressure. In some embodiments, modulating and/or controlling a magnitude of the pressure to which the sequestration chamber 134 is exposed can, in turn, modulate a magnitude of pressure exerted on the bodily fluid and/or within a vein of a patient. In some instances, such pressure modulation can reduce, for example, hemolysis of a blood sample and/or a likelihood of collapsing a vein (e.g., which is particularly important in fragile patients needing microbial and/or other diagnostic testing associated with use of the control device 100). In addition, the modulation of the negative pressure can, for example, at least partially control a rate at which the control device 100 transitions between a first configuration or state and a second configuration or state. In some embodiments, modulating the negative pressure can act like a timer. For example, a time between the introduction of the negative pressure differential and the transitioning of the control device 100 from the first state to the second state can be known, predetermined, calculated, and/or controlled. As such, in some instances, modulating the negative pressure can at least partially control an amount or volume of bodily fluid transferred into the sequestration chamber 134 (i.e., can control a volume of the initial amount of bodily fluid).

The initial portion and/or amount of bodily fluid can be any suitable volume of bodily, fluid, as described above. For example, in some instances, the control device 100 can remain in the first state until a predetermined and/or desired volume (e.g., the initial volume) of bodily fluid is transferred to the sequestration portion 134. In some embodiments, the initial volume can be associated with and/or at least partially based on a volume of the sequestration portion 134. In other embodiments, the initial volume can be associated with and/or at least partially based on an amount or volume of bodily fluid that can be absorbed by an absorbent material, an expandable material, a hydrophilic material, a wicking material, and/or other suitable material disposed in the sequestration portion 134. Similarly, the initial volume can be associated with and/or at least partially based on an amount or volume of bodily fluid that is sufficient to fully wet or saturate a semi-permeable member or membrane otherwise configured to vent the sequestration portion 134 (e.g., the sequestration portion 134 is transitioned from a "venting" state to a "sealed" state or the like). In still other embodiments, the control device 100 can be configured to transfer a volume of bodily fluid (e.g., the initial volume) into the sequestration portion 134 until a pressure differential between the sequestration portion 134 and the fluid flow path 133 and/or the bodily fluid source is brought into substantial equilibrium and/or is otherwise reduced below a desired threshold. In some embodiments, the pressure differential can be established automatically or via direct or indirect intervention (e.g., by the user).

In some embodiments, the initial volume can be measured during procurement by using any suitable method such as, for example, a graduated sequestration portion 134 or a graduated tubing that can be associated with or part of one or more portions of the fluid flow path 133 connecting the inlet 132 to the sequestration portion 134. Once the collected initial volume of fluid reaches a predetermined value the actuator 150 can be transitioned from the first configuration toward a second configuration, thereby stopping any further fluid flow of bodily fluid into the sequestration portion 134 and transitioning the control device 100 from the first state toward a second state. After the initial volume of bodily fluid is transferred and/or diverted into the sequestration portion 134, the initial volume is sequestered, segregated, retained, contained, isolated, etc. in the sequestration portion 134 by transitioning the actuator 150 to the second configuration. As described in further detail herein, in some instances, contaminants such as, for example, dermally residing microbes or the like dislodged during the venipuncture event, can be entrained and/or included in the initial volume of the bodily fluid and thus, are sequestered in the sequestration portion 134 when the initial volume is sequestered therein.

With the initial volume transferred and/or diverted into the sequestration portion 134, the device 100 can transition—or can be transitioned—to the second state in which a subsequent volume(s) of bodily fluid can flow through at least a portion the fluid flow path 133 from the inlet 132 to the outlet 136. In some embodiments, the control device 100 can passively and/or automatically transition (e.g., without user intervention) from the first state to the second state once the initial volume of bodily fluid is sequestered in the sequestration portion 134. For example, in some embodiments, filling the sequestration portion 134 to capacity and/or fully saturating, wetting, and/or impregnating an absorbent or similar material disposed in the sequestration portion 134 can be such that further transfer of bodily fluid into the sequestration portion 134 is limited and/or substantially prevented.

In some embodiments, as described above, the control device 100 can be transitioned from the first state to the second state by the switching or actuating the actuator 150. The actuator 150 can be configured to switch from the first configuration (e.g., position, state, operating mode, arrangement, etc.), in which the actuator 150 allows fluid flow towards the sequestration portion 134 while blocking fluid flow toward the one or more outlets 136 or toward the fluid collection device 160, to a second configuration, in which the sequestration portion 134 is sequestered and/or blocked and fluid is allowed to flow toward the outlet 136 or the fluid collection device 160.

In some embodiments, the control device 100 can be transitioned from the first state to the second state through various passive or active mechanisms or combinations of passive and active mechanisms. Similarly, the actuator 150 can assume various configurations, states, and/or positions (e.g., a storage state, a venting state, the first state, the second state, etc.) either passively, based upon one or more other changing parameters during procurement of bodily fluid from a user, or through active user intervention, or through a combination of passive and active mechanisms. In some embodiments, for example, the actuator 150 can assume the various states based on passive mechanisms that do not require or involve user intervention. For example, the actuator 150 can transition between states in response to a passage of time, a change in volume, a change in physical characteristics like saturation of hydrophilic material in the sequestration portion 134, a change in the degree of negative pressure exerted to draw or urge fluid flow towards or into the sequestration portion 134, and/or the like. The actuator 150 can also take advantage of other changing parameters like a change in gravitational forces exerted to draw fluid into an appropriately placed sequestration portion 134.

In some embodiments, the actuator 150 can be transitioned actively through user intervention from the first state to the second state. In other words, the actuator 150 can be manually transitioned by a user directly controlling the direction of flow of the bodily fluid with the actuator 150, thereby also transitioning the control device 100 from the first state to the second state. As described above, the actuator 150 can be switched from the first state to the second state based on any suitable criterion (e.g., the volume of bodily fluid collected in the sequestration portion 134, the pressure differential urging flow of fluid into the sequestration portion 134, etc.) or based on any other suitable indication or user discretion. As such, when the criterion is satisfied, a user can manipulate the actuator 150 (e.g., a switch, valve, port, stopcock, etc.) to transition the actuator 150 from the first state to the second state.

The fluid collection device 160 can be at least fluidically coupled to the outlet 136 before or after the housing 130 is placed in the second state. Similarly, in some embodiments, the fluid collection device 160 can be at least fluidically coupled to the outlet 136 before or after the actuator 150 is transitioned from the first configuration or state to the second configuration or state. The arrangement of the outlet 136 can be such that the outlet 136 remains sealed until the initial volume of bodily fluid is sequestered in the sequestration portion 134 regardless of whether the fluid collection device is coupled to the outlet 136. Accordingly, with the fluid collection device 160 fluidically coupled to the outlet 136 and with the housing 130 being in the second state (e.g., the initial volume of bodily fluid is sequestered in or by the sequestration portion 134 and the actuator 150 is in the second configuration or state to establish fluid communication between the inlet 132 and the outlet 136) any subsequent volume(s) of the bodily fluid can flow from the inlet 132, through the fluid flow path 133, the actuator 150, and the outlet 136, and into the fluid collection device 160. Thus, as described above, sequestering the initial volume of bodily fluid in the sequestration portion 134 prior to collecting or procuring one or more sample volumes of bodily fluid reduces and/or substantially eliminates and amount of contaminants in the one or more sample volumes. Moreover, in some embodiments, the arrangement of the control device 100 and/or the actuator 150 can be such that control device 100 and/or the actuator 150 cannot transition to the second state prior to collecting and sequestering the initial volume in the sequestration portion 134.

Figure 2:
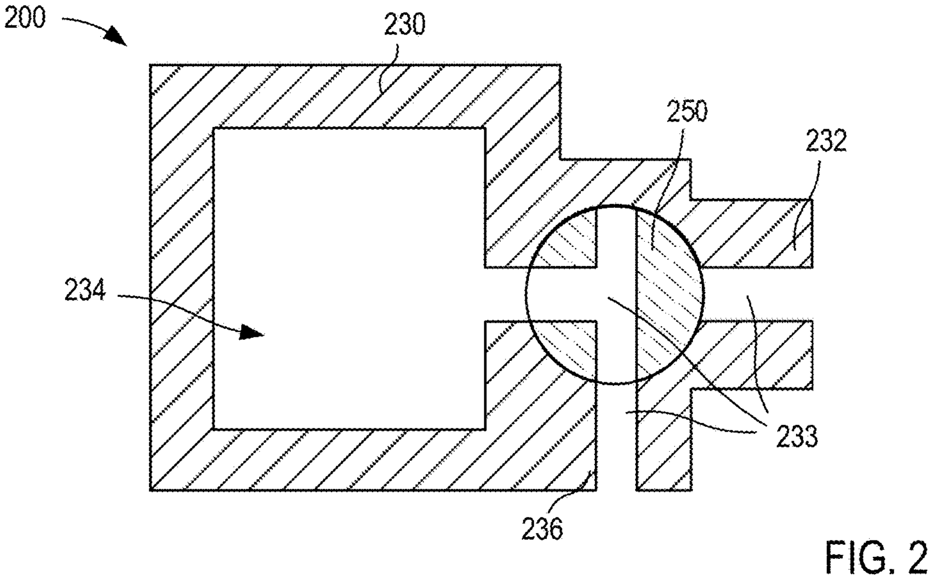
FIGS. 2-4 are cross-sectional schematic illustrations of a fluid control device in a first state or configuration, a second state or configuration, and a third state or configuration, respectively, according to an embodiment.
Figure 3:
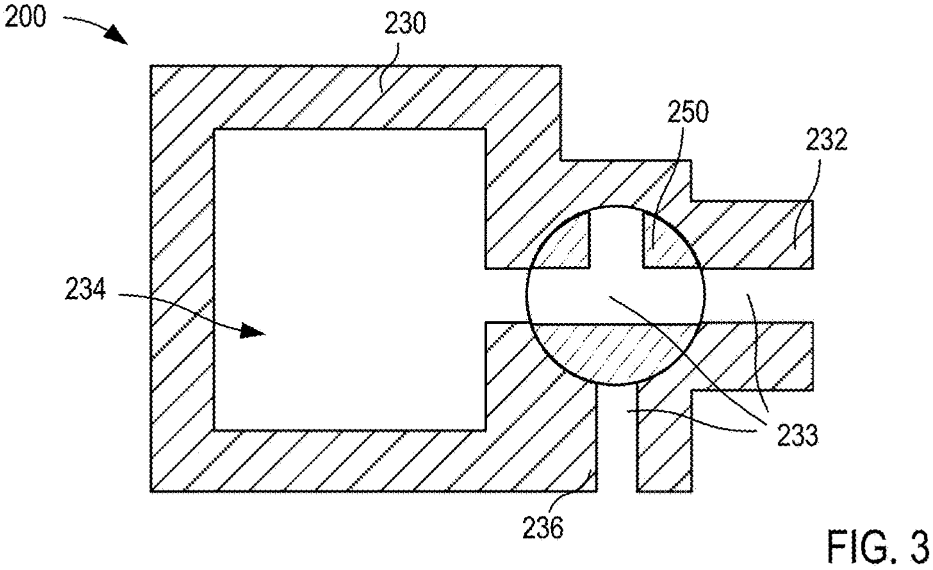
Figure 4:
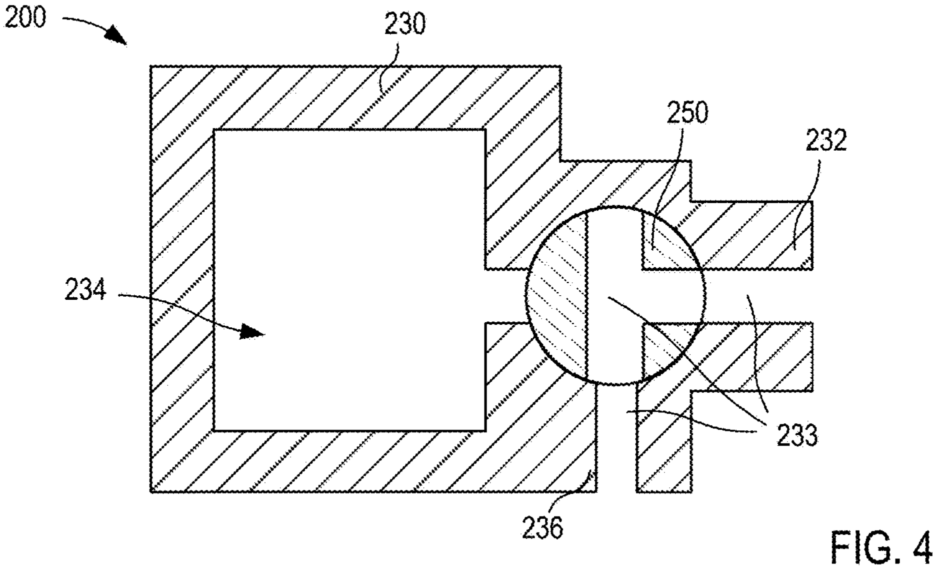

FIGS. 2-4 illustrate (in cross-sectional views) at least a portion of a fluid control device 200 according to an embodiment. As described above with reference to the control device 100, the fluid control device 200 (also referred to herein as "control device" or "device") is configured to withdraw and sequester a first portion or amount (e.g., an initial amount) of bodily fluid from a patient and subsequently withdraw a second portion or amount (e.g., a subsequent amount) of bodily fluid for use, for example, in bodily fluid sampling and/or testing. By sequestering the first portion or amount of bodily fluid, contaminants or the like such as, for example, dermally residing microbes dislodged during venipuncture are similarly sequestered, leaving the second portion or amount of bodily fluid substantially free of contaminants. In some embodiments, portions and/or aspects of the control device 200 are substantially similar in form and/or function to the corresponding portions and/or aspects of the control device 100 described above with reference to FIG. 1. Accordingly, such similar portions and/or aspects are not described in further detail herein.

As shown in FIGS. 2-4 the control device 200 includes a housing 230, similar in structure and/or function to the housing 130 of the fluid control device 100 described above, and an actuator 250 similar in structure and/or function to the actuator 150 described above with reference to the fluid control device 100. The illustrations in FIGS. 2-4 show the actuator 250 assuming various configurations and/or positions (e.g. a venting position, a first position, and a second position), as described in further detail herein.

The housing 230 can be any suitable device or set of devices configured to (1) receive a flow of bodily fluid, (2) store and sequester a first volume or initial volume of the bodily fluid, and (3) direct or divert a subsequent flow of the bodily fluid to a fluid collection device, as described in further detail herein. The housing 230 can be any suitable shape, size, and/or configuration. For example, in some embodiments, the housing 230 can be formed of a relatively rigid material such as a plastic or the like and can be configured to retain its shape and/or form when exposed to changes in pressure and/or an inlet or an outlet flow of fluid. In other embodiments, the housing 230 can be made from a pliable material that can be amenable to compression and/or other similar forces used to expel the contents of the sequestration portion 234 prior to use, as described above with respect to the housing 130 of the fluid control device 100.

As shown in FIGS. 2-4, the housing 230 includes an inlet 232 and an outlet 236. The inlet 232 is in fluid communication with and/or is configured to be placed in fluid communication with an inlet device (not shown). In general, the inlet device can be any suitable device or set of devices configured to establish fluid communication between the housing 230 and a bodily fluid source such as, for example, the vasculature of a patient, as described above with reference to the control device 100. The outlet 236 is in fluid communication with and/or is configured to be placed in fluid communication with a fluid collection device (not shown in FIGS. 2-4) such as a fluid collection device, syringe, culture bottle, and/or the like. The fluid collection device can be similar to any of the fluid collection devices described above with reference to the control device 100.

The housing 230 includes and/or defines one or more fluid flow paths 233 and a sequestration and/or diversion portion 234. The fluid flow path(s) 233 can be any suitable arrangement and are configured to selectively establish fluid communication between the inlet 232 and the sequestration and/or diversion portion 234 and/or between the inlet 232 and the outlet 236. The sequestration and/or diversion portion 234 (also referred to herein as "sequestration portion") can be any suitable shape, size, and/or configuration and is configured to receive an initial volume of bodily fluid, which can contain contaminants or other undesirable material, and to sequester the initial volume of bodily fluid and the contaminants and/or other undesirable material in the sequestration portion 234 after receiving the initial volume, as described in further detail herein.

As described above, in some embodiments, the actuator 250 can be associated with, included in, and/or coupled to the housing 230, as shown in FIGS. 2-4. The actuator 250 can be any suitable member, device, mechanism, etc. configured to transition between at least two different operating states to selectively control fluid flow through the housing 230. For example, as described above with respect to the actuator 150 included in the device 100, the actuator 250 can be a switch, a valve, a port, a membrane, a movable channel, a clamp, and/or the like configured to manipulate fluid flow (either directly or indirectly) through the housing 230.

The actuator 250 can be formed monolithically or as integrated part of the housing 230, or can be formed separately and at least operably coupled to the housing 230. In the embodiment shown in FIGS. 2-4, the actuator 250 can be a three-way valve, port, stopcock, and/or the like, whose configuration can be changed to form pathways, conduits, and/or channels to allow fluid flow in selected directions. The actuator 250 can include lumens, channels, openings, flow paths, and/or the like that that can be aligned with or placed adjoining various portions of the fluid flow path 233 to control fluid flow through the housing 230. The actuator 250 is configured to be placed in different configurations that permit fluid flow through selected portions of the actuator 250 and the fluid flow path 233, while blocking fluid flow through other portions of the fluid flow path 233.

The configuration of the actuator 250 can be switched, modified, and/or manipulated either by passive methods, active intervention of a user, or a combination of active and passive methods, as described above with reference to the actuator 150. For example, in some embodiments, the actuator 250 can be a rotary valve driven by a spring or a damper mechanism such that the actuator 250 can be switched between several positions, with each switch in position occurring over a predetermined time or when a specific criterion is met such as a predetermined pressure differential, and/or the like. For example, the actuator 250 can be a push button, toggle, switch, lever, dial, etc., which when engaged by a user can transition the actuator 250 from a first state or position to a second state or position. As described in further detail herein, in some embodiments, the actuator 250 can be configured to establish fluid communication between the inlet 232 and the sequestration portion 234 when in a first state, configuration, and/or position and can be configured to establish fluid communication between the inlet 232 and the outlet 236 when in a second state, configuration, and/or position.

In some embodiments, the actuator 250 can be configured in any other suitable form. For example, instead of a three-way valve (e.g., a rotary valve, port, and/or the like), the actuator 250 can be a two-way valve or any other suitable path selector, in a Y-configuration or a configuration, allowing selection between an open flow path connecting the inlet 232 with the sequestration portion 234 and an open flow path connecting the inlet 232 with the outlet 234.

In some embodiments, the actuator 250 can be an opening/closing mechanism of pre-exiting channels, pathways, and/or conduits, thus not forming new channels or conduits but allowing or blocking access to one or more pre-existing channels or conduits. For example, the actuator 250 can be configured to open (or block) at least a portion of the fluid flow path 233 connecting the sequestration portion 234 to the inlet 232, while blocking (or opening) at least a portion of the fluid flow path 233 connecting the outlet 236 to the inlet 23. In some embodiments, the actuator 250 can be configured as a rotary valve (as shown in FIGS. 2-4), a linear valve (e.g., a plunger) with a series of seals, and/or any other suitable valve.

The operation of the actuator 250 in opening and blocking of one or more flow paths can be configured to be either sequential or simultaneous. Similarly, the actuator 250 can be designed such that only a specific number of flow paths are open at any particular configuration. For example, the actuator 250 can be designed such that only one of the sequestration portion 234 or the outlet 236 can be fluidically connected to the inlet 232 at any given configuration. In some other embodiments, the actuator 250 can allow fluid communication between multiple portions of the housing 230. For example, in some embodiments, the actuator 250 can be designed such that fluid communication can be established between the inlet 232 and the sequestration portion 234 as well as the inlet 232 and the outlet 236 substantially concurrently. In some such embodiments, the actuator 250 can allow selection of fluid flow paths through one or more control mechanisms other than blocking or occluding (e.g. by manipulating pressure differential or some other mechanism that urges flow of fluid in a particular direction). In some embodiments, the actuator 250 can operate by physically permitting or blocking access to specific fluid flow paths such that the opening of a first fluid flow path (e.g., the fluid flow path connecting the inlet 232 with the sequestration portion 234) automatically results in the blocking of another fluid flow path (e.g., the fluid flow path connecting the inlet 232 with the outlet 236) and vice versa. In some embodiments, however, the permitting and/or blocking of specific fluid flow paths may be flexible allowing user discretion or control in the selection of one or more fluid flow paths.

In some embodiments, the actuator 250 can be placed in a storage and/or venting configuration, as described above with respect to the actuator 150 of the control device 100. For example, FIG. 2 illustrates the actuator 250 in the storage and/or venting configuration prior to use for procurement of bodily fluids. As described above, in the storage and/or venting configuration, the actuator 250 can fluidically isolate the inlet 232 from the sequestration portion 234 and the outlet 236. Although not shown in FIG. 2, in some embodiments, the outlet 236 can be substantially sealed prior to use. In some embodiments, a user may transition the outlet 236 to an open configuration and/or the like, which can allow removal, outflow, or expulsion of air or other gaseous contents disposed in the sequestration portion 234 (e.g., via the outlet 236) prior to placing the sequestration portion 234 in fluid communication with the inlet 232. For example, the venting of the contents of the sequestration portion 234 can evacuate the volume within the sequestration portion 234, thereby allowing bodily fluid to be drawn into the volume. In some embodiments, the venting can result in a negative pressure within the sequestration portion 234 that can be operable to draw or urge flow of the bodily fluid from the source of bodily fluid (e.g., the vasculature of a patient) into the sequestration portion 234 when the actuator 250 places the sequestration portion 234 in fluid communication with the inlet 232. In some embodiments, the venting, charging, and/or evacuation of the sequestration portion 234 can be in response to a fluid collection device being coupled to the outlet 236. For example, in some such embodiments, the fluid collection device can define a negative pressure or the like that can draw air or gas out of the sequestration portion 234, through the actuator 250 (while in the venting configuration), and through the outlet 236.

While FIG. 2 shows that the sequestration portion 234 can be vented via the outlet 236, in other embodiments, the housing 230 can include and/or can define any suitable opening(s), outlet(s), vent(s), port(s), etc. (not shown in FIGS. 2-4) in communication with the sequestration portion 234 and configured to allow for the venting of the contents disposed in the sequestration portion 234 prior to use of the device 200. In some embodiments, the access to these vents or the like can be controlled by the actuator 250 and/or any other suitable device. In other embodiments, the sequestration portion 234 is not vented prior to using the control device 200. In such embodiments, the actuator 250 can be stored in the storage configuration (as shown in FIG. 2) and/or can be stored in a configuration in which the inlet 232 is in fluid communication with the sequestration portion 234.

After venting the sequestration portion 234 and/or when otherwise ready to use the control device 200, the actuator 250 can be placed in a first configuration or position to establish fluid communication between the inlet 232 and the sequestration portion 234, as shown in FIG. 3. For example, in some embodiments, the actuator 250 can be a rotary valve or the like that can be switched from a storage and/or venting configuration (FIG. 2) to the first configuration (FIG. 3) by turning and/or rotating the actuator 250 (e.g., by rotating the actuator 250 by 90° in the clockwise direction). The clockwise turn or a similar switch in the position of the actuator 250 can be implemented by any suitable mechanism. For example, a rotary valve actuator 250 can be turned over a predetermined time period driven by a spring-loaded mechanism (e.g., a torsion spring that may provide a steady torque for turning the actuator 250). In some embodiments, a damper fluid can be used to control the rate of rotation of the actuator 250. In other embodiments, the actuator 250 can be switched between configurations and/or positions using a push-button mechanism, a lever, a switch, a slider, a toggle, a pressure dependent release mechanism, an external force-dependent (e.g. gravitational force dependent) mechanism, and/or any other suitable switching means. Similarly, any suitable mechanism can be used to control the rate of switching of the actuator 250 from one position to the next.

Once an initial volume of bodily fluid is transferred into the sequestration portion 234, the actuator 250 can be switched from the first configuration and/or position (FIG. 3) to a second configuration and/or position (FIG. 4). When in the second configuration and/or position, the actuator 250 is configured to establish fluid communication between the inlet 232 and the outlet 236, as shown in FIG. 4. In addition, the actuator 250 can be configured to sequester the sequestration portion 234 such that the sequestration portion 234 is not in fluid communication with the inlet 232 and not in fluid communication with the outlet 236. As such, an initial volume of bodily fluid within the sequestration portion 234 is sequestered, as described above with reference to the control device 100. Moreover, in some instances, the initial volume of bodily fluid can include contaminants and/or undesirable material that is likewise sequestered in the sequestration portion 234. Thus, with the actuator 250 in the second configuration and/or position, subsequent volumes of bodily fluid withdrawn from the patient can be substantially free from contaminants and can be transferred into one or more fluid collection devices (e.g., fluid collection devices or the like).

As described above, the actuator 250 can be switched between the first and second configuration and/or position using a mechanically activated mechanism (e.g. button-press, turn-control activated, lever activated, clamp activated, or a switch activated) or any other suitable mechanisms (e.g. pressure dependent, volume dependent, and/or time dependent, etc.). For example, in some embodiments, the actuator 250 can be switched in response to a force exerted by a user. In such embodiments, the user can visually inspect the housing 230 to determine whether the initial volume of bodily fluid is transferred into the sequestration portion 234. If the user confirms that the initial volume of bodily fluid is in the sequestration portion 234, the user can then exert a force on the actuator 250 to transition the actuator 250 from the first configuration and/or position to the second configuration and/or position.

In other embodiments, the actuator 250 can be configured to transition from the first configuration and/or position to the second configuration and/or position in response to one or more criterion/criteria being satisfied. For example, in some embodiments, the actuator 250 can be configured to transition from the first configuration and/or position to the second configuration and/or position in response to pressure equalization between the sequestration portion 234 and the inlet 232. In other embodiments, the actuator 250 can be configured to transition from the first configuration to the second configuration in response to a desired volume being transferred into the sequestration portion 234. In still other embodiments, the actuator 250 can be configured to transition from the first configuration to the second configuration after a predetermined time has passed. For example, in some embodiments, if a volumetric flow rate of the bodily fluid is known or can be determined, then a time it would take for a desired volume of bodily fluid to flow into the sequestration portion 234 can likewise be determined. Thus, as described above, the actuator 250 can be transitioned between one or more configurations and/or positions automatically and/or in response to a direct or indirect user input.

Figure 6:
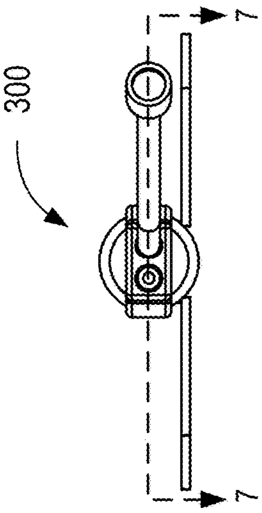
FIGS. 5 and 6 are a perspective view and a rear view, respectively, of a fluid control device according to an embodiment.
Figure 7:
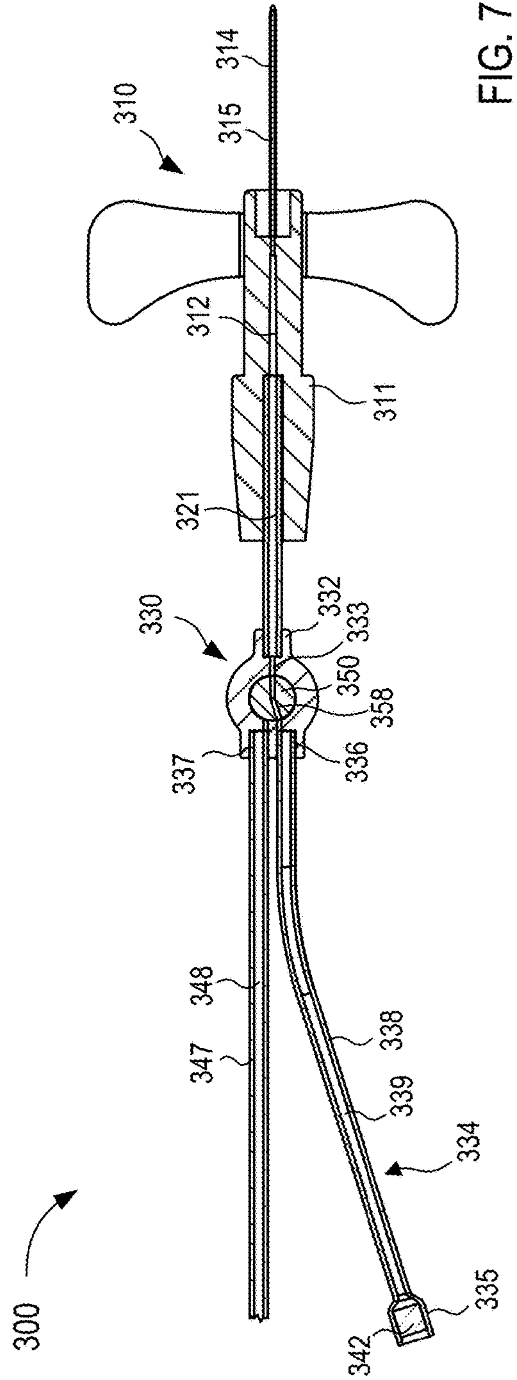
FIG. 7 is a cross-sectional view of the fluid control device illustrated in FIG. 6, taken along the line 7-7.
Figure 5:
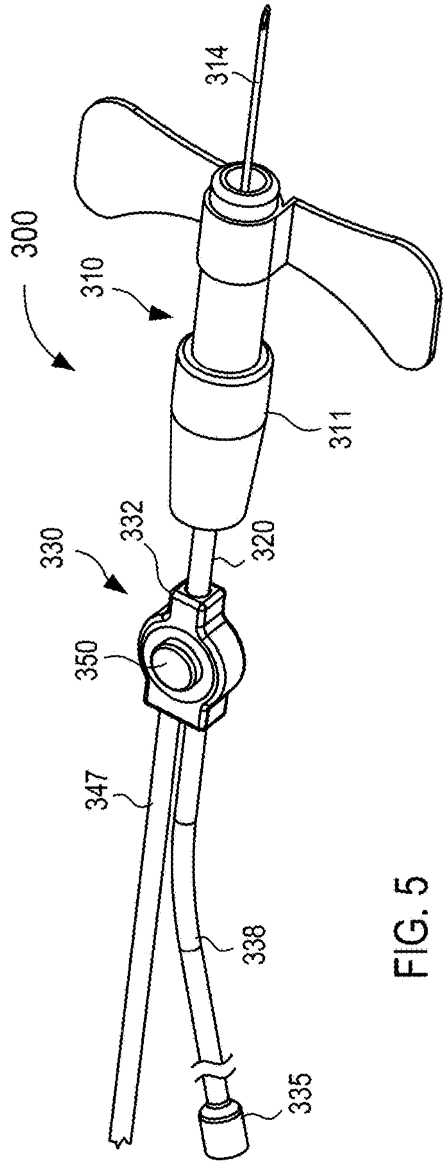

FIGS. 5-7 illustrate various views of a fluid control device 300 according to an embodiment. As described above with reference to the control devices 100 and 200, the fluid control device 300 (also referred to herein as "control device" or "device") is configured to withdraw and sequester a first portion or amount (e.g., an initial amount) of bodily fluid from a patient such that any subsequently withdrawn amount, portion, and/or volume of bodily fluid is substantially free of contaminants. In some embodiments, portions and/or aspects of the control device 300 are substantially similar in form and/or function to the corresponding portions and/or aspects of the control devices 100 and/or 200 described above with reference to FIG. 1 and FIGS. 2-4, respectively. Accordingly, such similar portions and/or aspects are not described in further detail herein.

As shown in FIG. 5, the control device 300 includes an inlet device 310, a housing 330 in fluid communication with and/or configured to be placed in fluid communication with the inlet device 310, and an actuator 350. The inlet device 310 can be any suitable device(s) such as, for example, an IV catheter, a sharpened catheter or sharpened needle, and/or any other suitable lumen-containing device. For example, in the embodiment shown in FIGS. 5-7, the inlet device 310 is a buttery-fly needle or other suitable access device having a body 311, a needle 314, and a flexible tubing 320. In general, the inlet device 310 can be any suitable device or set of devices configured to establish fluid communication between the housing 330 and a bodily fluid source such as, for example, the vasculature of a patient.

As shown in FIG. 7, the body 311 defines a lumen 312 extending through the body 311, the needle 314 defines a lumen 315 extending through the needle 314, and the flexible tubing 320 defines a lumen 321 extending through the flexible tubing 320. The needle 314 is coupled to, for example, a distal end portion of the body 311 such that the lumen 315 of the needle 314 is in fluid communication with the lumen 312 of the body 311, Likewise, the flexible tubing 320 is coupled to, for example, a proximal end portion of the body 311 such that the lumen 321 of the flexible tubing 320 is in fluid communication with the lumen 312 of the body 311. Thus, the lumen 315 of the needle 314, the lumen 312 of the body 311, and the lumen 321 of the flexible tubing 320 collectively define a fluid flow path extending through the inlet device 310. Moreover, the inlet device 310 can be similar to and/or substantially the same as the inlet device 110 described in detail above with reference to FIG. 1. Thus, the inlet device 310 is not described in further detail herein.

The housing 330 can be any suitable device or set of devices configured to (1) receive a flow of bodily fluid, (2) store and sequester a first volume or initial volume of the bodily fluid, and (3) direct or divert a subsequent flow of the bodily fluid to a fluid collection device, as described in further detail herein. In the embodiment shown in FIGS. 5-7, the housing 330 includes an inlet 332, a first outlet 336, and a second outlet 337, and defines a fluid flow path 333 and a sequestration portion 334. The housing 330 can be any suitable shape, size, and/or configuration. For example, in the embodiment shown in FIGS. 5-7, the housing 330 forms a Y-connector and/or the like. In some embodiments, the housing 330 can be formed of a relatively rigid material such as a plastic or the like and can be configured to retain its shape and/or form when exposed to changes in pressure and/or inlet and outlet flows of fluid.

As shown in FIG. 7, the housing 330 includes and/or receives a portion of the actuator 350 that can be configured to switch between a first configuration in which the actuator 350 establishes fluid communication between the inlet 332 and the first outlet 336, and a second configuration in which the actuator 350 establishes fluid communication between the inlet 332 and the second outlet 337, as described in further detail below. The inlet 332 of the housing 330 is coupled to the flexible tubing 320 (e.g., the flexible tubing 320 is a flexible inlet tubing for the housing 330), which defines a lumen configured to place the inlet 332 in fluid communication with the inlet device 310. The first outlet 336 is coupled to a first flexible outlet tubing 338 (also referred to herein as "first outlet tubing"), which defines a lumen 339 configured to receive a first or initial volume of bodily fluid flowing through the housing 330. The first outlet tubing 338 is also coupled to a vent 335 having a vent material 342 that can selectively vent the lumen 339 of the first outlet tubing 338. As such, at least a portion of the lumen 339 can form, for example, a sequestration portion 334 (also referred to herein as "sequestration portion") and/or the like, as described in further detail herein. The second outlet 337 is in fluid communication with a second flexible outlet tubing 347 (also referred to herein as "second outlet tubing"), which defines a lumen 348 configured to place the second outlet tubing 347 in fluid communication with one or more fluid collection devices (not shown).

In some embodiments, one or more portions of the fluid flow path(s) 333 can include at least one feature, characteristic, dimension, etc. that can modulate, modify, increase, decrease, and/or otherwise at least partially control pressures exerted through the fluid flow path 333. For example, in some embodiments, a portion of the fluid flow path 333 associated with and/or defined by the first outlet 336 can be offset and/or misaligned from a portion of the fluid flow path 333 associated with and/or defined by the inlet 332, which in turn, forms and/or defines a reduced diameter and/or other suitable restriction therebetween. Likewise, a portion of the fluid flow path 333 associated with and/or defined by the second outlet 337 can be offset and/or misaligned from the portion of the fluid flow path 333 associated with and/or defined by the inlet 332, which in turn, forms and/or defines a reduced diameter and/or other suitable restriction therebetween. As such, the restrictions can be configured to reduce, modify, and/or limit pressures exerted through the fluid flow path(s) 333. In other instances, portions of the fluid flow path 333 can have increased diameters and/or any other suitable feature configured to increase pressure differentials (e.g., either positive pressure differentials or negative pressure differentials).

The actuator 350 is included in and/or is coupled to the housing 330. The actuator 350 can be any suitable member, device, mechanism, and/or the like configured to selectively allow fluid flow from the inlet 332 to the first outlet 336 or from the inlet 332 to the second outlet 337. For example, in some embodiments, the actuator 350 is configured to transition between at least a first configuration, state, position, etc. and a second configuration, state, position, etc. to selectively control a flow of fluid through the housing 330. As previously described with respect to actuators 150, and/or 250 associated with devices 100 and/or 200, respectively, the actuator 350 can be a switch, a valve, a port, and/or the like, that can directly manipulate and/or establish one or more fluid flow paths, or that can indirectly manipulate and/or establish one or more fluid flow paths. For example, in some embodiments, the actuator 350 is a push-button activated switch or valve that defines a lumen 358 such that when the actuator 350 is in the first configuration, state, position, etc. (referred to for simplicity as a "first state"), the lumen 358 places the inlet 332 in fluid communication with the first outlet 336 and when the actuator 350 is in the second configuration, state, position, etc. (referred to for simplicity as a "second state"), the lumen 358 places the inlet 332 in fluid communication with the second outlet 337. The actuator 350 can be configured to be switched from one position to another either through user intervention or through the action of any, suitable passive force. For example, the actuator 350 can be switched by a manual or mechanical action (e.g. engaging and/or exerting a force on a button, a stopcock, a switch, a toggle, a slider, etc.), by one or more internal or external forces and/or changes in the magnitude of such forces (e.g., a change in magnitude of a negative pressure differential and/or the like), by the passage of a predetermined time, or through any suitable combination of active and/or passive mechanisms.

As described above, the state of the control device 300 can be at least partially based on the state of the actuator 350. For example, when the actuator 350 is in the first state, the control device 300 is likewise in the first state such that the inlet 332 is in fluid communication with the first outlet 336, and when the actuator 350 is in the second state, the control device 300 is likewise in the second state such that the inlet 332 is in fluid communication with the second outlet 337. As described in detail above with reference to the devices 100, and/or 200, the device 300 shown in FIGS. 5-7 can be used to divert a first or initial volume of bodily fluid such that subsequently procured bodily fluid samples have reduced contamination from microbes such as, for example, dermally residing microbes and/or the like. For example, in some instances, a user such as a doctor, physician, nurse, phlebotomist, technician, etc. can manipulate the device 300 by inserting at least a portion of the needle 314 into a patient's vein (e.g., a venipuncture event) and/or can otherwise establish fluid communication between the needle 314 and the patient. Once in fluid communication with the patient, bodily fluid can flow from the bodily fluid source (e.g., the vein of the patient), through the inlet device 310, and into the housing 330.

In some embodiments, the actuator 350 can be disposed in a storage configuration or the like prior to the inlet device 310 being placed in fluid communication with the patient. In such embodiments, the storage configuration can be such that the lumen 358 defined by the actuator 350 is isolated and/or otherwise not in fluid communication with the fluid flow path 333 or inlet 332 of the housing 330. Once the inlet device 310 is inserted into the patient, however, a user can engage the actuator 350 to transition the actuator 350 from the storage configuration or state to the first state (shown in FIG. 7). In other embodiments, the actuator 350 can be in the first state as the inlet device 310 is being inserted into the patient.

As described above, the first outlet tubing 338 is coupled to the vent 335 which can be configured to vent the lumen 339 of the first outlet tubing 338 (e.g., a sequestration portion 334) when the housing 330 is in the first or initial state. In this manner, a pressure differential (e.g., a negative pressure differential) between the lumen 339 of the first outlet tubing 338 and, for example, the lumen 315 of the needle 314 can encourage, draw, and/or urge bodily fluid to flow through the fluid flow path 333, through the lumen 358 defined by the actuator 350, and through the first outlet 336 in response to the negative pressure differential (e.g., based at least in part on the venting of the first outlet tubing 338). That is to say, when the control device 300 and the actuator 350 are in the first or initial states, a flow of bodily fluid is diverted or directed from the inlet 332 to the first outlet 336 and into the sequestration portion 334 (defined or formed by the first outlet tubing 338).

As such, a first amount or initial amount of bodily fluid can be transferred into the lumen 339 of the first outlet tubing 338. In some instances, the first outlet tubing 338 can be bent, flexed, and/or positioned such that flow of the bodily fluid into the lumen 339 of the first outlet tubing 338 is assisted and/or enhanced by gravitational forces. For example, in some instances, an end portion of the first flexible outlet tubing 338 (e.g., the end portion coupled to and/or including the vent 335) can be placed in a position below the housing 330 (e.g., at a lower elevation), thereby facilitating the flow of bodily fluid toward the vent 335. Although not shown in FIGS. 5-7, in some embodiments, the first outlet tubing 338 and/or the vent 335 can be in selective fluid communication with the second outlet tubing 347. For example, in some embodiments, the vent material 342 can be a gas permeable and fluid impermeable barrier or the like. In such embodiments, the second outlet tubing 347 can be fluidically coupled to a fluid collection device and/or any other suitable negative pressure source that can, for example, exert a negative pressure through the vent material 342 and the sequestration portion 334 operable to draw the first or initial volume of bodily fluid into the sequestration portion 334. In other embodiments, the first outlet tubing 338 can be fluidically coupled to a negative pressure source without being coupled to the second outlet tubing 347. For example, in some embodiments, the first outlet tubing 338 can be placed in fluid communication with a vacuum or suction pump, an evacuated container, and/or any other suitable negative pressure source.

In some instances, the first or initial amount of bodily fluid is a volume sufficient to wet or saturate the vent material 342. As described above with reference to the control device 100, the vent material 342 can be configured to transition from an open or venting state or configuration to a closed or sealed configuration in response to being wetted or saturated (e.g., fully saturated). In this manner, transferring the first or initial volume of bodily fluid into the lumen 339 of the first outlet tubing 338 (e.g., the sequestration portion 334) seals the vent material 342, which in turn, allows the pressure within the lumen 339 to equalize with, for example, a pressure in the fluid flow path 333 and/or the lumen 321 of the flexible tubing 320. In some embodiments, the first or initial volume of bodily fluid can be a volume sufficient to fully till the lumen 339 of the first outlet tubing 338 with or without the vent material 342 becoming fully saturated. In such embodiments, the first outlet tubing 338 can include, for example, a valve or selectively permeable membrane configured to limit and/or substantially prevent an outflow of the bodily fluid from the first outlet tubing 338. In some embodiments, such a valve or membrane can be automatically activated, user activated, and/or a combination thereof. In some embodiments, a portion of the actuator 350 can form and/or function as such a valve.

The arrangement of the first outlet tubing 338 (e.g., the sequestration portion 334) can be such that the lumen retains and/or sequesters the initial volume or amount of bodily fluid therein. As described in detail above, contaminants such as, for example, dermally residing microbes or the like dislodged during the venipuncture event, can be entrained and/or included in the initial volume of the bodily fluid and thus, can also be sequestered in the first outlet tubing 338. In some embodiments, fully filling the lumen 339 of the first outlet tubing 338 and/or saturating the vent material 342 can place the actuator 350 in the second position and/or the device 300 in a second state or configuration, in which any subsequent volume of bodily fluid flows through the fluid flow path 333 and into the second outlet 337. In some embodiments, the first outlet tubing 338 can be at least partially transparent allowing a user to visualize when the initial volume has been transferred into the first outlet tubing 338. In such embodiments, the user can engage the actuator 350 to transition the actuator 350 to the second state once the user confirms (e.g., visually) that the desired initial volume is disposed in the first outlet tubing 338. As described above, transitioning the actuator 350 from the first state to the second state can be such that (1) the first outlet tubing 338 is sequestered (e.g., blocked or sealed by a portion of the actuator 350) and (2) the lumen 358 defined by the actuator 350 establishes fluid communication between the second outlet 337 and the inlet 332. The sequestering of the initial amount or volume of bodily fluid in the first outlet tubing 338 (e.g., the sequestration portion 334) prior to collecting or procuring one or more sample volumes of bodily fluid reduces and/or substantially eliminates and amount of contaminants in the one or more sample volumes.

As described in detail above, the second outlet 337 is in fluid communication with one or more fluid collection device(s) (e.g., via the second outlet tubing 347) such that subsequent volume(s) of the bodily fluid can flow from the inlet 332, through the fluid flow path 333, the lumen 358 of the actuator 350, the second outlet 336, and the second outlet tubing 347, and into the fluid collection device(s) (not shown). In some embodiments, the fluid collection device(s) can be any suitable device such as a reservoir, syringe, container, etc. For example, in some embodiments, the fluid collection device can be a reservoir or device that includes and/or defines a negative pressure such as, for example, a single-use disposable collection tube(s), a vacuum-based collection tube(s), a syringe(s), a blood culture bottle(s), and/or the like. In some instances, the fluid collection device can be fluidically connected to the second outlet 337 via the second outlet tubing 347 after the actuator 350 and/or the device 300 is in the second state (e.g., after the initial volume of bodily fluid has been sequestered in the sequestration portion 334). Thus, the negative pressure defined by the fluid collection device can be operable to draw a sample volume of bodily fluid from the patient, through the inlet device 310, through the housing 330 and the actuator 350, and into the fluid collection device. Moreover, with the initial volume of bodily fluid sequestered in the first outlet tubing 338 (e.g., sequestration portion 334), the sample volumes of bodily fluid can be substantially free from contaminants and/or the like. While the fluid collection device is described as being fluidically connected to the second outlet tubing 347 after the actuator 350 is in its second state, in other embodiments, the fluid collection device can be fluidically connected to the second outlet tubing 347 prior to the actuator 350 being placed in its second state. In still other embodiments, a negative pressure associated with the fluid collection device can be operable to draw the first or initial portion of bodily fluid into the lumen 339 of the first outlet tubing 338 (e.g., the sequestration portion 334) without drawing bodily fluid into the fluid collection device prior to the actuator 350 and/or device 300 being placed in the second state.

In some embodiments, one or more of the parts including a diverter, actuator, outlet tubing, and/or sequestration and/or diversion portion can be incorporated into an inlet device and vice versa. For example, FIGS. 8-11 illustrate a fluid control device 400 (also referred to herein as "control device" or "device") according to an embodiment. As described above with reference to the control devices 100, 200, and/or 300, the control device 400 is configured to withdraw and sequester a first portion or amount (e.g., an initial amount) of bodily fluid from a patient such that any subsequently withdrawn amount, portion, and/or volume of bodily fluid is substantially free of contaminants. In some embodiments, portions and/or aspects of the control device 400 are substantially similar in form and/or function to the corresponding portions and/or aspects of the control devices 100, 200, and/or 300 described above with reference to FIG. 1, FIGS. 2-4, and FIGS. 5-7, respectively. Accordingly, such similar portions and/or aspects are not described in further detail herein.

Figure 8:
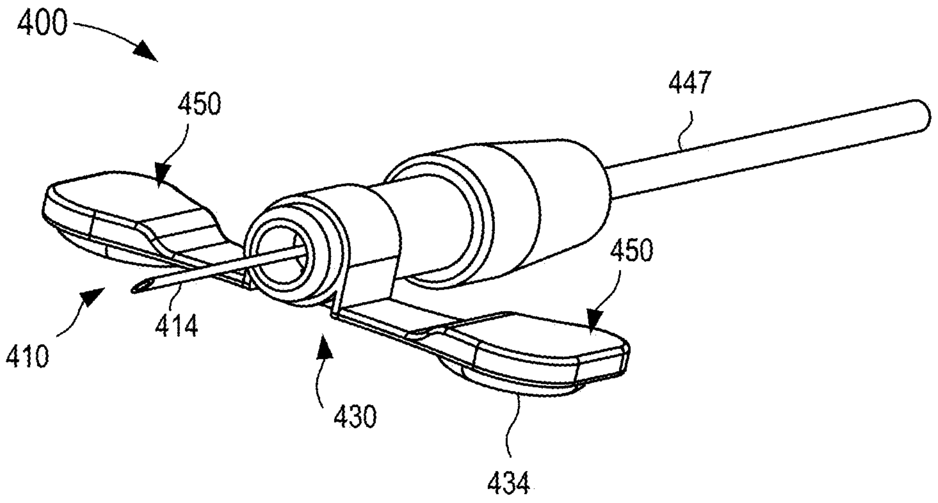
FIGS. 8 and 9 are perspective top and bottom views, respectively, of a fluid control device according to an embodiment.
Figure 9:
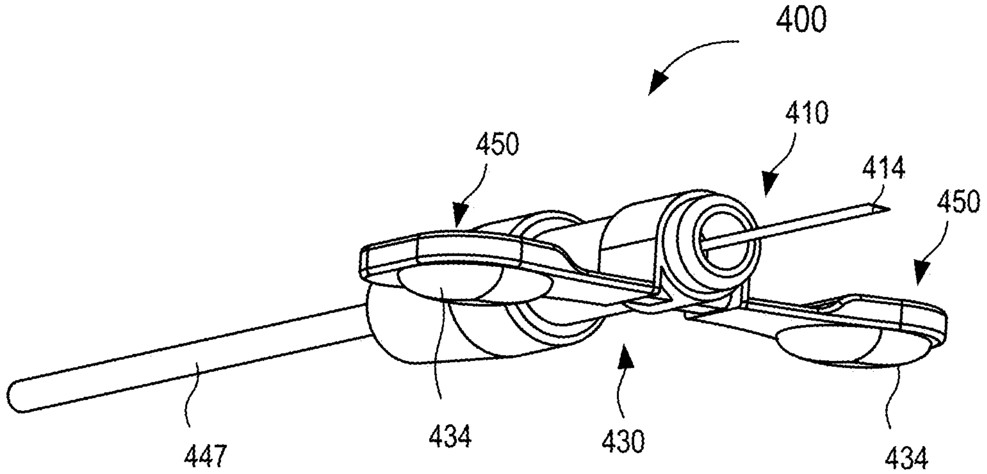

As shown in FIGS. 8 and 9, the control device 400 includes an inlet device 410 and a housing 430 that is at least partially incorporated into an inlet device 410, as described in further detail below. In general, the inlet device 410 can be any suitable device or set of devices configured to establish fluid communication between a bodily fluid source such as, for example, the vasculature of a patient, and one or more fluid collection devices such as fluid collection devices, syringes, evacuated containers, and/or the like (as described in detail above).

As shown in FIGS. 8-11, the arrangement of the control device 400 is such that the housing 430 is integrated into and/or forms a portion of the inlet device 410. The inlet device 410 can be any suitable device(s) such as, for example, an IV catheter, a sharpened catheter or sharpened needle, and/or any other suitable lumen-containing device. For example, in the embodiment shown in FIGS. 8-11, the inlet device 410 is a butterfly needle or other suitable access device having a needle 414, the housing 430, and an outlet or outlet tubing 447. As such, the needle 414 of the inlet device 410 is in fluid communication with one or more fluid flow paths defined by the housing 430 and the one or more fluid flow paths are in fluid communication with the outlet or the outlet tubing 447. Thus, the needle 414 can receive a flow of bodily fluid that can be selectively transferred through the housing 430 to the outlet or outlet tubing 447, as described in further detail herein.

The housing 430 can be any suitable device or set of devices configured to (1) receive a flow of bodily fluid (e.g., from the needle 414), (2) store and sequester a first volume or initial volume of the bodily fluid, and (3) direct or divert a subsequent flow of the bodily fluid to a fluid collection device, as described in further detail herein. The housing 430 includes and/or defines a set of sequestration and/or diversion portions 434, a set of fluid flow paths 433, 464, and 468, and the outlet or outlet tubing 447. In the embodiment shown in FIGS. 8-11, the set of sequestration and/or diversion portions 434 includes two sequestration and/or diversion portions 434 (also referred to herein as "sequestration portions 434"). In other embodiments, the set of sequestration portions 434 can include any suitable number of sequestration and/or diversion portions (e.g., less than two or more than two). As described in further detail herein, each sequestration portion 434 can include and/or can be configured to at least partially function as an actuator 450, which can be manipulated by a user to urge, encourage, and/or draw bodily fluid into or towards the corresponding sequestration portion 434.

As shown in FIG. 8-11, the control device 400 can be arranged as and/or arranged similar to a butterfly needle. The set of sequestration portions 434 of the housing 430 can be housed within and/or can form the "wings" of the butterfly needle. In other words, the inlet device 410 can be modified to include the housing 430 as a body portion thereof (e.g., similar to the body 311 of the inlet device 310) and, as such, the sequestration portions 434 can form what would otherwise be the wings of the inlet device 410 (butterfly needle). In some embodiments, one or more portions of the housing 430 can be formed of a relatively rigid material such as a plastic or the like and can be configured to retain its shape and/or form when exposed to changes in pressure and/or inlet and outlet flows of fluid. Conversely, other portions (e.g., the sequestration portions 434 or the wing portions) of the housing 430 can be formed of a relatively pliable material (e.g., molded rubber, flexible plastic, etc.) and can be configured to elastically deform in response to a compressive force. As such, the portions (e.g., the sequestration portions 434) can be configured to change shape and/or form in response to an applied force, which in turn, results in a change in the volume of the sequestration portion 434. As described in further detail herein, the change in volume within the sequestration and/or diversion portions can result in pressure differentials that can be operable to draw bodily fluid into the sequestration portions 434. It should be noted that, although the sequestration portions 434 are shown in FIGS. 8-11 as forming the wings of the inlet device 410, in other embodiments, the sequestration and/or diversion portion(s) 434 can be external to the inlet device 410 such that a tubing or a fluidic connection (not shown) can be used to connect one or more of the outlets of the housing 430 to the external sequestration and/or diversion portion(s) 434.

Figure 10:
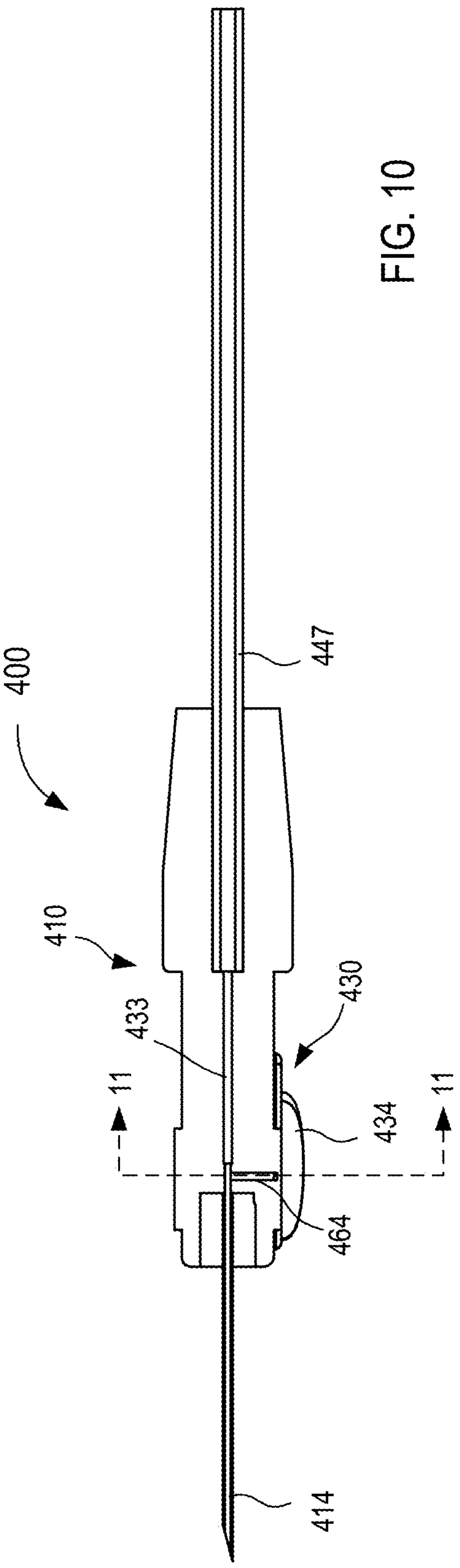
FIG. 10 is a cross-sectional side view of the fluid control device of FIG. 8.
Figure 11:
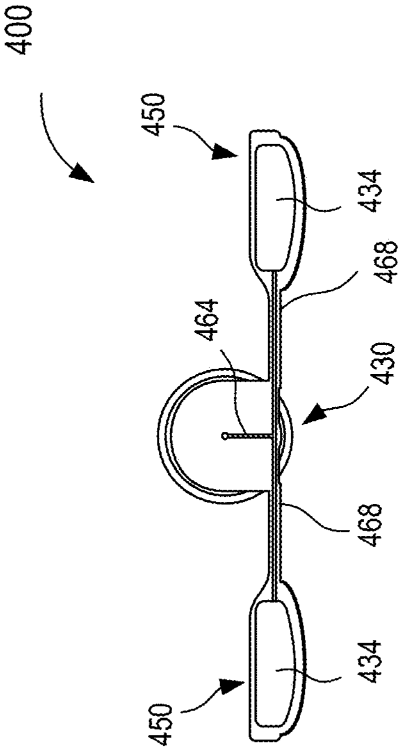
FIG. 11 is a cross-sectional view of the fluid control device of FIG. 10, taken along the line 11-11.
Figure 12:
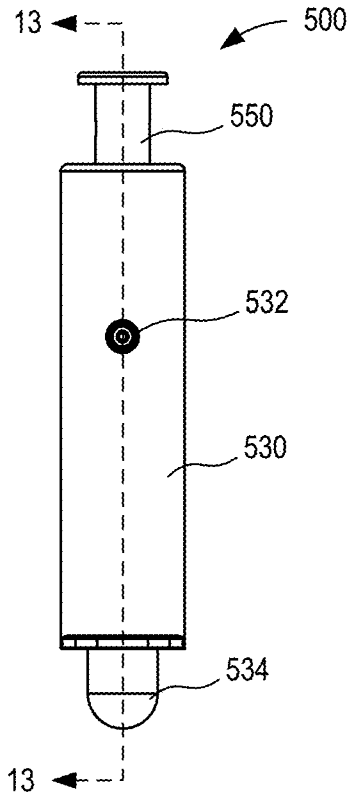
FIG. 12 is a side view of a fluid control device according to an embodiment.

As shown in FIG. 10, the fluid flow path 433 extends through the housing 430 to fluidically couple to a lumen of the needle 414 and a lumen of the outlet or outlet tubing 447. Thus, the fluid flow path 433 establishes fluid communication between the needle 414 and the outlet or outlet tubing 447. Moreover, the housing 430 includes a fluid flow path 464 that branches off the fluid flow path 433 and a fluid flow path 468 that is in fluid communication with the fluid flow path 464 and the sequestration portions 434. For example, in some embodiments, the fluid flow paths 464 and 468 can form a T-shape or Y-shape flow path extending from the fluid flow path 433 (e.g., a central flow path) and ending in the sequestration portions 434, as shown in FIGS. 10 and 11. As such, the housing 430 can receive, for example, an initial flow of bodily fluid from the needle 414 and can selectively allow fluid to flow through at least a portion of the fluid flow paths 433, 464, and/or 468 to the sequestration portions 434, as described in further detail herein. Although not shown in FIGS. 8-11, the housing 430 can include one or more actuators, valve, and/or flow controllers (other than the actuators 450 shown in FIGS. 8-11) that can selectively, permit or block flow of fluid, for example, from the fluid flow path 433 to the fluid flow path 464, thereby isolating and/or sequestering the sequestration portions 434. As described above with reference to the actuators 150, 250, and/or 350, the (one or more) actuator(s) associated with the housing 430 and/or the device 400 can be a switch, a valve, a port, and/or the like, that can directly, or indirectly manipulate and/or control the fluid flow through the housing 430.

In some embodiments, the housing 430 can be configured to divert, direct, and/or otherwise facilitate fluid flow based on a force applied to and/or experienced by a portion of the housing 430 (e.g., a passive force or an active force). For example, in some embodiments, the housing 430 can be configured to divert, direct, and/or otherwise facilitate fluid flow based on one or more pressure differentials created by any suitable manner. Specifically, as described above, the sequestration portions 434 and/or a portion thereof can form and/or can include the actuator(s) 450 (also referred to herein as "actuator portion(s)"). The actuator portion 450 of each sequestration portion 434 can be configured to deform in response an external force (e.g., applied by a user), which in turn, can result in a compression of the sequestration portion 434. The compression can be effected manually by a user performing a pinching or pressing action on the actuator portions 450 of the sequestration portions 434 before placing the needle 414 in contact with the source of bodily fluid (for example, by puncturing a vasculature of a patient to draw blood).

In some embodiments, the compression of the sequestration portions 434 can result in a venting of the sequestration portions 434 and an expelling of the air and/or other contents disposed within the sequestration portion 434. In some embodiments, the venting can be through at least one of the needle 414 or the outlet tubing 447. In other embodiments, the housing 430 can include at least one vent, opening, port, valve, etc. configured to allow air or gas to vent from the sequestration portions 434. In such embodiments, the vent(s) or the like can be configured to allow a unidirectional flow of air and/or gas out of the sequestration portions 434 while limiting and/or preventing a flow of air or gas into the sequestration portions 434. In addition, such vents or the like can permit air or gas to be vented from the sequestration portions 434 while limiting and/or preventing a flow of fluid (e.g., liquid) out of or into the sequestration portions 434. In still other embodiments, the sequestration portions 434 can be evacuated, vented, and/or charged in any, suitable including, for example, exposure to an external negative pressure source.

In some instances, the venting of the sequestration portions 434 can be prior to or after placing the needle 414 in fluid communication with the bodily fluid source. Following venting, when the needle 414 is inserted into a portion of a patient (i.e., placed in communication with the source of bodily fluid), the control device 400 can be in charged and/or primed state. In this state, the force applied on the actuator portions 450 can be maintained and the sequestration portions 434 can be in a deformed, compressed, collapsed, and/or vented configuration (as described above). Once the needle 414 is in fluid communication with the bodily fluid source, the force can be removed from the actuator portions 450 (e.g., the user can release the pinching, squeezing, and/or otherwise compressive force exerted on the actuator portions 450). In response, the sequestration portions 434 can return to an undeformed, uncompressed, and/or non-collapsed configuration, which in turn, results in an increase in a volume within the sequestration portions 434 (e.g., places the device 400 and/or the housing 430 in the first state). The increase in volume inside the sequestration portions 434 produces a negative pressure within the sequestration portions 434 that can draw, urge, and/or encourage flow of bodily fluid preferentially into and/or through a portion of the fluid flow path 433, through the fluid flow paths 464 and 468 and into the sequestration portions 434. Thus, the sequestration portions 434 can receive an initial volume or first volume of bodily fluid withdrawn from the bodily fluid source (e.g., the patient).

Although not shown in FIGS. 8-11, the device 400 can also include one or more actuators, membranes, valves, ports, etc. (other than the actuators 450) placed in or along the fluid flow paths 433, 464, and/or 468 to actively or passively permit or block flow in particular directions (as described in detail above). In some embodiments, at least a portion of the housing 430 and/or the sequestration portions 434 can have and/or can include a shape, material, configuration, and/or device configured to facilitate bodily fluid flow toward the sequestration portions 434. For example, in some embodiments, the sequestration portions 434 and/or a portion thereof can include and/or can be formed of an absorbent material, a hydrophilic material, a wicking material, a textured or pitted surface, and/or any other suitable means of absorbing, attracting, and/or retaining bodily fluid, such as those described in detail above with reference to the device 100. Moreover, in some embodiments, a size, shape, and/or configuration of the fluid flow paths 433, 464, and 468 and/or portions thereof can be configured to control, modulate, regulate, restrict, direct, etc., fluid flow and/or a negative pressure exerted therethrough. For example, in some embodiments, a size and/or diameter of the fluid flow paths 464 and 468 can be smaller than a size and/or diameter of the fluid flow path 433, which in turn, can reduce, restrict, and/or modulate an amount of negative pressure (produced within the sequestration portions 434) that is exerted on, in, and/or through the fluid flow path 433.

In some instances, the flow of bodily fluid into the sequestration portion 434 can cease gradually or abruptly due to any suitable active or passive mechanism. For example, the flow into the sequestration portion 434 can cease in response to a desired initial volume of bodily fluid being disposed in the sequestration portions 434. In some instances, for example, the flow of bodily fluid into the sequestration portions 434 can stop in response to an equalization of the pressure differential that was otherwise sufficient to draw the initial volume into the sequestration portions 434. In some instances, the flow of bodily fluid into the sequestration portion 434 can stop when the negative pressure is insufficient to draw bodily fluid into, for example, the fluid flow paths 464 and/or 468. For example, as described above, the size, shape, diameter, and/or configuration of any of the fluid flow paths 433, 464, and/or 468 can be selected, designed, tuned, and/or otherwise modified to modulate fluid flow and/or negative pressure therein. As such, in some embodiments, the cross-sectional area of the fluid flow path 464 can be smaller than the cross-sectional area of the fluid flow path 433. Thus, in some embodiments, the flow of bodily fluid into the sequestration portions 434 can stop when the negative pressure is insufficient to draw bodily fluid through the fluid flow path 464 (e.g., regardless of whether there is a substantial equalization of pressure). In other embodiments, the fluid flow paths 433, 464, and/or 468 and/or any suitable portion thereof can include an absorbent material, a semi-permeable membrane, a valve, and/or the like configured to transition to a sealed or closed configuration in response to a flow of the initial volume therethrough. In some embodiments, such a valve; membrane, material, and/or seal can be time-based or the like (as described above). In some embodiments, the flow of bodily fluid into the sequestration portions 434 can stop when the sequestration portions 434 are fully filled. For example, in some embodiments, the sequestration portions 434 and/or at least a portion thereof can be at least partially transparent allowing a user to visually confirm when the sequestration portions 434 are fully filled. In other embodiments, the sequestration portions 434 and/or any suitable portion of the device 400 can provide an indication (e.g., a visual indication, an audible indication, a haptic indication, etc.) when the desired initial volume is disposed in the sequestration portions 434.

With the initial volume of bodily fluid disposed in the sequestration portions 434, the device 400 can be transitioned from the first state to the second state such that bodily fluid can flow from the needle 414, through at least a portion of the fluid flow path 433, and to the outlet or outlet tubing 447. Although not shown in FIGS. 8-11, the outlet and/or outlet tubing 447 can be connected to a fluid collection device such as those described herein (e.g. a syringe, a vacuum-based collection tube or collection container, a sample bottle, a culture bottle, etc.). Moreover, when the device 400 is placed in the second state, the initial volume of bodily fluid, which can contain contaminants and/or the like, is sequestered in the sequestration portions 434. For example, in some embodiments, the equalization of the negative pressure otherwise operable to draw bodily fluid into the sequestration portions 434 can be such that subsequent volumes of bodily fluid flow through the fluid flow path 433 without entering the fluid flow path 464. In other embodiments, the sequestration portions 434 and/or the initial volume of bodily fluid contained therein can be sequestered in any suitable manner such as those described above. Thus, with the initial volume of bodily fluid sequestered in the sequestration portions 434, subsequent volumes of bodily fluid, which are substantially free of contaminants, can be drawn from the patient and into the collection device (e.g., fluid collection device).

Although not shown in FIGS. 8-11, in some embodiments, the device 400 can include an actuator, valve, switch, and/or any other suitable flow controller or mechanism configured to transition the device 400 from the first state to the second state. For example, in some embodiments, the device 400 can include a valve or a flow controller with one or more fluid flow paths. In such embodiments, the valve and/or flow controller can be transitioned in response to a user engaging an actuator such as a dial, switch, button, rotor, slider, and/or the like. In embodiments in which the device 400 is configured as a butterfly needle and/or the like, the user can be configured to transition the valve and/or flow controller by transitioning, moving, rotating, and/or otherwise engaging at least one of the wings of the butterfly needle. For example, in some embodiments, at least one of the wings (e.g., including the sequestration portion 434 formed thereby) of the butterfly needle can be rotated about the housing 430, which in turn, can rotate a valve or other flow controller configured to control a flow of bodily fluid from the needle 414 to either the fluid flow path 464 (and to the sequestration portion 434) or the fluid flow path 433 (and to the outlet tubing 447). In other embodiments, such a valve or flow controller can be actuated and/or transitioned in any other suitable manner such as those described herein.

While the control device 400 is described above as being evacuated and/or vented in response to a force exerted on the sequestration portions 434 (e.g., a compression force), in other embodiments, a sequestration portion can be pre-charged and/or vented or evacuated in any suitable manner. For example, FIGS. 12-15 illustrate a fluid control device 500 (also referred to herein as "control device" or "device") according to an embodiment. As described above with reference to the control devices 100, 200, 300, and/or 400, the control device 500 is configured to withdraw and sequester a first portion or amount (e.g., an initial amount) of bodily fluid from a patient such that any subsequently withdrawn amount, portion, and/or volume of bodily fluid is substantially free of contaminants. In some embodiments, portions and/or aspects of the control device 500 are substantially similar in form and/or function to the corresponding portions and/or aspects of the control devices 100, 200, 300, and/or 400 described above. Accordingly, such similar portions and/or aspects are not described in further detail herein.

As shown in FIGS. 12-15, the control device 500 includes a housing 530 and an actuator 550. The housing 530 can be any suitable device or set of devices configured to (1) receive a flow of bodily fluid, (2) store and sequester a first volume or initial volume of the bodily, fluid (or receive a device or container configured to store and sequester the first volume), and (3) direct or divert a subsequent flow of the bodily fluid to a fluid collection device, as described in further detail herein. The housing 530 can be any suitable shape, size, and/or configuration. For example, in some embodiments, the housing 530 can be similar to any of the housings described herein.

The housing 530 includes an inlet 532 and an outlet 536. The inlet 532 of the housing 530 can be physically and fluidically coupled (either directly or indirectly) to any suitable device configured to place the inlet 532 in fluid communication with a bodily fluid source. For example, in some embodiments, the inlet 532 can be coupled to an inlet device (e.g., similar to those described herein), a needle, a flexible tubing, and/or any other lumen-containing device. The outlet 536 is in fluid communication with and/or is configured to be placed in fluid communication with a fluid collection device (not shown in FIGS. 12-15) such as a fluid collection device, syringe, culture bottle, and/or the like. The fluid collection device can be similar to any of the fluid collection devices described above with reference to the control device 100.

Figure 13:
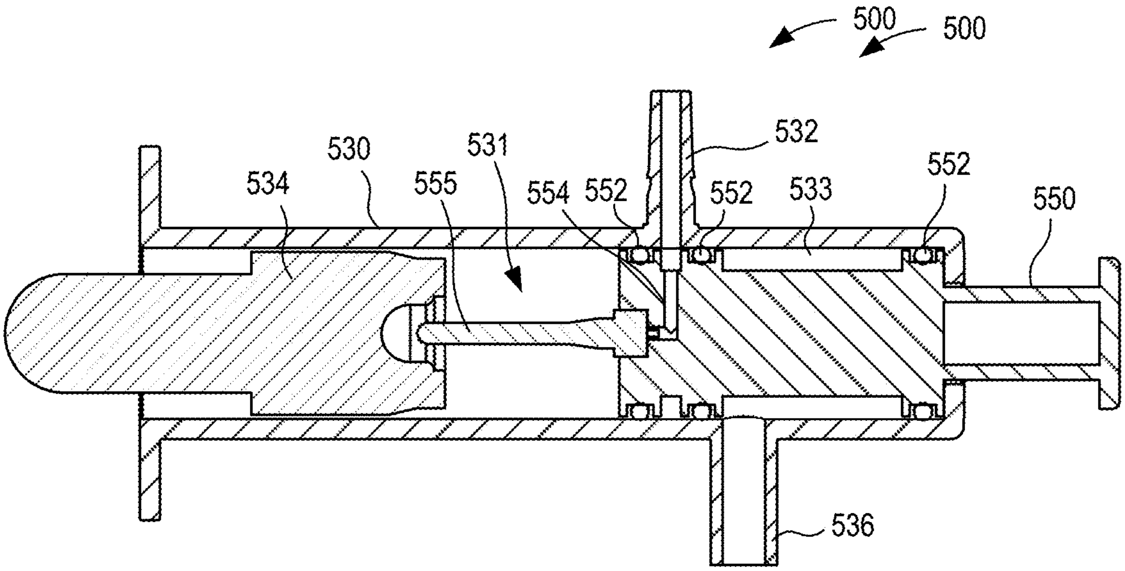
FIGS. 13-15 are cross-sectional views of the fluid control device illustrated in FIG. 12, taken along the line 13-13, in a first state or configuration, a second state or configuration, and a third state or configuration, respectively.

The housing 530 defines an inner volume 531 configured to define and/or form one or more fluid flow path 533. As described in further detail herein, in some instances, the device 500 can be controlled, manipulated, and/or implemented such that the fluid flow path 533 establishes fluid communication with the inlet 532 and the outlet 536. In addition, the inner volume 531 of the housing 530 is configured to receive at least a part of the actuator 550 and at least a part of a sequestration and/or diversion portion or device 534 (referred to herein as "sequestration device" 534). For example, as shown in FIG. 13, the housing 530 can have and/or can define open-end portions configured to allow access to the inner volume 531 of the housing 530.

While the sequestration portions 134, 234, 334, and/or 434 have been described herein as being formed by a portion of the housings 130, 230, 330, and/or 430, respectively, in the embodiment shown in FIGS. 12-15, the sequestration device 534 can be formed independent of the housing 530 and configured to be inserted through one of the end portions of the housing 530 and into the inner volume 531. Moreover, the devices 100, 200, 300, and/or 400 are described above as including and/or implementing various methods for venting and/or evacuating the sequestration portions 134, 234, 334, and/or 434, respectively, to reduce a pressure therein, in the embodiment shown in FIGS. 12-15, the sequestration device 534 can be a pre-charged or evacuated container such as a Vacutainer® or other negative pressure vessel configured to receive a fluid.

In some embodiments, the sequestration device 534 can be pre-charged or previously, evacuated prior to being inserted into the housing 530. For example, in some instances, the sequestration device 534 can be pre-charged and/or evacuated during manufacturing. Moreover, in some embodiments, the control device 500 can be compatible with any suitable sequestration device 534 such as, for example, known evacuated containers (e.g., Vacutainers® and/or the like), custom evacuated containers, and/or any other suitable device. As described in further detail herein, a reduced or negative pressure within the pre-charged sequestration device 534 can be operable in drawing an initial volume of bodily fluid through at least a portion of the control device 500 and into the sequestration device 534. As such, the sequestration device 534 can be similar in at least function to the sequestration portions 134, 234, 334, and/or 434 described herein.

As described above, the actuator 550 is configured to be at least partially disposed within the inner volume 531 of the housing 530. For example, in some embodiments, at least a portion of the actuator 550 can be inserted through one of the end portions of the housing 530 (e.g., the end opposite the sequestration device 534) and into the inner volume 531. The actuator 550 can be any suitable member, device, mechanism, etc. configured to transition between at least two different operating states to selectively control fluid flow through the housing 530. For example, as described above with respect to the actuators 150, 250, 350, and/or 450, the actuator 550 can be a switch, a valve, a port, a membrane, a movable channel, a clamp, a plunger, a moveable member, and/or the like configured to manipulate fluid flow (either directly or indirectly) through the housing 530.

In the embodiment shown in FIGS. 12-15, the actuator 550 is a moveable member or plunger, defining a fluid flow path 554 configured to be placed, at least temporarily, in fluid communication with the inlet 532. In addition, the actuator 550 has or includes a set of seals 552 and an outlet member 555. For example, as shown in FIG. 13, the actuator 550 can include three seals 552 that are arranged around an outer surface or portion of the actuator 550 and are configured to be in contact with an inner surface of the housing 530 that defines at least a portion of the inner volume 531. More particularly, each seal 552 can be disposed in a desired and/or predetermined position along the actuator 550 and can be in contact with at least a portion of an outer surface of the actuator 550 and at least a portion of the inner surface of the housing 530 such that each seal 552 forms a substantially fluid tight seal therebetween.

The outlet member 555 is included in and/or coupled to the actuator 550 and is in fluid communication with the fluid flow path 554, as shown in FIG. 13. More particularly, the outlet member 555 can define a lumen (not shown) that is in fluid communication with the fluid flow path 554. For example, in some embodiments, the outlet member 555 can be a needle or sheathed needle, a coupler, an engagement member, and/or any other suitable lumen-defining or containing member. As described in further detail herein, the outlet member 555 is configured to engage and/or otherwise establish fluid communication with the sequestration device 534 when the sequestration device 534 is inserted into the inner volume 531 of the housing 530 such that the lumen defined by the outlet member 555 establishes fluid communication between the fluid flow path 554 of the actuator 550 and the sequestration device 534.

As described above with reference to the actuators 150, 250, 350, and/or 450, the actuator 550 is configured to be transitioned between two or more states and/or configurations to selective control, direct, divert, and/or allow a flow of fluid through at least a portion of the device 500. For example, in some embodiments, the actuator 550 can have a first state and/or configuration in which a first portion of the inner volume 531 of the housing 530 places the inlet 532 in fluid communication with the fluid flow path 554 of the actuator 550 (see e.g., FIGS. 13 and 14). In addition, the actuator 550 can have and/or can be placed in a second state and/or configuration in which (1) the fluid flow path 554 of the actuator is sequestered from the inlet 532, and (2) a second portion of the inner volume 531 (e.g., the fluid flow path 533) places the inlet 532 in fluid communication with the outlet 536 (see e.g., FIG. 15), as described in further detail herein.

In some embodiments, the device 500 can be in a first state and/or configuration prior to use (e.g., during shipping, storage, and/or prior to placing the device 500 in fluid communication with a bodily fluid source such as a patient). For example, in some embodiments the actuator 550 can be disposed in its first state and/or configuration such that the inlet 532 is in fluid communication with the fluid flow path 554 defined by the actuator 550, as shown in FIG. 13. Moreover, in some implementations, the sequestration device 534 can be outside of the housing 530 when the device 500 is in the first state or configuration or can be inserted into the housing 530 such that fluid communication is not yet established between the sequestration device 534 and the outlet member 555 (see e.g., FIG. 13). In some embodiments, the sequestration device 534 can be in a sealed or closed state prior to engaging or being engaged by the outlet member 555 (e.g., when the device 500 is in the first state and/or configuration). As described in detail above, the sequestration device 534 can be an evacuated container and/or any other suitable container, vessel, and/or reservoir having a reduced or negative pressure. Thus, when the device 500 is in the first state and/or configuration, an inner volume of the sequestration device 534 (that defines and/or has the inner volume in a reduced or negative pressure state) is sequestered and/or fluidically isolated from the device 500.

The actuator 550 can also be in its first state and/or configuration when the device 500 is in the first state. For example, as shown in FIG. 13, the actuator 550 can be in a position such that a first seal 552 is disposed on a first side of the inlet 532 and a second seal 552 (e.g., an adjacent seal) is disposed on a second, opposite side of the inlet 532. Similarly, the arrangement of the actuator 550 can be such that the fluid flow path 554 can extend through a portion of the actuator 550 with the first seal 552 disposed on a first side of the portion of the actuator 550 and the second seal 552 disposed on the second side of the portion of the actuator 550 In other words, the portion of the actuator 550 through which the fluid flow path 554 extends is disposed between the first and second seals 552, Accordingly, when the actuator 550 is in the first state and/or configuration, the portion of the inner volume 531 defined between the first and second seals 552 places the inlet 532 in fluid communication with the fluid flow path 554 defined by the actuator 550, as shown in FIG. 13.

In some instances, the device 500 can be placed in fluid communication with the bodily fluid source when the device 500 is in the first state and/or configuration. For example, in some instances, the inlet 532 can be placed in fluid communication with an inlet device (e.g., such as those described herein), a needle, a lumen-containing device, and/or any other suitable device. For example, in some instances, the inlet 532 can be coupled to flexible tubing or the like that, in turn, is fluidically coupled to an inlet device (not shown) such as a butterfly needle. In such instances, the inlet device can be in fluid communication with the bodily fluid source (e.g., can be at least partially inserted into a patient and/or otherwise in fluid communication with a source of bodily fluid outside of a patient). As such, the inlet 532 can be placed in fluid communication with the bodily fluid source, as described in detail above. Moreover, with the actuator 550 in the first state, position, and/or configuration, the portion of the inner volume 531 of the housing 530 defined between the first and second seals 552 places the inlet 532 in fluid communication with the fluid flow path 554 and the outlet member 555 of the actuator 550.

Figure 14:
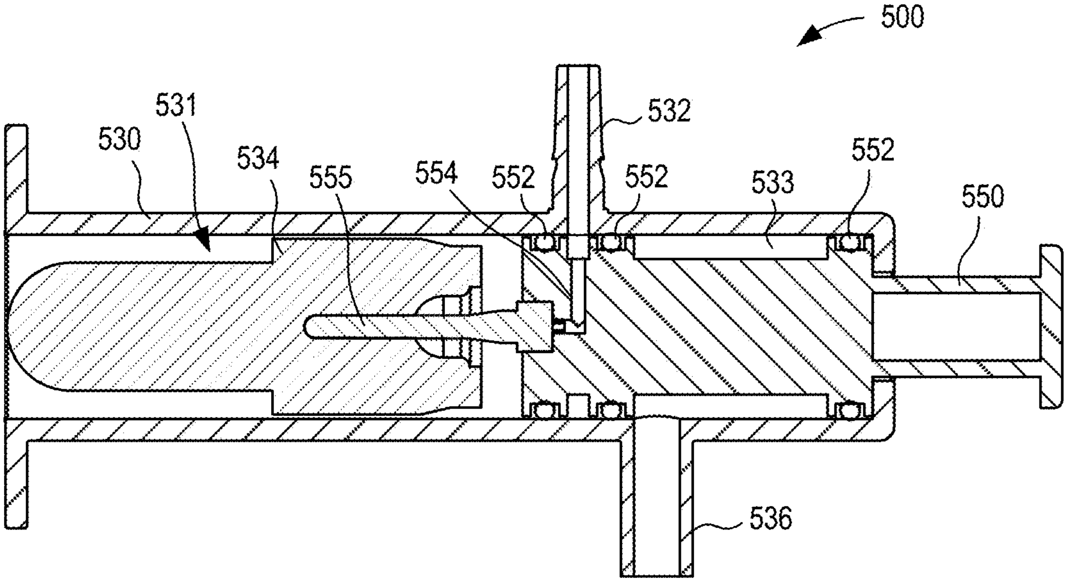

In some instances, the device 500 can be placed in and/or transitioned to a second state or configuration once the inlet 532 is placed in fluid communication with the bodily fluid source example, as shown in FIG. 14, the device 500 can be in the second state and/or configuration when the sequestration device 534 is engaged with and/or by the outlet member 555 of the actuator 550. More particularly, in some instances, a user can advance, push, move, and/or otherwise insert the sequestration device 534 into the housing 530 such that the outlet member 555 engages, pierces, punctures, ruptures, and/or otherwise opens a surface or port of the sequestration device 534, thereby placing the device 500 in the second state and/or configuration. As the sequestration device 534 engages the outlet member 555 (e.g., as the outlet member 555 pierces or punctures a port or frangible surface of the sequestration device 534), the lumen of the outlet member 555 is placed in fluid communication with the inner volume of the sequestration device 534. Thus, the reduced or negative pressure within the sequestration device 534 generates or otherwise results in a suction force being exerted through the lumen of the outlet member 555.

As shown in FIG. 14, the actuator 550 can remain in its first state, position, and/or configuration when the sequestration device 534 is moved relative to the housing 530 (e.g., when the device 500 is placed in the second state and/or configuration). As described in detail above with reference to the devices 100, 200, 300, and/or 400, the negative pressure differential or suction force generated by establishing fluid communication between the sequestration device 534 and the outlet member 555 can be operable to draw bodily fluid from the bodily fluid source (e.g., the patient), through the inlet 532 of the device 500, through the portion of the inner volume 531 defined between the first and second seals 552, through the fluid flow path 554 and the outlet member 555 of the actuator 550, and into the sequestration device 534. Thus, the sequestration device 534 can receive an initial volume of bodily fluid from the bodily fluid source (e.g., the patient). As such, using the pre-charged sequestration device 534 can be substantially similar in at least function to venting and/or evacuating the sequestration devices (or portions) 134, 234, 334, and/or 434 described above. Moreover, in some instances, such an arrangement can allow for the use of multiple sequestration device 534 by replacing a full sequestration device 534 with a new sequestration device 534 that is sealed and evacuated (e.g., a new Vacutainer® or the like).

Once an initial volume of bodily fluid is transferred into the sequestration device 534, the device 500 can be placed in and/or transitioned to a third state or configuration. For example, in some embodiments, the actuator 550 can be switched or transitioned from the first state, position, and/or configuration (FIGS. 13 and 14) to a second state, position, and/or configuration (FIG. 15) to place the device 500 in the third state and/or configuration. In the embodiment shown in FIGS. 12-15, the actuator 550 can be switched and/or transitioned in response to a force exerted by a user on a portion of the actuator 550 that moves the actuator 550 relative to the housing 530. In some instances, the actuator 550 can be moved relative to the housing 530 in a direction that is substantially opposite the direction in which the sequestration device 534 was inserted into the housing 530. In other embodiments, the actuator 550 can be switch, transitioned, moved, and/or reconfigured in any suitable manner such as any of those described herein.

Figure 15:
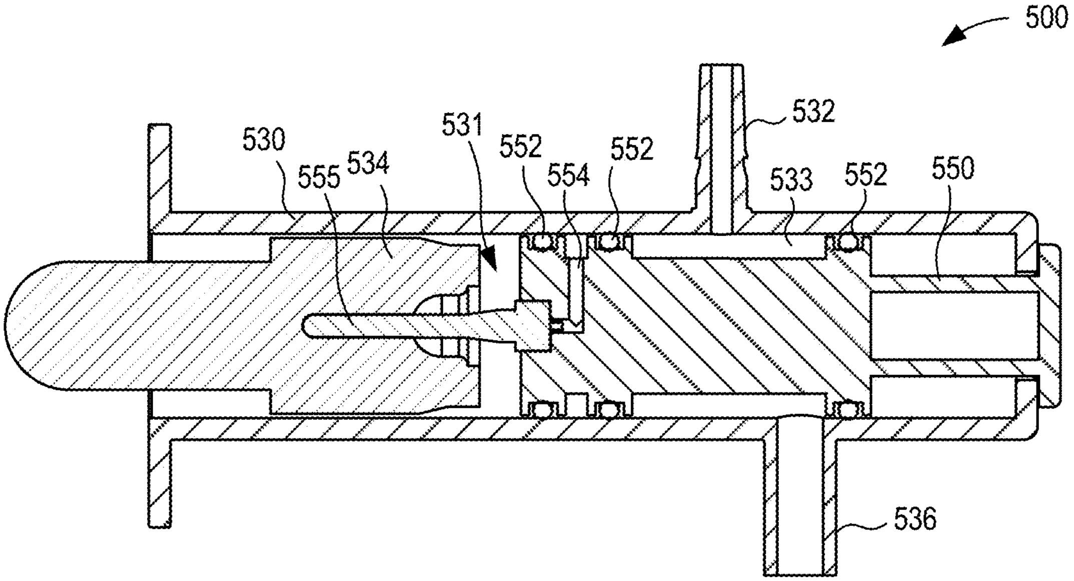
Figure 16:
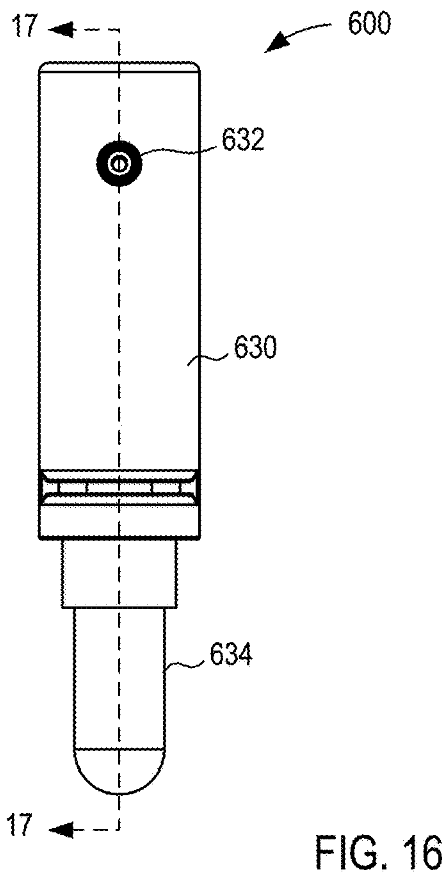
FIG. 16 is a side view of a fluid control device according to an embodiment.

When in the second state, position, and/or configuration, the actuator 550 can allow fluid communication to be established between the inlet 532 and the outlet 536, as shown in FIG. 15. In addition, the actuator 550 can be configured to sequester the fluid flow path 554 from the inlet 532 and the outlet 536 of the housing 530, which in turn, sequesters the initial volume of bodily fluid from the inlet 532 and the outlet 536. In some instances, the initial volume of bodily fluid can include contaminants and/or undesirable material that is likewise sequestered in the sequestration device 534 and/or from the inlet 532 and the outlet 536. In some implementations, the sequestration device 534 can be removed from the housing 530 when the actuator 550 is transitioned to the second state, position, and/or configuration. In other implementations, the sequestration device 534 can be removed from the housing 530 after receiving the initial volume but prior to the actuator 550 being transitioned to the second state, position, and/or configuration, In still other implementations, the sequestration device 534 need not be removed from the housing 530 (e.g., can remain engaged with the outlet member 555). In such implementations, sequestering the fluid flow path 554 from the inlet 532 and the outlet 536, in turn, sequesters the sequestration device 534 and/or the initial volume disposed therein from at least the inlet 532 and the outlet 536.

As described in detail above with reference to the devices 100, 200, 300, and/or 400, with the actuator 550 in the second configuration and/or position, a portion of the inner volume 531 defined between, for example, the second seal 552 and a third seal 552 defines the fluid flow path 533 that places the inlet 532 in fluid communication with the outlet 536, as shown in FIG. 15. As such, subsequent volumes of bodily fluid withdrawn from the patient can be substantially free from contaminants and can be transferred from the inlet 532, through the portion of the inner volume 531 (e.g., the fluid flow path 533) and the outlet 536, and into one or more fluid collection devices coupled to the outlet 536. In some embodiments, the fluid collection device(s) can be any suitable device such as a reservoir, syringe, container, and/or any fluid collection device described herein. Thus, the device 500 can be configured to procure one or more volumes of bodily fluid (e.g., used for bodily fluid sampling or the like) that are substantially free of contaminants.

While the device 500, and more particularly the actuator 550, are described above as being transitioned, switched, moved, and/or reconfigured in response to a force exerted by a user on a portion of the actuator 550, in other embodiments, an actuator can be transitioned between states in any suitable manner and/or in response to any suitable force. For example, FIGS. 16-19 illustrate a fluid control device 600 (also referred to herein as "control device" or "device") according to an embodiment. As described above with reference to the control devices 100, 200, 300, 400, and/or 500, the control device 600 is configured to withdraw and sequester a first portion or amount (e.g., an initial amount) of bodily fluid from a patient such that any subsequently, withdrawn amount, portion, and/or volume of bodily fluid is substantially free of contaminants. In some embodiments, portions and/or aspects of the control device 600 are substantially similar in form and/or function to the corresponding portions and/or aspects of at least the control device 500 described above with reference to FIGS. 12-15. Accordingly, such similar portions and/or aspects are not described in further detail herein.

As shown in FIGS. 16-19, the control device 600 includes a housing 630 and an actuator 650. The housing 630 can be any suitable device or set of devices configured to (1) receive a flow of bodily fluid, (2) store and sequester a first volume or initial volume of the bodily, fluid (or receive a device or container configured to store and sequester the first volume), and (3) direct or divert a subsequent flow of the bodily fluid to a fluid collection device, as described in further detail herein. The housing 630 can be any suitable shape, size, and/or configuration. For example, in some embodiments, the housing 630 can be substantially similar to the housing 530 described above with reference to FIGS. 12-15.

The housing 630 includes an inlet 632 and an outlet 636, and defines an inner volume 631. The inlet 632 of the housing 630 can be physically and fluidically coupled (either directly or indirectly) to any suitable device configured to place the inlet 632 in fluid communication with a bodily fluid source, as described above with reference to the inlet 532. The outlet 636 is in fluid communication with and/or is configured to be placed in fluid communication with a fluid collection device (not shown in FIGS. 16-19) such as a fluid collection device or reservoir, syringe, culture bottle, and/or the like, as described above with reference to the device 600. The inner volume 631 of the housing 630 is configured to define and/or form one or more fluid flow path 633. As described above with reference to the device 500, the device 600 can be controlled, manipulated, and/or implemented such that the fluid flow path 633 establishes fluid communication with the inlet 632 and the outlet 636. The inner volume 631 of the housing 630 is configured to receive at least a part of a sequestration and/or diversion portion or device 634 (referred to herein as "sequestration device" 634). The sequestration device 634 can be similar to or substantially the same as the sequestration device 534 described above and thus, the sequestration device 634 is not described in further detail herein.

Figure 17:
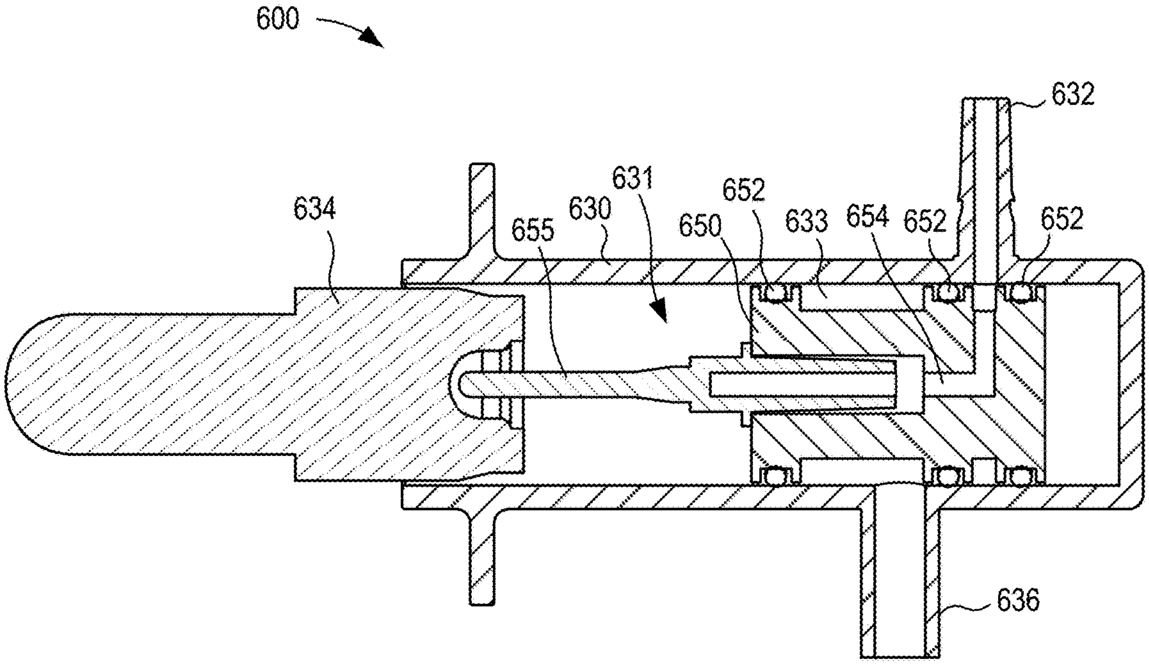
FIGS. 17-19 are cross-sectional views of the fluid control device illustrated in FIG. 16, taken along the line 17-17, in a first state or configuration, a second state or configuration, and a third state or configuration, respectively.
Figure 18:
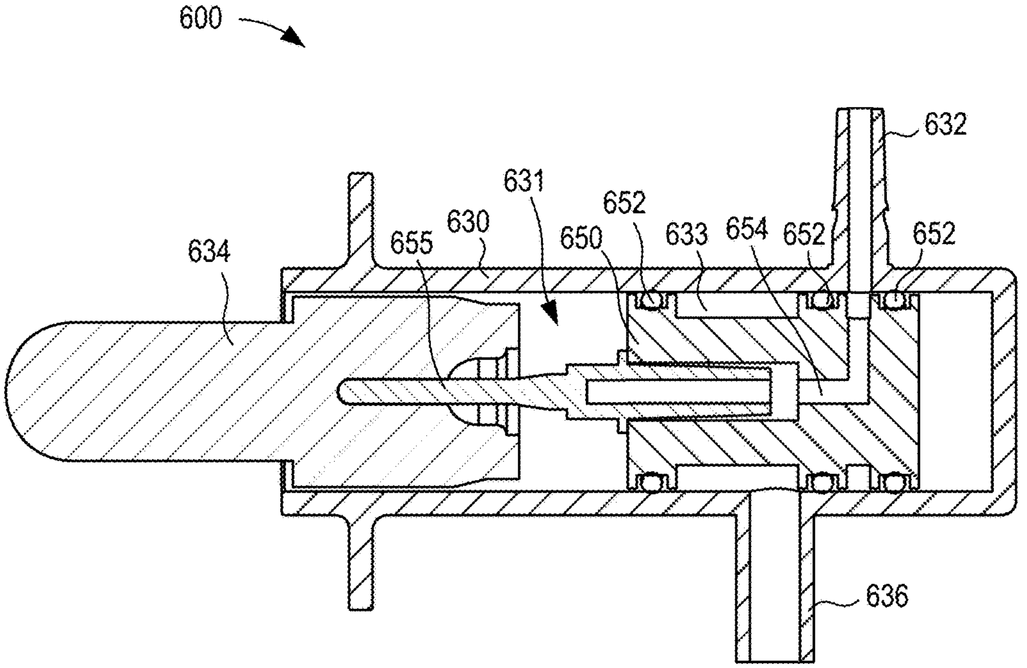
Figure 19:
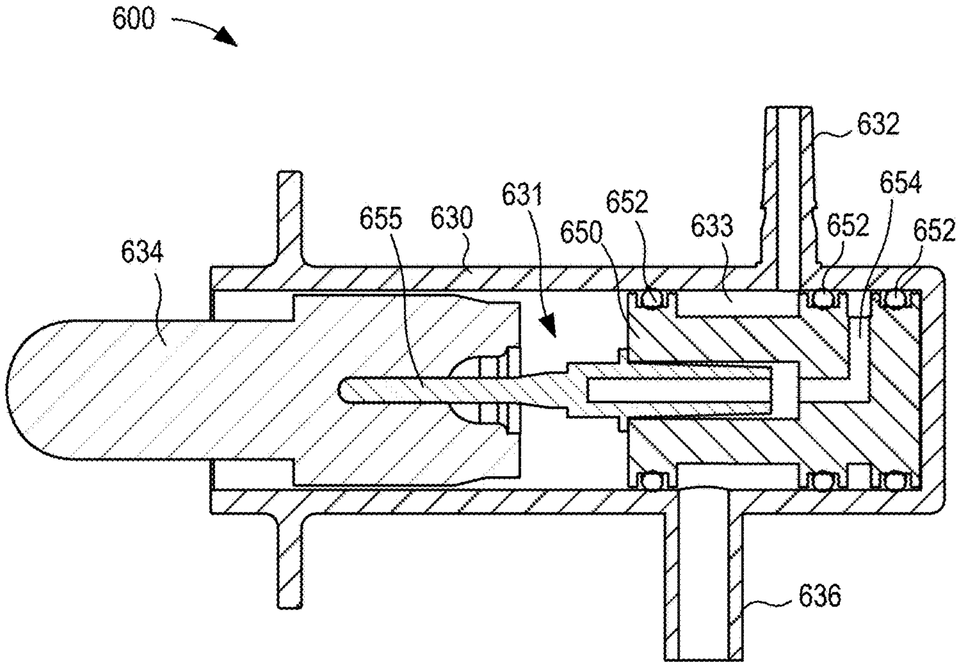

As shown in FIGS. 17-19, the actuator 650 of the device 600 is configured to be at least partially disposed within the inner volume 631 of the housing 630. The actuator 650 can be any suitable member, device, mechanism, etc configured to transition between at least two different operating states to selectively control fluid flow through the housing 630. For example, as described above with respect to the actuator 550, the actuator 650 can be a switch, a valve, a port, a membrane, a movable channel, a clamp, a plunger, a moveable member, and/or the like configured to manipulate fluid flow (either directly or indirectly) through the housing 630.

In the embodiment shown in FIGS. 16-19, the actuator 650 is a moveable member or plunger, defining a fluid flow path 654 configured to be placed, at least temporarily, in fluid communication with the inlet 632. In addition, the actuator 650 has or includes a set of seals 652 and an outlet member 655. For example, as shown in FIG. 17, the actuator 650 can include three seals 652 that are arranged around an outer surface or portion of the actuator 650 and are configured to be in contact with an inner surface of the housing 630 that defines at least a portion of the inner volume 631. Each seal 652 can be disposed in a desired and/or predetermined position along the actuator 650 and can be in contact with at least a portion of an outer surface of the actuator 650 and at least a portion of the inner surface of the housing 630 such that each seal 652 forms a substantially fluid tight seal therebetween, as described in detail above with reference to the actuator 550.

The outlet member 655 is included in and/or coupled to the actuator 650 and is in fluid communication with the fluid flow path 654, as shown in FIG. 17. More particularly, the outlet member 655 can define a lumen (not shown) that is in fluid communication with the fluid flow path 654. For example, the outlet member 655 can be a needle or sheathed needle, a coupler, an engagement member, and/or any other suitable lumen-defining or containing member. As described above with reference to the outlet member 555, the outlet member 655 is configured to engage and/or otherwise establish fluid communication with the sequestration device 634 when the sequestration device 634 is inserted into the inner volume 631 of the housing 630 such that the lumen defined by the outlet member 655 establishes fluid communication between the fluid flow path 654 of the actuator 650 and the sequestration device 634.

The actuator 650 is configured to be transitioned between two or more states and/or configurations to selective control, direct, divert, and/or allow a flow of fluid through at least a portion of the device 600, as described above with reference to the actuator 550. For example, in some embodiments, the actuator 650 can have a first state and/or configuration in which a first portion of the inner volume 631 of the housing 630 places the inlet 632 in fluid communication with the fluid flow path 654 of the actuator 650 (see e.g., FIGS. 17 and 18). In addition, the actuator 650 can have and/or can be placed in a second state and/or configuration in which (1) the fluid flow path 654 of the actuator is sequestered from the inlet 632, and (2) a second portion of the inner volume 631 (e.g., the fluid flow path 633) places the inlet 632 in fluid communication with the outlet 636 (see e.g., FIG. 19). In some embodiments, some aspects and/or functions of the actuator 650 can be similar to corresponding aspects and/or functions of the actuator 550. Such aspects and/or functions are not described in further detail herein and should be considered similar in at least form and/or function unless expressly stated otherwise.

In some embodiments, the device 600 can be in a first state and/or configuration prior to use (e.g., during shipping, storage, and/or prior to placing the device 600 in fluid communication with a bodily fluid source such as a patient). For example, in some embodiments the actuator 650 can be disposed in its first state and/or configuration such that the inlet 632 is in fluid communication with the fluid flow path 654 defined by the actuator 650, as shown in FIG. 17. As described above with reference to the device 500, the sequestration device 634 can be outside of the housing 630 when the device 600 is in the first state or configuration or can be inserted into the housing 630 such that fluid communication is not yet established between the sequestration device 634 and the outlet member 655 (see e.g., FIG. 17). Thus, when the device 600 is in the first state and/or configuration, an inner volume of the sequestration device 634 (that defines and/or is other in the reduced or negative pressure state) is sequestered and/or fluidically isolated from the device 600.

The actuator 650 can also be in its first state and/or configuration when the device 600 is in the first state such that the inlet 632 and a portion of the actuator 650 through which the fluid flow path 654 extends are each disposed between a first and a second seal 652 (e.g., adjacent seals 652 (see e.g., FIG. 17)). Thus, when the actuator 650 is in the first state and/or configuration, a portion of the inner volume 631 defined between the first and second seals 652 places the inlet 632 in fluid communication with the fluid flow path 654 defined by the actuator 650, as described in detail above with reference to the device 500, In some instances, the device 600 can be placed in fluid communication with the bodily fluid source when the device 600 is in the first state and/or configuration. For example, in some instances, the inlet 632 can be placed in fluid communication with an inlet device (e.g., such as those described herein), a needle, a lumen-containing device, and/or any other suitable device, as described above with reference to the device 500. Accordingly, with the actuator 650 in the first state, position, and/or configuration, the portion of the inner volume 631 of the housing 630 defined between the first and second seals 652 places the inlet 632 in fluid communication with the fluid flow path 654 and the outlet member 655 of the actuator 650.

In some instances, the device 600 can be placed in and/or transitioned to a second state or configuration once the inlet 632 is placed in fluid communication with the bodily fluid source example, as shown in FIG. 18, the device 600 can be in the second state and/or configuration when the sequestration device 634 is engaged with and/or by the outlet member 655 of the actuator 650. More particularly, in some instances, a user can advance, push, move, and/or otherwise insert the sequestration device 634 into the housing 630 such that the outlet member 655 engages, pierces, punctures, ruptures, and/or otherwise opens a surface or port of the sequestration device 634, thereby placing the device 600 in the second state and/or configuration. As the sequestration device 634 engages the outlet member 655 (e.g., as the outlet member 655 pierces or punctures a port or frangible surface of the sequestration device 634), the lumen of the outlet member 655 is placed in fluid communication with the inner volume of the sequestration device 634. Thus, the reduced or negative pressure within the sequestration device 634 generates or otherwise results in a suction force being exerted through the lumen of the outlet member 655.

As shown in FIG. 18, the actuator 650 can remain in its first state, position, and/or configuration when the sequestration device 634 is moved relative to the housing 630 (e.g., when the device 600 is placed in the second state and/or configuration). As described in detail above with reference to the devices 100, 200, 300, 400, and/or 500, the negative pressure differential or suction force generated by establishing fluid communication between the sequestration device 634 and the outlet member 655 can be operable to draw bodily fluid from the bodily fluid source (e.g., the patient), through the inlet 632 of the device 600, through the portion of the inner volume 631 defined between the first and second seals 652, through the fluid flow path 654 and the outlet member 655 of the actuator 650, and into the sequestration device 634. Thus, the sequestration device 634 can receive an initial volume of bodily fluid from the bodily fluid source (e.g., the patient) in a manner substantially similar to that described above with reference to the sequestration device 534.

Once the initial volume of bodily fluid is transferred into the sequestration device 634, the device 600 can be placed in and/or transitioned to a third state or configuration. While the actuator 550 is described above as being moved, for example, in a direction opposite to the direction in which the sequestration device 534 was inserted into the housing 530, in the embodiment shown in FIGS. 16-19, the actuator 650 can be configured to transition from the its first state, position, and/or configuration in response to continued movement of the sequestration device 634 relative to the housing 630 (e.g., in the second direction). In other words, in some embodiments, the sequestration device 634 can be moved a first distance in a predetermined direction relative to the housing 630 to transition the device 600 from the first state (FIG. 17) to the second state (FIG. 18), and can be moved a second distance in the predetermined direction relative to the housing 630 to transition the actuator 650 from its first state or position to its second state or position, which, in turn, transitioned the device 600 from the second state (FIG. 18) to a third state (FIG. 19). Thus, as described above with reference to the actuator 550, when the actuator 650 is in the second state, position, and/or configuration, the actuator 650 can allow fluid communication to be established between the inlet 632 and the outlet 636, as shown in FIG. 19. In addition, the actuator 650 can be configured to sequester the fluid flow path 654 the inlet 632 and the outlet 636 of the housing 630, which in turn, sequesters the initial volume of bodily fluid from the inlet 632 and the outlet 636. Moreover, in some instances, the initial volume of bodily fluid can include contaminants and/or undesirable material that is likewise sequestered in the sequestration device 634 and/or from the inlet 632 and the outlet 636.

As described in detail above with reference to the device 500, with the actuator 650 in the second configuration and/or position, a portion of the inner volume 631 defined between, for example, the second seal 652 and a third seal 652 defines the fluid flow path 633 that places the inlet 632 in fluid communication with the outlet 636, as shown in FIG. 19. As such, subsequent volumes of bodily fluid withdrawn from the patient can be substantially free from contaminants and can be transferred from the inlet 632, through the portion of the inner volume 631 (e.g., the fluid flow path 633) and the outlet 636, and into one or more fluid collection devices coupled to the outlet 636. Thus, the device 600 can be configured to procure one or more volumes of bodily fluid (e.g., used for bodily fluid sampling or the like) that are substantially free of contaminants.

Figure 20:
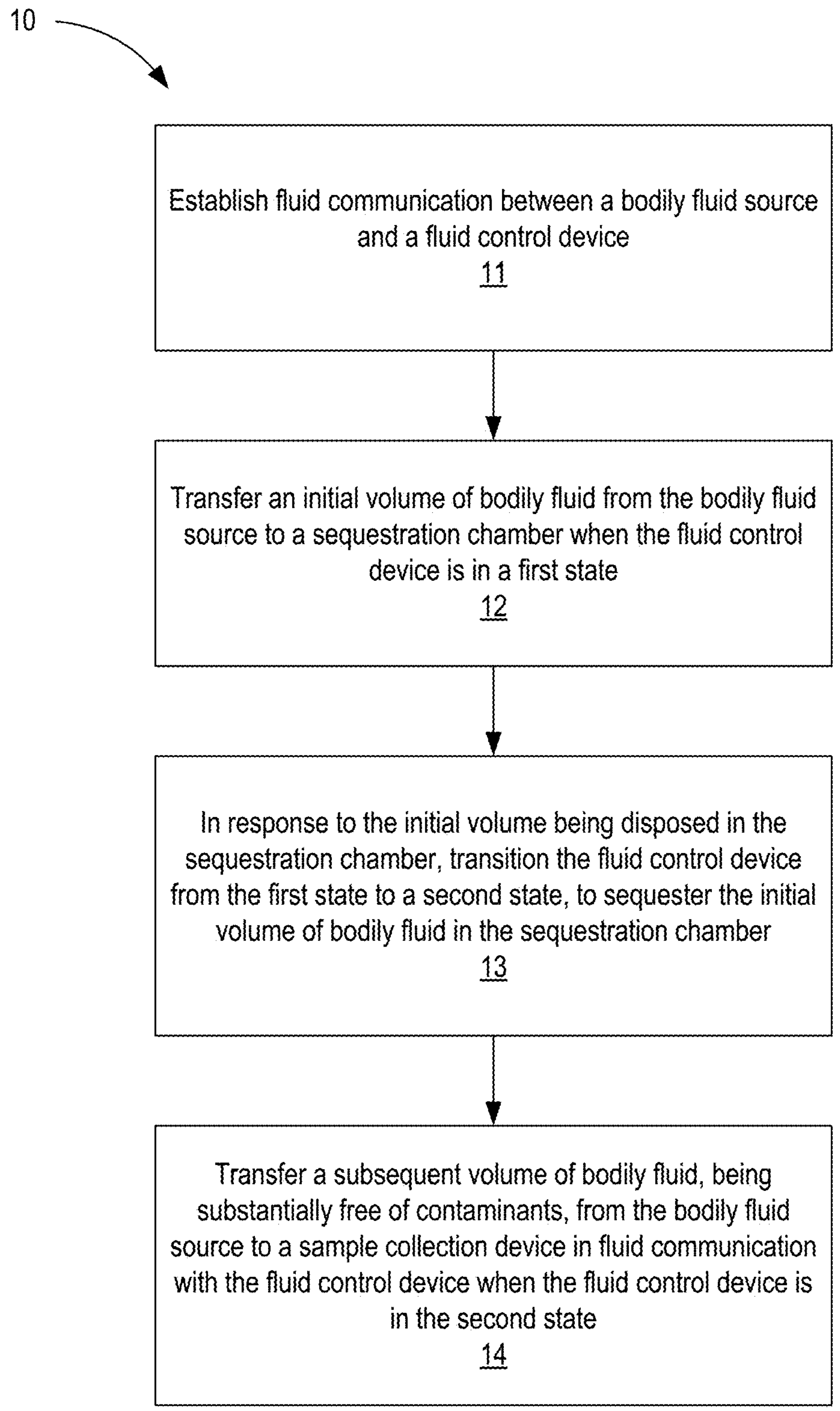
FIG. 20 is a flowchart illustrating a method of using a fluid control device to procure bodily fluid samples with reduced contamination according to an embodiment.

Referring now to FIG. 20, a flowchart is shown illustrating a method 10 of using a fluid control device, such as those described herein, to divert an initial volume of bodily fluid to procure bodily fluid samples with reduced contamination, according to an embodiment. The fluid control device (also referred to herein as "control device") includes an inlet device and a housing and can also include one or more actuators associated with the housing and/or the inlet device. In some embodiments, the control device can be similar to and/or substantially the same as any of the control devices 100, 200, 300, 400, 500, and/or 600 described herein.

The method 10 includes establishing fluid communication between a bodily fluid source and the fluid control device, at 11. In some instances, for example, the bodily fluid source can be a fluid source within a patient's body. More specifically, in some instances, the bodily fluid source can be a vein and/or vascular structure in the patient's body. As described above, the inlet device can be any suitable device configured to establish fluid communication with the bodily, fluid source such as, for example, an intravenous catheter, a butterfly needle, and/or the like. In other embodiments, the inlet device can be any suitable coupler, port, etc. configured to fluidically couple to the bodily fluid source. Accordingly, in some embodiments, establishing fluid communication between the bodily fluid source and the control device can include placing the control device in fluid communication with the inlet device.

In some embodiments, the device can be in a storage and/or pre-use state and/or configuration prior to use. For example, in some embodiments, the one or more actuators can be in a pre-use state and/or configuration. In some embodiments, such a state and/or configuration can be such that at least portions of the control device are isolated, thereby maintaining the sterility of such portions. In some instances, prior to establishing contact with a source of bodily fluid, the control device can be vented using a suitable procedure, as described herein. The venting procedure may include venting of one or more sequestration and/or diversion portions associated with the device, that is, one or more sequestration and/or diversion portions defined by the housing and/or the inlet device. The control device can be placed in a venting configuration to carry out the venting procedure. In some embodiments, the one or more actuators may be in the pre-use state and/or configuration and/or can be placed in a venting state and/or configuration to allow for venting of the device and/or sequestration and/or diversion portions. In such embodiments, once sufficiently vented, the one or more actuators can be transitioned from the venting configuration to a first positon and/or the like. In some instances, the one or more actuators can be transitioned prior to, on, and/or after establishing contact between the bodily fluid source and the inlet device. In some embodiments, the venting and/or charging of the sequestration and/or diversion portions) can be the result of placing the sequestration and/or diversion portion(s) in fluid communication with one or more external negative pressure sources. In some embodiments, for example, such an external negative pressure source can be a fluid collection device such as those described herein. In other embodiments, the external negative pressure source can be any suitable member, device, and/or source.

Having established fluid communication with the bodily fluid source, an initial volume of bodily fluid is transferred from the bodily fluid source to the one or more sequestration and/or diversion portions when the device is in a first state (e.g., with or without the actuator being in a first state or position), at 12. In some embodiments, the control device is in a first state and/or configuration prior to use. As such, establishing fluid communication with the bodily fluid source automatically establishes fluid communication with the sequestration and/or diversion portion. In other embodiments, transitioning the actuator from the pre-use and/or venting state or configuration to the first state and/or configuration can be operable to place the control device in the first state to allow the initial volume of bodily fluid to be transferred to the one or more sequestration and/or diversion portions. In some embodiments, the initial volume of bodily fluid can be transferred and/or drawn into the sequestration and/or diversion portion(s) in response to a negative pressure differential. In some such embodiments, the negative pressure differential can result from placing the sequestration and/or diversion portion in fluid communication with a negative pressure source such as, for example, a fluid collection device (as described above). As such, the negative pressure can be operable to draw bodily fluid into the sequestration and/or diversion portion without transferring bodily fluid into the fluid collection device prior to the initial volume being transferred and sequestered in the sequestration and/or diversion portion.

As described in detail herein, the initial volume can be any suitable volume of bodily, fluid. For example, in some instances, the initial volume can be as small as one drop of bodily, fluid (or a relatively few drops of bodily fluid). In other instances, the initial volume can be, for example, up to about 30 ml, 40 mL, 50 mL, or more. Moreover, as described in detail above with reference to specific embodiments, the initial volume can be at least partially based on and/or can be associated with an amount of bodily fluid that can be contained and/or sequestered in the sequestration and/or diversion portion. In some instances, the initial volume can be a volume that is sufficient to entrain and/or contain substantially all the undesired microbes that may have been dislodged and/or the like as the fluid communication was being established between the bodily fluid source and the inlet device.

In response to the initial volume of bodily fluid being disposed in the sequestration and/or diversion portion, the device is transitioned (e.g., automatically, passively, or in response to an actuation) from the first state to the second state to sequester the initial volume of bodily fluid in the sequestration and/or diversion portion, at 13. In some embodiments, the device can be transitioned from the first state to the second state in response to the one or more associated actuators being transitioned from the first state and/or configuration to a second state and/or configuration. The transitioning of the one or more actuators from the first state and/or configuration to the second state and/or configuration can be in response to any suitable passive or active input such as those described above with reference to the actuators 150, 250, 350, 450, 550, and/or 650.

In some embodiments, the initial volume of bodily fluid can fill the sequestration and/or diversion portion such that any additional volume of bodily fluid is prevented from entering and/or being contained in the sequestration and/or diversion portion. In such embodiments, the fully filled sequestration and/or diversion portion can form, for example, a fluid lock or the like that prevents additional amounts of bodily fluid from entering the sequestration and/or diversion portion and/or that prevents bodily fluid from exiting the sequestration and/or diversion portion. In some embodiments, the sequestration and/or diversion portion can include a hydrophilic material or the like (e.g., as described above with reference to the housing 130) that can absorb and/or retain (e.g., sequester) the bodily fluid contained in the sequestration and/or diversion portion. In some embodiments, the sequestration and/or diversion portion can retain and/or sequester the initial volume of bodily fluid in any suitable manner such as those described herein. For example, in some embodiments, a fully filled or saturated sequestration and/or diversion portion may automatically activate, transition, switch, and/or otherwise reconfigure the actuator (e.g., to transition the actuator from the first state to the second state), which in turn, sequesters the sequestration and/or diversion portion. In some other embodiments, active user intervention can transition the actuator from the first state to the second state, regardless of the degree of volume of bodily fluid transferred into the sequestration and/or diversion portion, to sequester the sequestration and/or diversion portion. In still other embodiments, the transitioning of the actuator can be based on any other suitable input, device, mechanisms, etc. For example, in some embodiments actuator can be, for example, time dependent or pressure dependent.

With the device being transitioned (e.g., actively or passively) to the second state, and the actuator being transitioned (e.g., actively or passively) to the second position, a subsequent volume of bodily fluid is transferred from the bodily fluid source to a fluid collection device (e.g., such as any of those described herein) in fluid communication with the device, at 14. As described in detail above, the sequestering of the initial volume of bodily fluid in the sequestration and/or diversion portion likewise sequesters any contaminants in the sequestration and/or diversion portion. Accordingly, the subsequent volume of bodily fluid transferred to the fluid collection device is substantially free of contaminants.

Figure 21:
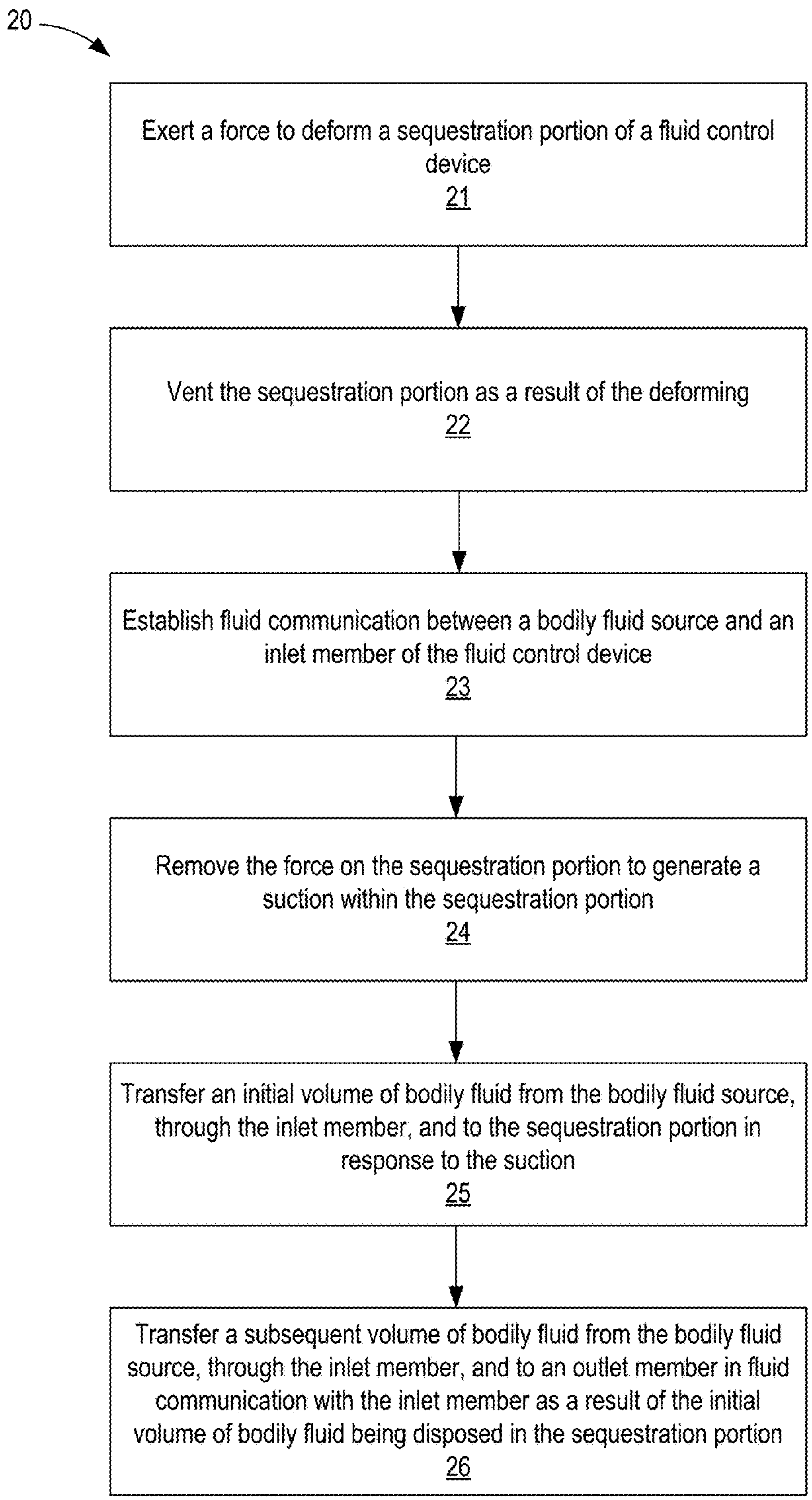
FIG. 21 is a flowchart illustrating a method of using a fluid control device to procure bodily fluid samples with reduced contamination according to an embodiment.

Referring now to FIG. 21, a flowchart is shown illustrating a method 20 of using a fluid control device, such as those described herein, to divert an initial volume of bodily fluid to procure bodily fluid samples with reduced contamination, according to an embodiment. The fluid control device (also referred to herein as "device") includes an inlet device and a housing and can also include one or more actuators associated with the housing and/or the inlet device. In some embodiments, the control device can be similar to and/or substantially the same as, for example, the control device 400 described above with reference to FIGS. 8-H.

The method 20 includes exerting a force to deform a sequestration portion of the fluid control device, at 21. For example, in some embodiments, the control device (e.g., the control device 400) can be arranged as and/or arranged similar to a butterfly needle with one or more sequestration portions housed within and/or formed by the "wings" of the butterfly needle (see e.g., FIGS. 8 and 9). In such embodiments, the sequestration portion can be formed of a relatively flexible and/or movable material configured to deform in response an external force (e.g., applied by a user), which in turn, can result in a compression of the sequestration portion.

The sequestration portion is vented as a result of the deforming, at 22. For example, in some instances, a compression force can be exerted on a part of the sequestration portion that can expel air and/or other contents disposed within the sequestration portion. In some embodiments, the venting can be through at least one of an inlet member or an outlet member of the control device or the control device can include at least one vent, opening, port, valve, etc. configured to allow air or gas to vent from the sequestration portion, as described above with reference to the control device 400.

Fluid communication between the inlet member of the control device and a bodily fluid source is established, at 23. Establishing fluid communication between the inlet member and the bodily fluid source can be prior to or after venting the sequestration portion. In some embodiments, the inlet member can be a needle configured to be inserted into a patient. In other embodiments, the inlet member can be coupled to any suitable intervening device configured to establish fluid communication with the bodily fluid source.

The force on the sequestration portion is removed to generate a suction within the sequestration portion, at 24. For example, in some instances, following venting of the sequestration portion and establishing fluid communication between the inlet member and the bodily fluid source, the control device can be in a charged and/or primed state in which the sequestration portion can remain deformed, compressed, collapsed, and/or vented. Once fluid communication is established between the inlet member and the bodily fluid source, the force can be removed from the sequestration portion. For example, in some instances, the user can exert the force by squeezing a part of the sequestration portion and can remove the force to allow the sequestration portion to return to an undeformed, uncompressed, and/or non-collapsed configuration, which in turn, can result in an increase in a volume within the sequestration portion.

As described in detail herein, in some instances, the increase in volume inside the sequestration portion can generate the suction force (e.g., a reduced or negative pressure state) within the sequestration portion. In response to the suction, an initial volume of bodily fluid is transferred from the bodily fluid source, through the inlet member, and to the sequestration portion, at 25. Thus, the suction and/or a negative pressure within the sequestration portion can draw, urge, and/or encourage flow of bodily fluid into and/or through one or more fluid flow paths from the bodily fluid source and into the sequestration portions (as described in detail above).

As a result of the initial volume of bodily fluid being disposed in the sequestration portion, a subsequent volume of bodily fluid is transferred from the bodily fluid source, through the inlet member, and to the outlet member in fluid communication with the inlet member, at 26. For example, in some instances, the flow of bodily fluid into the sequestration portion can cease gradually or abruptly due to any suitable active or passive mechanism such as any of those described herein. In some instances, once the initial volume of bodily fluid is disposed in the sequestration portion, the control device can be transitioned from a first state to a second state such that bodily fluid can flow from the inlet member to the outlet member. In some instances, when the control device is placed in the second state, the initial volume of bodily fluid, which can contain contaminants and/or the like, can be sequestered in the sequestration portion. As such, subsequent volumes of bodily fluid, substantially free of contaminants, can be drawn from the bodily fluid source, through the inlet member, and to the outlet member. Moreover, as described in detail herein, the outlet member can be configured to couple to any suitable fluid collection device. Accordingly, the method 20 can be used to divert an initial volume of bodily fluid to procure bodily fluid samples with reduced contamination.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made.

For example, while the inlet devices 110, 310, and/or 410 have been described above as including or coupling to a needle or the like configured to puncture the skin of a patient to place the lumen of the needle in fluid communication with a vein in the patient, in other embodiments, a fluid control device can include any suitable inlet device. For example, in some embodiments, the inlet device can include a trocar or the like and a catheter. The trocar is configured to puncture the skin of a patient and then configured to be withdrawn from the patient, leaving the catheter of the inlet device placed within the patient. In other embodiments, the inlet device need not puncture the skin of a patient. For example, in some embodiments, the inlet device can include a needle or catheter that can be placed in a dish, well, sample volume, container, reservoir, etc. In still other embodiments, the inlet device can be and/or can include a coupler or port configured to couple to an indwelling needle or intravenous catheter. In other embodiments, such a coupler or port can be configured to couple to any suitable bodily fluid source (or port thereof) such as, for example, a syringe, a reservoir, a container, etc.

Accordingly, while the embodiments are described above as withdrawing and sequestering an initial volume of bodily fluid to sequester contaminants such as, for example, dermally-residing microbes, in other embodiments, the inlet device can be coupled to any suitable bodily fluid source and the device can be configured to sequester an initial volume of bodily fluid withdrawn from that bodily fluid source to sequester contaminants that may be present within the source and/or any an interface of the container or reservoir containing the bodily fluid. For example, in some embodiments, a needle of an inlet device can be configured to puncture a port or surface of a reservoir to place the needle in fluid communication with an interior volume of the container or device. In such embodiments, the devices described herein can be used to sequester an initial volume of bodily fluid from the bodily fluid source, which in turn, can sequester contaminants or the like that may have been present on the interface, port, or surface that was punctured. Thus, the devices and methods described herein can be used to procure bodily fluid samples having reduced contamination from any suitable bodily fluid source. Moreover, while some such contaminants are described herein as being dermally residing microbes, it should be understood that the contaminants can be any contaminant that is/are, for example, exterior to the bodily fluid source and/or otherwise that is or that includes any constituent component (e.g., microbe, virus, molecule, particle, element, etc.) that is otherwise foreign to the bodily fluid.

As another example, while the control devices 100, 200, 300, 400, 500, and/or 600 are described as transferring a bodily fluid into the device via specific passive or active mechanisms or means of producing negative pressure differentials between two or more portions of the device, in other embodiments, negative pressure differentials can be produced and/or can otherwise result from any suitable means. By way of example, in some embodiments, an outlet of a control device can be coupled to a syringe, a pump, and/or the like. In other embodiments, a control device can include a pre-charged sequestration chamber (e.g., similar to the sequestration devices 534 and/or 634), a vented sequestration chamber, a manually activated device configured to produce a negative pressure, an energy source, and/or any other suitable means of defining and/or forming a pressure differential within a portion of the control device.

Any of the fluid control devices and/or methods described herein can use an external negative pressure source (e.g., provided by a sequestration device, a fluid collection device, and/or any other suitable means) to (1) overcome physical patient challenges which can limit and/or prevent a sufficient pressure differential (e.g., a differential in blood pressure to ambient air pressure) to fully engage the sequestration chamber and/or to transition fluid flow to the fluid collection device; (2) result in proper filling of the sequestration chamber with a clinically validated and/or desirable volume of bodily fluid; (3) result in efficient, timely, and/or user-accepted consistency with bodily fluid collection process; and/or (4) provide a means of manipulating and/or automatically transitioning fluid flow (e.g., movement of physical components of the system or changing, switching, engaging, and/or otherwise employing or achieving desired fluid flow dynamics) to enable sequestration and/or isolation of the initial sample and collection of a subsequent sample.

In some embodiments, a method of using a fluid control device employing an external negative pressure source can include the ordered steps of establishing fluid communication between a bodily fluid source (e.g., a vein of a patient or the like) and an inlet of the fluid control device. An outlet of the fluid control device is then placed in fluid communication with and/or otherwise engages a negative pressure source. Such a negative pressure source can be a sample reservoir, a syringe, an evacuated container, an intermediate transfer device, and/or the like. The fluid control device can be in a first state or operating mode when the outlet is coupled to the negative pressure source and, as such, a negative pressure differential is applied through at least a portion of the fluid control device that can be operable to draw an initial volume of bodily fluid into a sequestration chamber of the fluid control device. Once the initial volume of bodily fluid is disposed in the sequestration chamber, the fluid control device is transitioned, either automatically or via user intervention, from the first state or operating mode to a second state or operating mode such that (1) the initial volume is sequestered in the sequestration chamber and (2) fluid communication is established between the inlet and the outlet. The sequestration of the initial volume can be such that contaminants entrained in the flow of the initial volume are likewise sequestered within the sequestration chamber. With the initial volume of bodily fluid sequestered in the sequestration chamber and with fluid communication established between the inlet and the outlet, subsequent volumes of bodily fluid that are substantially free of contamination can be collected in one or more sample reservoirs.

In some embodiments, any of the fluid control devices described herein can be formed from any suitable components that can be manufactured, sterilized, and packaged as individual parts or components. In such embodiments, a user can, for example, open one or more packages containing one or more components, can assemble the components to form the fluid control device, and can use the fluid control device as described above. For example, in some embodiments, the devices 500 and 600 can each be manufactured, sterilized, and packaged separate from the sequestration device 534 and 634, respectively. In other embodiments, any of the fluid control devices described herein can be formed from any suitable components that can be manufactured, sterilized, assembled, and packaged as an assembly or integrated device. For example, in some embodiments, the devices 500 and 600 can each be sterilized, assembled, and/or packaged with one or more sequestration device 534 and/or 634. In such embodiments, a user can, for example, open a packaging containing such an assembly or integrated device and can use the device as described above without further assembly of components. In some embodiments, any of the control devices can be monolithically formed in whole or at least in part.

In some embodiments, any of the control devices can be physically and/or fluidically coupled to a collection device (e.g., a sample reservoir, a syringe, a blood culture bottle, a collection vial, a fluid transfer container, and/or any other suitable reservoir, collection device, and/or transfer device) by a user prior to or during use, as described in detail above. In other embodiments, any of the control devices can be physically coupled, attached, formed, and/or otherwise mated to a fluid collection device during a manufacturing process. This can be done prior to sterilization so the collection pathway(s) and connection interface(s) (e.g., where the control device couples to the fluid collection device) maintain a closed-system, mechanical diversion device within a sterile environment that is not subject to touch-point contamination from external sources.

In some embodiments, the pre-assembly of the control device and the collection device can be such that the user is forced first to sequester, segregate, and/or isolate at least a portion of the initial bodily fluid volume or flow prior to transferring a sample volume to the pre-assembled fluid collection device. For example, the control device can include an actuator that is configured to isolate an outlet from other portions of the control device, thereby isolating the collection device from such portions of the control device. Moreover, after transferring the initial volume of bodily fluid, the actuation of the actuator can result in sequestration of the initial volume of bodily fluid and the fluidic coupling of the outlet to additional portions of the control device (e.g., an inlet). In some embodiments, pre-assembling the control device and the collection device (e.g., during manufacturing) can, for example, force compliance with a sample procurement protocol that calls for the sequestration of an initial amount of bodily fluid prior to collecting a sample volume of bodily fluid.

In some embodiments, the coupling, mating, and/or attachment of the fluid control device to the fluid collection device (e.g., during manufacturing) can be executed such that the control device can be removed (physically decoupled, removed with a specific "key," and/or any other approach used to separate the control device from the fluid collection device) after use to allow access to the fluid collection device. After decoupling, the collection device can be placed in an incubator and/or any other type of analytical machine, and accessed for analysis and/or otherwise further processed. In some embodiments, such decoupling may be blocked, limited, and/or substantially prevented prior to use and unblocked or allowed after use. In other embodiments, the fluid control device and the fluid collection device can be permanently coupled and/or monolithically formed (at least in part) to prevent such decoupling.

Any of the embodiments described herein can be used in conjunction with any suitable fluid transfer, fluid collection, and/or fluid storage device such as, for example, the fluid reservoirs described in the '420 patent, the transfer devices described in the '510 publication, and/or the transfer adapters described in U.S. Pat. No. 10,123,783 entitled, "Apparatus and Methods for Disinfection of a Specimen Container," filed Mar. 3, 2015. In some embodiments, any of the embodiments described herein can be used in conjunction with fluid transfer, fluid collection, and/or fluid storage devices such as, for example, the devices described in U.S. Pat. No. 8,535,241 entitled, "Fluid Diversion Mechanism for Bodily-Fluid Sampling," filed Oct. 12, 2012 U.S. Pat. No. 9,060,724 entitled, "Fluid Diversion Mechanism for Bodily-Fluid Sampling," filed May 29, 2013; U.S. Pat. No. 9,155,495 entitled, "Syringe-Based Fluid Diversion Mechanism for Bodily-Fluid Sampling," filed Dec. 2, 2013; U.S. Patent Publication No. 2016/0361006 entitled, "Devices and Methods for Syringe-Based Fluid Transfer for Bodily-Fluid Sampling," filed Jun. 13, 2016; U.S. Patent Publication No. 2018/0140240 entitled, "Systems and Methods for Sample Collection with Reduced Hemolysis," filed Nov. 20, 2017; and/or U.S. Pat. No. 9,950,084 entitled, "Apparatus and Methods for Maintaining Sterility of a Specimen Container," filed Sep. 6, 2016, the disclosure of each of which is incorporated herein by reference in its entirety.

Although various embodiments have been described as having particular features, concepts, and/or combinations of components, other embodiments are possible having any combination or sub-combination of any features, concepts, and/or components from any of the embodiments described herein. For example, as described above, any of the devices 100, 200, 300, and/or 400 can, in some embodiments, be arranged and/or configured such that the fluid collection device provides a negative pressure or pressure differential that can be operable to draw bodily fluid into the sequestration and/or diversion portion 134, 234, 334, and/or 434, respectively. In some embodiments, a device can include parallel fluid flow paths or the like and can place an inlet of the device (or a housing of the device) in fluid communication with a sequestration and/or diversion portion and a fluid collection device in parallel. In some embodiments, the diversion of fluid can be controlled by the above-described automatic or passive (e.g., non-user mediated) methods, while additional control mechanisms for user-intervention (e.g., control switches, valves, ports) can be available to add and/or control various parameters of fluid diversion such as volume, rate of diversion, and/or the like. In some embodiments, a negative pressure produced by the fluid collection device can be operable to draw bodily fluid through the inlet and the device can include any suitable means of directing and/or diverting an initial flow of the bodily fluid through the sequestration and/or diversion portion prior to directing and/or diverting a subsequent flow of bodily fluid to the fluid collection device such as, for example, any of the actuators described herein.

The specific configurations of the various components can also be varied. For example, the size and specific shape of the various components can be different from the embodiments shown, while still providing the functions as described herein. More specifically, the size and shape of the various components can be specifically selected for a desired rate and/or volume of bodily fluid flow into a fluid reservoir. For example, the perimeter, the diameter, and/or the cross-sectional area of any of the fluid flow paths described herein can be designed and/or specifically, selected to accommodate a flow or translocation of fluids (e.g., bodily fluids), gases (e.g., air), or any suitable combination thereof at a desired flow rate. In other words, the components of the fluid control devices described herein, including those components built separately and later affixed together, can be selected individually or together to satisfy desired sample procurement criteria such as, for example, a magnitude of pressure differentials, a desired flow rate of bodily fluid through portions of the device, the ability to modulate pressures and/or flow rates, and/or the like. Likewise, the size and/or shape of the various components can be specifically selected for a desired or intended usage. For example, in some embodiments, devices such as those described herein can be configured for use with or on seemingly healthy adult patients. In such embodiments, the device can include a sequestration chamber that has a first volume (e.g., about 0.5 ml to about 5.0 ml). In other embodiments, a device such as those described herein can be configured for use with or on, for example, very sick patients and/or pediatric patients. In such embodiments, the device can include a sequestration chamber that has a second volume that is less than the first volume e.g., less than about 0.5 Thus, size, shape, and/or arrangement of the embodiments and/or components thereof can be adapted for a given use unless the context explicitly states otherwise.

Although not shown, any of the devices described herein can include an opening, port, coupler, septum, Luer-Lok, gasket, valve, threaded connecter, standard fluidic interface, etc. (referred to for simplicity as a "port") in fluid communication with the sequestration chamber. In some such embodiments, the port can be configured to couple to any suitable device, reservoir, pressure source, etc. For example, in some embodiments, the port can be configured to couple to a reservoir, which in turn, can al low a greater volume of bodily fluid to be diverted and/or transferred into the sequestration chamber. In some embodiments, the port can be coupled to a negative pressure source such as an evacuated container, a pump, a syringe, and/or the like to collect a portion of or the full volume of bodily fluid in the sequestration chamber, channel, reservoir, etc. and use that volume of bodily fluid (e.g., the pre-sample volume) for additional clinical and/or in vitro diagnostic testing purposes. In other embodiments, the port can be coupled to any suitable pressure source or infusion device configured to infuse the initial volume of bodily fluid sequestered in the sequestration chamber back into the patient and/or bodily fluid source (e.g., in the case of pediatric patients, very sick patients, patients having a low blood volume, and/or the like).

In some embodiments, the port can be configured to receive a probe, sampling tool, testing device, and/or the like that can be used to perform one or more tests (e.g., tests not sensitive to potential contamination) on the initial volume while the initial volume is disposed or sequestered in the sequestration chamber. In other embodiments, the sequestration channel, chamber, and/or reservoir can be configured with the addition of other diagnostic testing components integrated into the chamber (e.g., a paper test) such that the initial bodily fluid is used for that test. In still other embodiments, the sequestration chamber, channel, and/or reservoir can be designed, sized, and configured to be removable and compatible with testing equipment and/or specifically accessible for other types of bodily fluid tests commonly performed on patients with suspected conditions. By way of example, a patient with suspected sepsis commonly has blood samples collected for lactate testing, procalcitonin testing, and blood culture testing. All of the fluid control devices described herein can be configured such that the sequestration chamber, channel, reservoir, etc. can be removed (e.g., after receiving the initial volume of bodily fluid) and the bodily fluid contained therein can be used for these additional testing purposes before or after the subsequent sample is collected for microbial testing.

Although not shown, in some embodiments, a fluid control device can include one or more lumen, channels, flow paths, etc. configured to selectively allow for a "bypass" flow of bodily fluid, where an initial amount or volume of bodily fluid can flow from the inlet, through the lumen, cannel, flow path, etc. to bypass the sequestration chamber, and into the collection device. In some embodiments, the fluid control device can include an actuator having, for example, at least three states a first in which bodily fluid can flow from the inlet to the sequestration chamber, a second in which bodily fluid can flow from the inlet to the outlet after the initial volume is sequestered in the sequestration chamber, and a third in which bodily fluid can flow from the inlet, through the bypass flow path, and to the outlet. In other embodiments, the control device can include a first actuator configured to transition the device between a first and second state, as described in detail above with reference to specific embodiments, and can include a second actuator configured to transition the device to a bypass configuration or the like. In still other embodiments, the control device can include any suitable device, feature, component, mechanism, actuator, controller, etc. configured to selectively place the fluid control device in a bypass configuration or state.

Where methods and/or events described above indicate certain events and/or procedures occurring in certain order, the ordering of certain events and/or procedures may be modified and that such modifications are in accordance with the variations of the invention, Additionally, certain events and/or procedures may be performed concurrently in a parallel process when possible, as well as performed sequentially as described above. Certain steps may be partially completed or may be omitted before proceeding to subsequent steps. For example, while the devices are described herein as transitioning from a first state to a second state in a discrete operation or the like, it should be understood that the devices described herein can be configured to automatically and/or passively transition from the first state to the second state and that such a transitioning may occur over a period of time. In other words, the transitioning from the first state to the second state may, in some instances, be relatively gradual such that as a last portion of the initial volume of bodily fluid is being transferred into the sequestration chamber, the control device begins to transition from the first state to the second state. In some instances, the rate of change when transitioning from the first state to the second state can be selectively controlled to achieve one or more desired characteristics associated with the transition. Moreover, in some such instances, the inflow of the last portion of the initial volume can limit and/or substantially prevent bodily fluid already disposed in the sequestration chamber from escaping therefrom. Accordingly, while the transitioning from the first state to the second state may occur over a given amount of time, the sequestration chamber can nonetheless sequester the volume of bodily fluid disposed therein.

While the embodiments and/or methods are described above as being transitioned from a first state and/or configuration in which the initial volume of bodily fluid flows from an inlet into or toward a sequestration and/or diversion portion and a second state and/or configuration in which a subsequent volume of bodily fluid flows from the inlet to an outlet or fluid collection device, in other embodiments, a fluid control device can have any suitable number of states and/or configurations therebetween. For example, some of the fluid control devices are described herein as having first state in which an actuator allows an initial volume of bodily fluid to flow from an inlet of the control device to a sequestration and/or diversion portion while blocking bodily fluid flow to an outlet or fluid collection device, and a second state in which the actuator blocks bodily, fluid flow into or out of the sequestration and/or diversion portion and allows subsequent volumes of bodily fluid to flow from the inlet to the outlet or fluid collection device. In some embodiments, however, a control device and/or an actuator included therein can be placed in one or more intermediate states, temporarily, that neither allow fluid flow to a sequestration and/or diversion portion nor to an outlet. In other words, such an actuator can be transitioned to states or configurations different from and/or in addition to the first state or the second state.

For example, between assuming the first state of allowing fluid flow to the sequestration and/or diversion portion and assuming the second state of allowing fluid flow to the outlet, the actuator can assume or can be switched to an intermediate position that blocks a fluid flow path between the inlet and both the sequestration and/or diversion portion and the outlet. In some such embodiments, the drawing of the bodily fluid can be stopped from flowing to the sequestration and/or diversion portion or to the outlet by placing the actuator in one or more of the intermediate states and/or configurations. In some instances, from an intermediate state, the actuator can assume or can be switched to the first configuration to continue drawing fluid to the sequestration and/or diversion portion or can assume or can be switched to the second configuration to draw fluid to the outlet and/or the fluid collection device. In some embodiments, allowing for one or more intermediate states and/or configurations can allow a user to modulate a negative pressure exerted on or through the inlet. In other embodiments, transitioning the actuator through one or more intermediate states between the first state and the second state can limit and/or can substantially prevent the actuator from inadvertently being transitioned from the first state to the second state prior to collecting the initial volume of bodily fluid, which can otherwise result in contaminants being transferred into a sample volume of bodily fluid.

What is claimed:

1. An apparatus, comprising:

a body having an inlet configured to be placed in fluid communication with a bodily fluid source and an outlet configured to be coupled to a fluid collection device;

a reservoir configured to receive an initial volume of bodily fluid; and a diverter defining a first fluid flow path and a second fluid flow path each configured to allow a flow of bodily fluid through at least a portion of the body, the diverter configured in a first state to vent a gas from the reservoir via at least the first fluid flow path and the outlet to establish a negative pressure differential between the reservoir and the inlet, the diverter configured to transition from the first state to a second state after venting the reservoir such that the first fluid flow path establishes fluid communication between the reservoir and the inlet to allow the initial volume of bodily fluid to transfer into the reservoir, the diverter configured to transition from the second state to a third state after the initial volume of bodily fluid is transferred into the reservoir such that (1) the initial volume of bodily fluid is contained in the reservoir and (2) the second fluid flow path places the outlet in fluid communication with the inlet to allow a subsequent volume of bodily fluid to be transferred through the second fluid flow path to the fluid collection device when the fluid collection device is coupled to the outlet.

2. The apparatus of claim 1, wherein the diverter is configured to automatically transition between at least the second state and the third state.

3. The apparatus of claim 1, wherein the diverter is configured to rotate to transition between the first state, the second state, and the third state.

4. The apparatus of claim 1, wherein the diverter is configured to transition from the second state to the third state in response to bodily fluid being transferred to the reservoir after a predetermined volume is collected in the reservoir.

5. The apparatus of claim 4, wherein the predetermined volume is based at least in part on a predetermined flow rate of the flow of bodily fluid being transferred to the reservoir.

6. The apparatus of claim 1, wherein when in the first state, the diverter is configured to establish a fluid communication between the reservoir and the outlet with the first fluid flow path, the outlet configured to transition from a closed state to an open state as a result of being coupled to the fluid collection device to establish fluid communication therebetween.

7. An apparatus, comprising:

a body having an inlet configured to be placed in fluid communication with a bodily fluid source and an outlet configured to be coupled to a fluid collection device; a reservoir configured to receive an initial volume of bodily fluid; and a diverter defining a first fluid flow path and a second fluid flow path each configured to allow a flow of bodily fluid through at least a portion of the body, the diverter configured in a first state to establish fluid communication between the reservoir and the outlet with the first fluid flow path, the outlet configured to transition from a closed state to an open state when the diverter is in the first state to vent a gas from the reservoir via at least the first fluid flow path and the outlet, the diverter configured to transition from the first state to a second state after venting the reservoir such that the first fluid flow path establishes fluid communication between the reservoir and the inlet to allow the initial volume of bodily fluid to transfer into the reservoir, the diverter configured to transition from the second state to a third state after the initial volume of bodily fluid is transferred into the reservoir such that (1) the initial volume of bodily fluid is contained in the reservoir and (2) the second fluid flow path places the outlet in fluid communication with the inlet via the at least one fluid flow path to allow a subsequent volume of bodily fluid to be transferred to the fluid collection device when the fluid collection device is coupled to the outlet and the outlet is in the open state.

8. The apparatus of claim 7, wherein the body at least partially defines the reservoir, and the reservoir and the outlet are sequestered from a volume outside of the body when the diverter is in the first state and the outlet is in the closed state.

9. The apparatus of claim 7, wherein the venting of the reservoir charges the reservoir in response to a negative pressure within the fluid collection device.

10. An apparatus, comprising:

a body having an inlet configured to be placed in fluid communication with a bodily fluid source and an outlet configured to be coupled to a fluid collection device; a reservoir configured to receive an initial volume of bodily fluid; and a diverter defining a first fluid flow path and a second fluid flow path each configured to allow a flow of bodily fluid through at least a portion of the body, the diverter configured in a first state to establish fluid communication between the reservoir and the outlet with the first fluid flow path, the outlet configured to transition from a closed state to an open state as a result of being coupled to the fluid collection device to establish fluid communication therebetween and when the diverter is in the first state to vent a gas from the reservoir via at least the first fluid flow path and the outlet, the venting of the reservoir operable to charge the reservoir with a negative pressure, the diverter configured to transition from the first state to a second state after venting the reservoir such that the first fluid flow path establishes fluid communication between the reservoir and the inlet to allow the initial volume of bodily fluid to transfer into the reservoir, the diverter configured to transition from the second state to a third state after the initial volume of bodily fluid is transferred into the reservoir such that (1) the initial volume of bodily fluid is contained in the reservoir and (2) the second fluid flow path places the outlet in fluid communication with the inlet to allow a subsequent volume of bodily fluid to be transferred to the fluid collection device when the fluid collection device is coupled to the outlet and the outlet is in the open state.

11. The apparatus of claim 10, wherein the venting of the reservoir charges the reservoir in response to a negative pressure within the fluid collection device.

12. The apparatus of claim 10, wherein the diverter is configured to automatically transition between at least the second state and the third state.

13. The apparatus of claim 10, wherein the diverter is configured to transition from the second state to the third state in response to bodily fluid being transferred to the reservoir after a predetermined volume is collected in the reservoir.

14. The apparatus of claim 13, wherein the predetermined volume is based at least in part on a predetermined flow rate of the flow of bodily fluid being transferred to the reservoir.

15. A method of using an apparatus to obtain a bodily fluid sample with reduced contamination, the method comprising:

establishing a fluid communication between a bodily fluid source and an inlet of the apparatus, the inlet being fluidically coupled to:

a reservoir of the apparatus for receiving an initial volume of bodily fluid; and an outlet of the apparatus, for coupling to a fluid collection device;

placing a diverter of the apparatus in a first state to establish a fluid communication between the reservoir and the outlet with a first fluid flow path defined by the diverter;

coupling the outlet to the fluid collection device, thereby transitioning the outlet from a closed state to an open state to establish fluid communication therebetween;

venting a gas from the reservoir via at least the first fluid flow path and the outlet, the venting of the reservoir operable to charge the reservoir with a negative pressure;

transitioning the diverter from the first state to a second state after venting the reservoir such that the first fluid flow path establishes a fluid communication between the reservoir and the inlet to allow the initial volume of bodily fluid to transfer into the reservoir; and transitioning the diverter from the second state to a third state after the initial volume of bodily fluid is transferred into the reservoir such that (1) the initial volume of bodily fluid is contained in the reservoir and (2) a second fluid flow path defined by the diverter places the outlet in fluid communication with the inlet to allow a subsequent volume of bodily fluid to be transferred to the fluid collection device when the fluid collection device is coupled to the outlet and the outlet is in the open state.

16. The method of claim 15, wherein the venting of the reservoir charges the reservoir in response to a negative pressure within the fluid collection device.

17. The method of claim 15, wherein the diverter is configured to automatically transition between at least the second state and the third state.

18. The method of claim 15, wherein the diverter is configured to rotate to transition between the first state, the second state, and the third state.

19. The method of claim 15, wherein the diverter is configured to transition from the second state to the third state in response to bodily fluid being transferred to the reservoir after a predetermined volume is collected in the reservoir.

20. The method of claim 19, wherein the predetermined volume is based at least in part on a predetermined flow rate of the bodily fluid being transferred to the reservoir.

* * * * *